United States Patent [19]

DiNinno et al.

[11] Patent Number: 5,294,610
[45] Date of Patent: Mar. 15, 1994

[54] 2-(AZA-9-FLUORENONYL)CARBAPENEM ANTIBACTERIAL AGENTS

[75] Inventors: Frank P. DiNinno, Old Bridge; Ravindra N. Guthikonda, Edison, both of N.J.

[73] Assignee: Merck & Co. Inc., Rahway, N.J.

[21] Appl. No.: 961,571

[22] Filed: Oct. 15, 1992

[51] Int. Cl.$^5$ .................. C07D 487/00; A01N 43/00; A01K 31/395
[52] U.S. Cl. ..................... 514/210; 540/302
[58] Field of Search ......................... 540/302; 514/210

[56] References Cited

U.S. PATENT DOCUMENTS

| | | |
|---|---|---|
| 4,260,627 | 4/1981 | Christensen et al. ............... 424/274 |
| 4,465,632 | 8/1984 | Christensen et al. ............. 260/245.2 |
| 4,543,257 | 9/1985 | Cama et al. ......................... 514/210 |
| 4,978,659 | 8/1989 | Salzmann et al. . |
| 5,004,739 | 4/1991 | Salzmann et al. . |
| 5,004,740 | 4/1991 | Salzmann et al. . |
| 5,006,519 | 4/1991 | DiNinno et al. . |
| 5,011,832 | 4/1991 | Salzmann et al. . |
| 5,025,006 | 6/1991 | Salzmann et al. . |
| 5,025,007 | 6/1991 | Greenlee et al. . |
| 5,025,008 | 6/1991 | DiNinno et al. . |
| 5,032,587 | 7/1991 | DiNinno et al. . |
| 5,034,384 | 7/1991 | Greenlee et al. . |
| 5,034,385 | 7/1991 | DiNinno et al. . |
| 5,037,820 | 8/1991 | DiNinno et al. . |
| 5,132,422 | 7/1991 | DiNinno et al. . |
| 5,144,028 | 9/1992 | Cama et al. . |

FOREIGN PATENT DOCUMENTS 0277743 8/1988 European Pat. Off. .
0444889 2/1991 European Pat. Off. .

OTHER PUBLICATIONS

L. D. Cama et al., Total Synthesis of Theinamycin Analogs–III, Tetrahedron, 39, 2531 (1983).
R. N. Guthikonda et al., Structure Activity Relationships in the 2-Arylcarbapenem Series, J. Med. Chem., 30, 871 (1987).

*Primary Examiner*—Marianne M. Cintins
*Assistant Examiner*—Rebecca Cook
*Attorney, Agent, or Firm*—Richard C. Billups; Joseph F. DiPrima

[57] ABSTRACT

Carbapenems of the formula

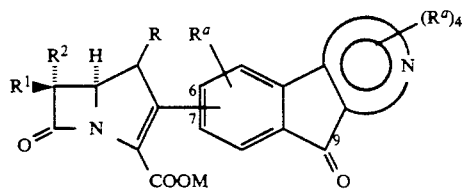

wherein a suitably substituted aza-9-fluorenone is attached at the 2-position of the carbapenem are useful antibacterial agents.

16 Claims, No Drawings

2-(AZA-9-FLUORENONYL)CARBAPENEM ANTIBACTERIAL AGENTS

BACKGROUND OF THE INVENTION

The present invention relates to antibacterial agents of the carbapenem class, in which the 2-position side-chain is characterized by an azafluoren-9-one moiety, substituted by various anionic and neutral substituents, as described in more detail further below.

Thienamycin was an early carbapenem antibacterial agent having a broad spectrum; it has the following formula:

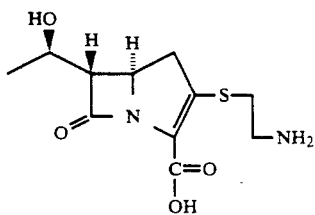

Later, N-formimidoyl thienamycin was discovered; it has the formula:

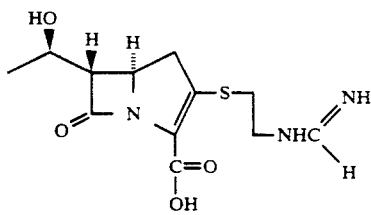

The 2-(aza-9-fluorenonyl)-carbapenems of the present invention are not characterized by a broad antibacterial spectrum such as that of thienamycin or N-formimidoyl thienamycin. Rather, their spectrum of activity is largely limited to gram positive microorganisms, especially methicillin resistant *Staphylococcus aureus* (MRSA), methicillin resistant *Staphylococcus epidermidis* (MRSE), and methicillin resistant coagulase negative Staphylococci (MRCNS). The antibacterial compounds of the present invention thus comprise an important contribution to therapy of these difficult to control pathogens. Morever, there is an increasing need for agents effective against such pathogens (MRSA/MRCNS) which are at the same time safe, i.e., free from undesirable toxic side effects. No β-lactam antibacterial has yet been found which meets these requirements. And, the current agent of choice, vancomycin, a glycopeptide antibacterial, is experiencing an ever increasing amount of resistance in the MRSA/MRCNS pathogens.

More recently, carbapenem antibacterial agents have been described which have a 2-substituent which is an aryl moiety optionally substituted by, e.g., aminomethyl and substituted aminomethyl. These agents are described in U.S. Pat. Nos. 4,543,257 and 4,260,627 and have the formula:

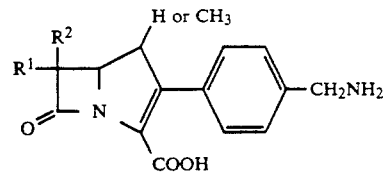

EP-A-0277 743 describes a particular class of compounds of the formula:

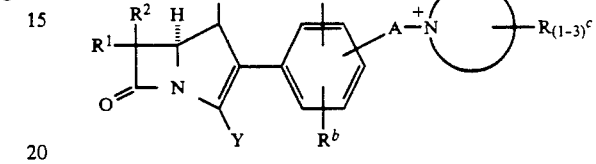

but this limited teaching in no way suggests the totally different compounds of the present invention, nor their surprisingly better anti-MRSA/MRCNS activity.

Recently patents have issued disclosing the 2-substituted carbapenems having anti-MRSA/MRCNS activity (see U.S. Pat. Nos. 5,004,739; 5,004,740; 5,011,832; 5,025,008; 5,032,587; 5,132,422, all assigned to Merck & Co., Inc.). Particularly, patents have issued disclosing 2-and 3-fluoren-9-onyl-2-carbapenems having anti-MRSA/MRCNS activity (see U.S. Pat. Nos. 5,025,007 and 5,034,384). However, there is no published description of or suggestion of a substituted azafluoren-9-onyl 2-substituent such as characterizes the compounds of the present invention.

SUMMARY OF THE INVENTION

The present invention provides novel carbapenem compounds of the formula:

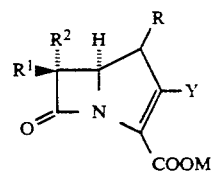

I wherein:
Y is:

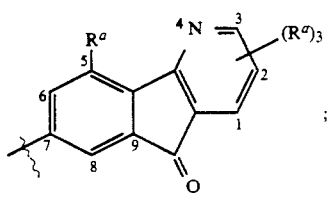

a)

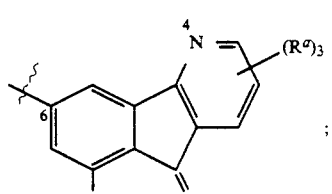

b)

-continued

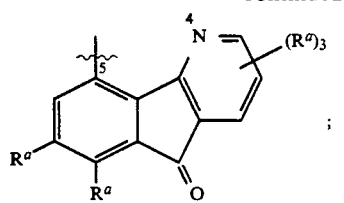
;

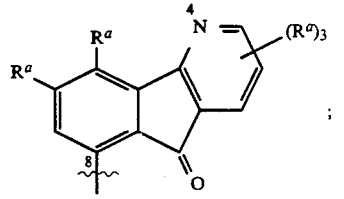
;

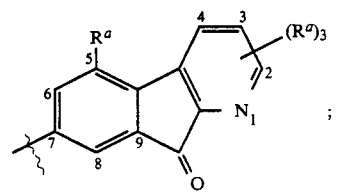
;

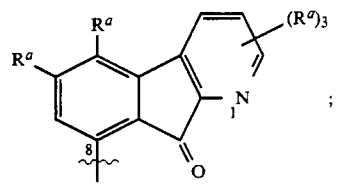
;

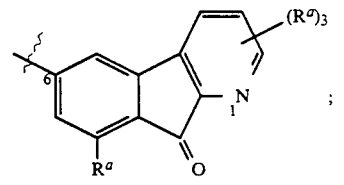
;

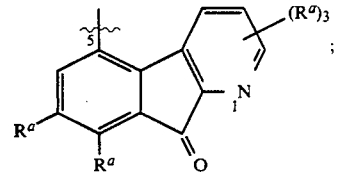
;

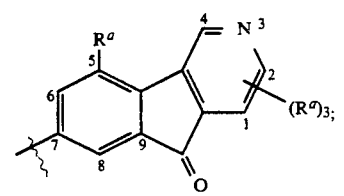
;

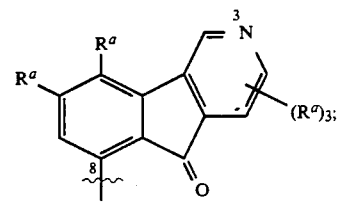

-continued c) 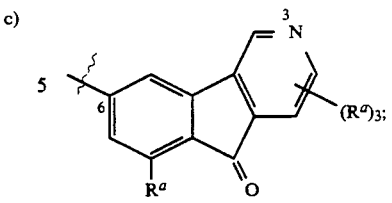
;

d) 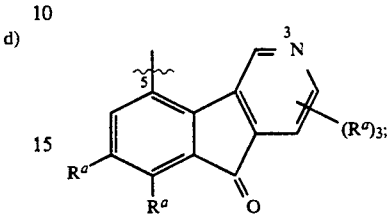
;

e) 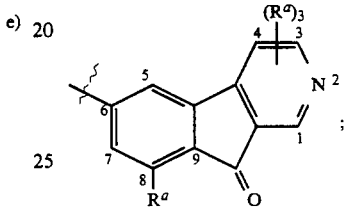
;

f) 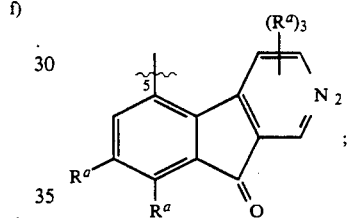
;

g) 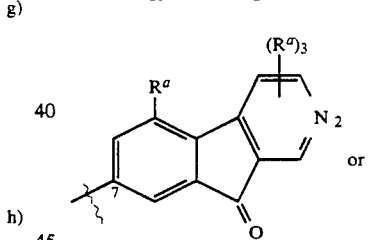
or h)

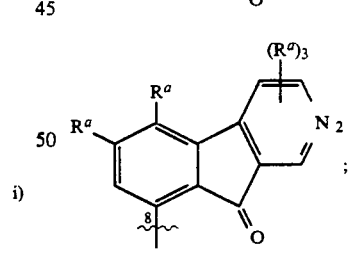
;

R is H or $CH_3$;

$R^1$ and $R^2$ are independently H, $CH_3$—, $CH_3CH_2$—, $(CH_3)_2CH$—, $HOCH_2$—, $CH_3CH(OH)$—, $(CH_3)_2C(OH)$—, $FCH_2CH(OH)$—, $F_2CHCH(OH)$—, $F_3CCH(OH)$—, $CH_3CH(F)$—, $CH_3CF_2$—, or $(CH_3)_3C(F)$—;

$R^a$ are independently selected from the radicals set out below, provided that no more than four $R^a$ substituents are other than hydrogen;

a) hydrogen;
b) a trifluoromethyl group: —$CF_3$;
c) a halogen atom: —Br, —Cl, —F, or —I;

d) $C_1$–$C_4$ alkoxy radical: —$OC_{1-4}$ alkyl, wherein the alkyl is optionally mono-substituted by $R^q$, where $R^q$ is a member selected from the group consisting of —OH, —$OCH_3$, —CN, —$C(O)NH_2$, —OC-$(O)NH_2$, —CHO, —$OC(O)N(CH_3)_2$, —$SO_2NH_2$, —$SO_2N(CH_3)_2$, —$SOCH_3$, —$SO_2CH_3$, —F, —$CF_3$, —$COOM^a$, (where $M^a$ is hydrogen, alkali metal, methyl or phenyl), tetrazolyl (where the point of attachment is the carbon atom of the tetrazole ring and one of the nitrogen atoms is mono-substituted by $M^a$ as defined above) and —$SO_3M^b$ (where $M^b$ is hydrogen or an alkali metal);

e) a hydroxy group: —OH;

f) a carbonyloxy radical of formula —$O(C=O)R^s$, where $R^s$ is $C_1$–$C_4$ alkyl or phenyl, each of which is optionally mono-substituted by $R^q$ as defined above;

g) a carbamoyloxy radical of formula —$O(C=O)N(R^y)R^z$ where $R^y$ and $R^z$ are independently H, $C_{1-4}$ alkyl (optionally mono-substituted by $R^q$ as defined above), together a 3- to 5-membered alkylidene radical to form a ring (optionally substituted with $R^q$ as defined above) or together form a 2- to 4-membered alkylidene radical, interrupted by —O—, —S—, —S(O)— or —$S(O)_2$— to form a ring (where the ring is optionally mono-substituted with $R^q$ as defined above);

h) a sulfur radical: —$S(O)_n$—$R^s$ where n=0-2, and $R^s$ is defined above;

i) a sulfamoyl group; —$SO_2N(R^y)R^z$ where $R^y$ and $R^z$ are as defined above;

j) azido: $N_3$;

k) a formamido group: —$N(R^t)(C=O)H$, where $R^t$ is H or $C_{1-4}$ alkyl, and the alkyl thereof is optionally mono-substituted by $R^q$ as defined above;

l) a ($C_1$–$C_4$ alkyl)carbonylamino radical: —$N(R^t)(C=O)C_{1-4}$ alkyl, where $R^t$ is as defined above, and the alkyl group is also optionally mono-substituted by $R^q$ as defined above;

m) a ($C_1$–$C_4$ alkoxy)carbonylamino radical: —$N(R^t)(C=O)OC_{1-4}$ alkyl, where $R^t$ is as defined above, and the alkyl group is also optionally mono-substituted by $R^q$ as defined above;

n) a ureido group: —$N(R^t)(C=O)N(R^y)R^z$ where $R^t$, $R^y$ and $R^z$ are as defined above;

o) a sulfonamido group: —$N(R^t)SO_2R^s$, where $R^s$ and $R^t$ are as defined above;

p) a cyano group: —CN;

q) a formyl or acetalized formyl radical: —(C=O)H or —$CH(OCH_3)_2$;

r) ($C_1$–$C_4$ alkyl)carbonyl radical wherein the carbonyl is acetalized: —$C(OCH_3)_2C_{1-4}$ alkyl, where the alkyl is optionally mono-substituted by $R^q$ as defined above;

s) carbonyl radical: —(C=O)$R^s$, where $R^s$ is as defined above;

t) a hydroximinomethyl radical in which the oxygen or carbon atom is optionally substituted by a $C_1$–$C_4$ alkyl group: —(C=$NOR^z$)$R^y$ where $R^y$ and $R^z$ are as defined above, except they may not be joined together to form a ring;

u) a ($C_1$–$C_4$ alkoxy)carbonyl radical: —(C=O)$OC_{1-4}$ alkyl, where the alkyl is optionally mono-substituted by $R^q$ as defined above;

v) a carbamyl radical: —(C=O)$N(R^y)R^z$ where $R^y$ and $R^z$ are defined above;

w) an N-hydroxycarbamoyl or N($C_{1-4}$ alkoxy)carbamoyl radical in which the nitrogen atom may be additionally substituted by a $C_1$–$C_4$ alkyl group: —(C=O)—$N(OR^y)R^z$ where $R^y$ and $R^z$ are as defined above, except they may not be joined together to form a ring;

x) a thiocarbamoyl group: —(C=S)$N(R^y)R^z$ where $R^y$ and $R^z$ are as defined above;

y) carboxyl: —$COOM^b$, where $M^b$ is as defined above;

z) thiocyanate: —SCN;

aa) trifluoromethylthio: —$SCF_3$;

ab) tetrazolyl, where the point of attachment is the carbon atom of the tetrazole ring and one of the nitrogen atoms is mono-substituted by hydrogen, an alkali metal or a $C_1$–$C_4$ alkyl optionally substituted by $R^q$ as defined above;

ac) an anionic function selected from the group consisting of:
phosphono [P=O$(OM^b)_2$;
alkylphosphono {P=O$(OM^b)$-[O($C_1$–$C_4$ alkyl)]};
alkylphosphinyl [P=O$(OM^b)$-($C_1$–$C_4$ alkyl)];
phosphoramido [P=O$(OM^b)N(R^y)R^z$ and P=O$(OM^b)NHR^x$];
sulfino ($SO_2M^b$);
sulfo ($SO_3M^b$);
acylsulfonamides selected from the structures $CONM^bSO_2R^x$, $CONM^bSO_2N(R^y)R^z$, $SO_2NM^bCON(R^y)R^z$; and $SO_2NM^bCN$, where $R^x$ is phenyl or heteroaryl, where heteroaryl is a monocyclic aromatic hydrocarbon group having 5 or 6 ring atoms, in which a carbon atom is the point of attachment, in which one of the carbon atoms has been replaced by a nitrogen atom, in which one additional carbon atom is optionally replaced by a heteroatom selected from O or S, and in which from 1 to 2 additional carbon atoms are optionally replaced by a nitrogen heteroatom, and where the phenyl and heteroaryl are optionally mono-substituted by $R^q$, as defined above; $M^b$ is as defined above; and $R^y$ and $R^z$ are as defined above;

ad) $C_5$–$C_7$ cycloalkyl group in which one of the carbon atoms in the ring is replaced by a heteroatom selected from O, S, NH, or N($C_1$–$C_4$ alkyl) and in which one additional carbon may be replaced by NH or N($C_1$–$C_4$ alkyl), and in which at least one carbon atom adjacent to each nitrogen heteroatom has both of its attached hydrogen atoms replaced by one oxygen thus forming a carbonyl moiety and there are one or two carbonyl moieties present in the ring;

ae) $C_2$–$C_4$ alkenyl radical, optionally mono-substituted by one of the substituents b) to ad) above and phenyl which is optionally substituted by $R^q$ as defined above;

af) $C_2$–$C_4$ alkynyl radical, optionally mono-substituted by one of the substituents b) to ad) above;

ag) $C_1$–$C_4$ alkyl radical;

ah) $C_1$–$C_4$ alkyl mono-substituted by one of the substituents b)-ad) above; or ai) a 2-oxazolidinonyl moiety in which the point of attachment is the nitrogen atom of the oxazolidinone ring, the ring oxygen atom is optionally replaced by a heteroatom selected from S and $NR^t$ (where $R^t$ is as defined above) and one of the saturated carbon atoms of the oxazolidinone ring is optionally mono-substituted by one of the substituents b) to ah) above;

M is:
i) hydrogen;
ii) a pharmaceutically acceptable esterifying group or removable carboxyl protecting group; or
iii) an alkali metal or other pharmaceutically acceptable cation.

DETAILED DESCRIPTION OF THE INVENTION

The manufacture of compounds of Formula I may be carried out in a three-stage synthesis scheme followed by removal of protecting groups. The objective of the first synthesis stage is to produce a base azafluoren-9-one compound which may be converted to the two-position substituent of the carbapenem of Formula I. The objective of the second synthesis stage is to substitute the azafluoren-9-one with the desired $R^a$. The objective of the third synthesis stage is to attach the base azafluoren-9-one to the carbapenem. This third synthesis stage may be performed after the first synthesis stage or after the second synthesis stage according to the nature of the various $R^a$ substituents.

Schemes A, B, C, D, E and F demonstrate suggested first stage syntheses. Scheme K demonstrates the third stage syntheses. The second stage synthesis varies according to the selected $R^a$ group and suggested methods are shown in Schemes H–J.

The synthesis of the 5-, 6-, 7- or 8-substituted azafluoroenones are described in the schemes below (Schemes A, B and C). The general route involves the preparation of a suitably substituted phenylpyridine which contains the carboxylic acid group needed for the ring closure to generate the desired azafluoren-9-one ring system, as well as other functional groups for further elaboration to the desired azafluoren-9-one and the functionality needed for coupling to the carbapenem.

The syntheses of the unsubstituted and substituted 1-, 2-, 3- or 4-azafluoren-9-ones are described in the schemes below (Schemes A, B, C, D, E, F and G). The general route involves the preparation of a suitable substituted phenylpyridine which contains the carboxylic acid group needed for the ring closure to generate the desired azafluoren-9-one ring system, as well as other functional groups for further elaboration to the desired azafluoren-9-one and the functionality needed for coupling to the carbapenem.

SCHEME A

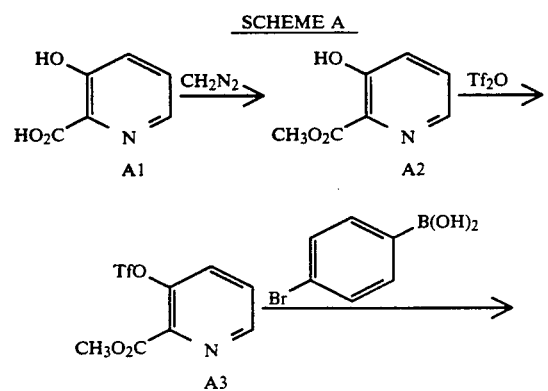

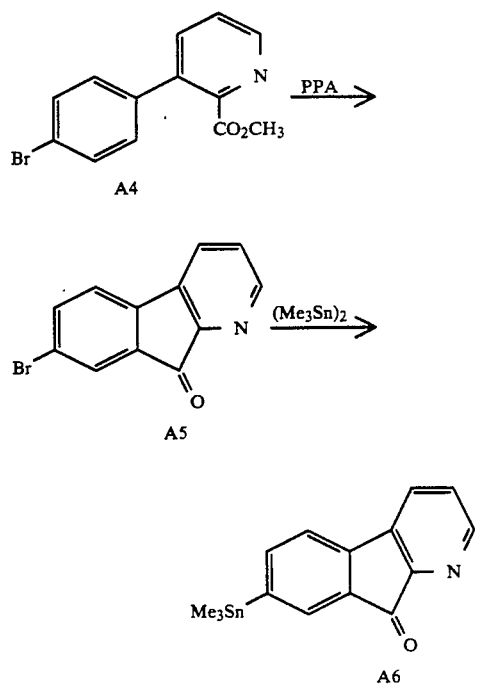

Tf$_2$O = triflic anhydride
PPA = polyphosphoric acid

SCHEME B

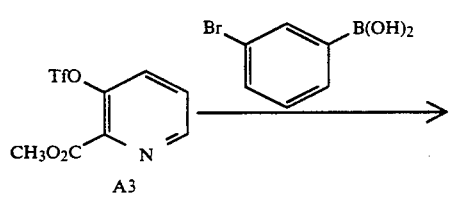

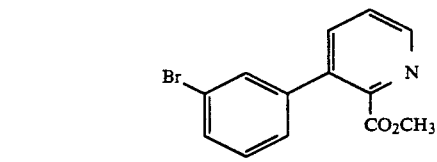

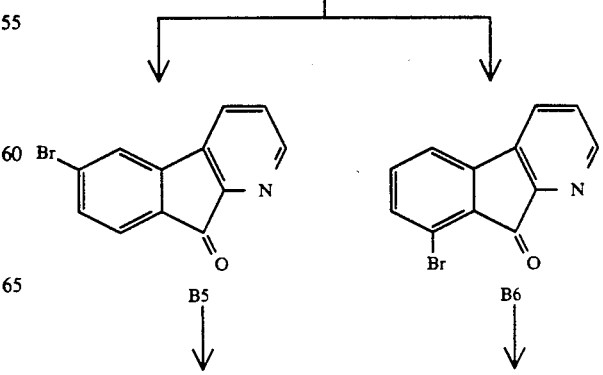

-continued
SCHEME B
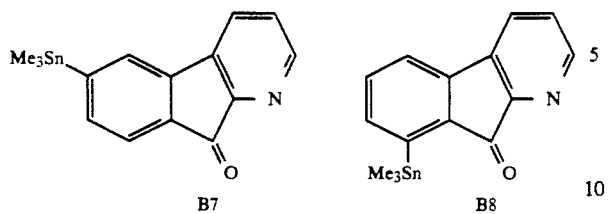
-continued
SCHEME C
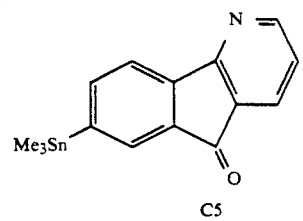
SCHEME C
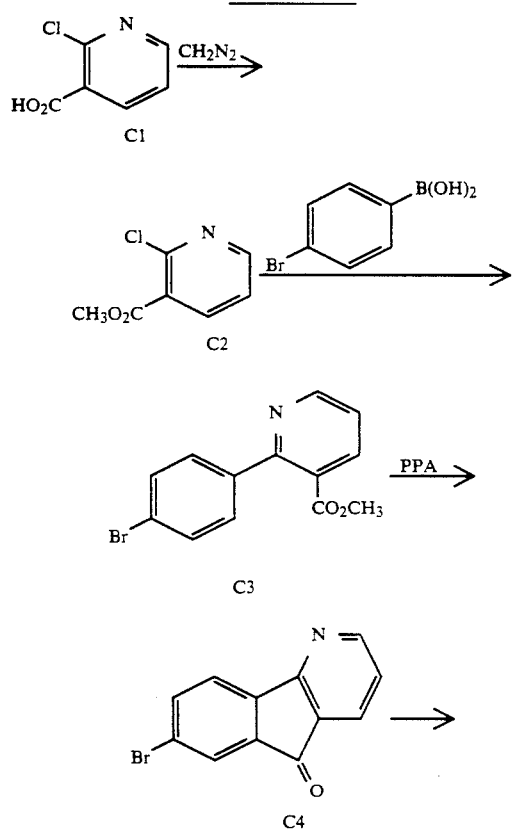
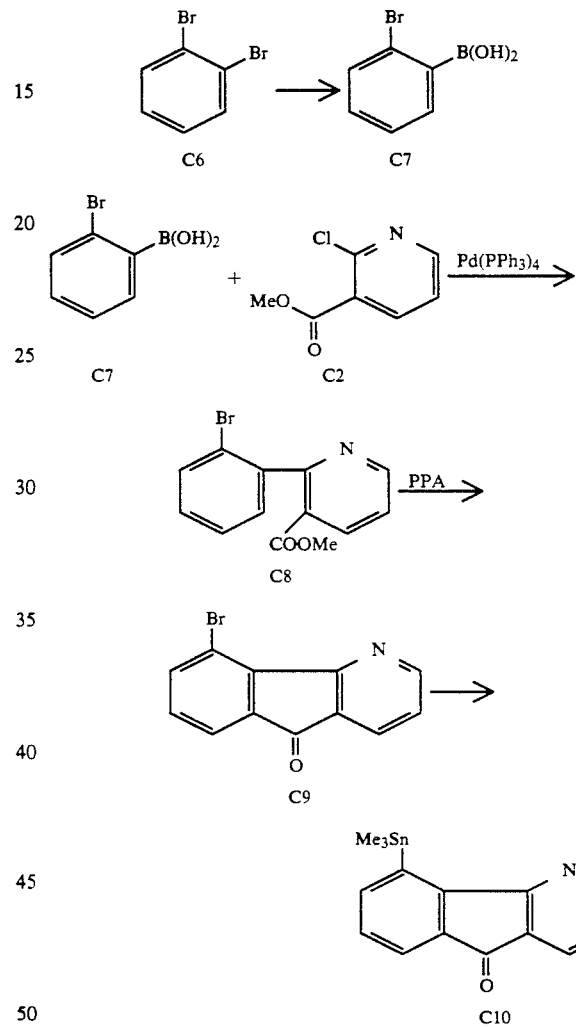
SCHEME D
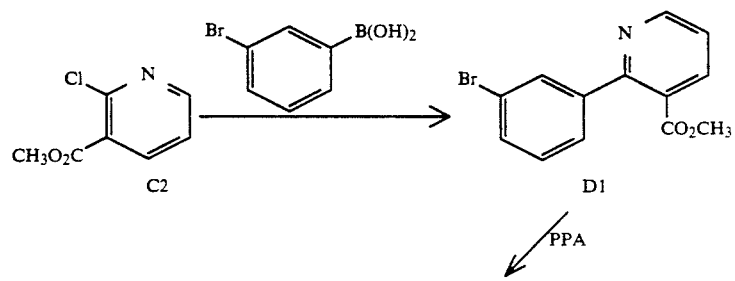

SCHEME D
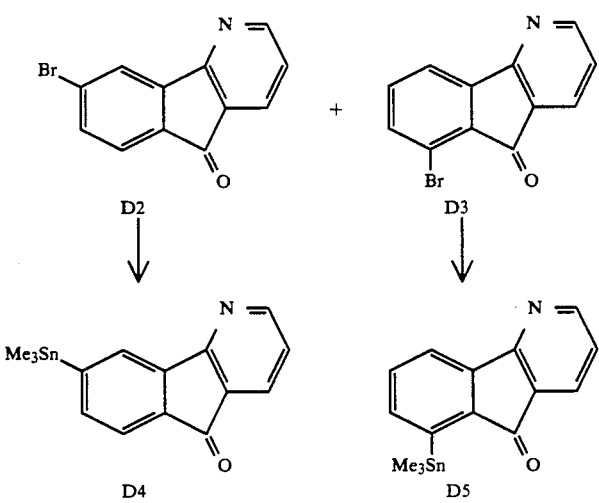
SCHEME E
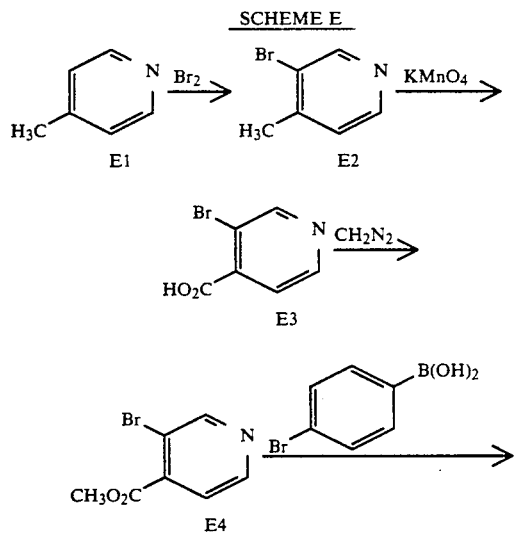
-continued
SCHEME E
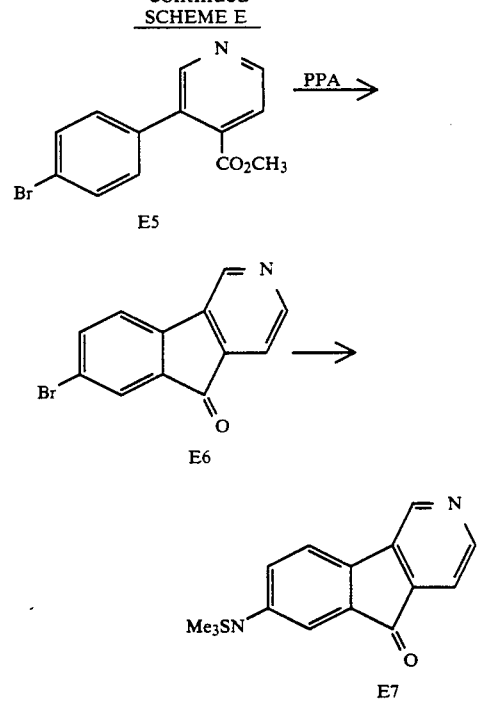
SCHEME F
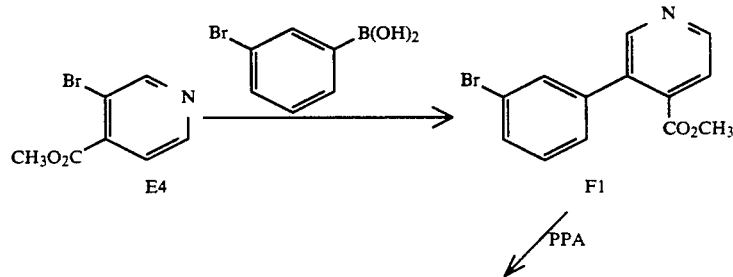

SCHEME F
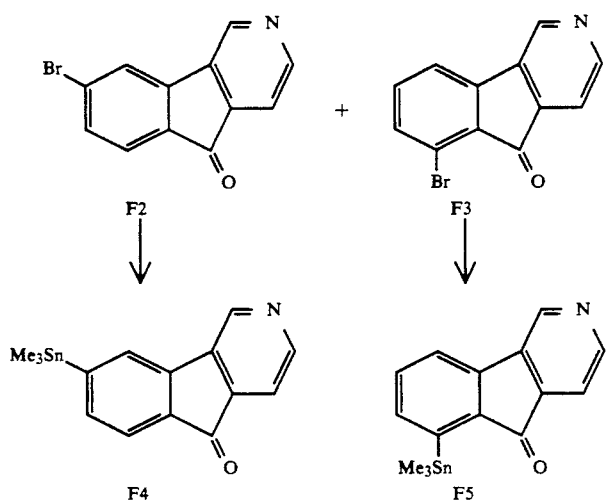
SCHEME G
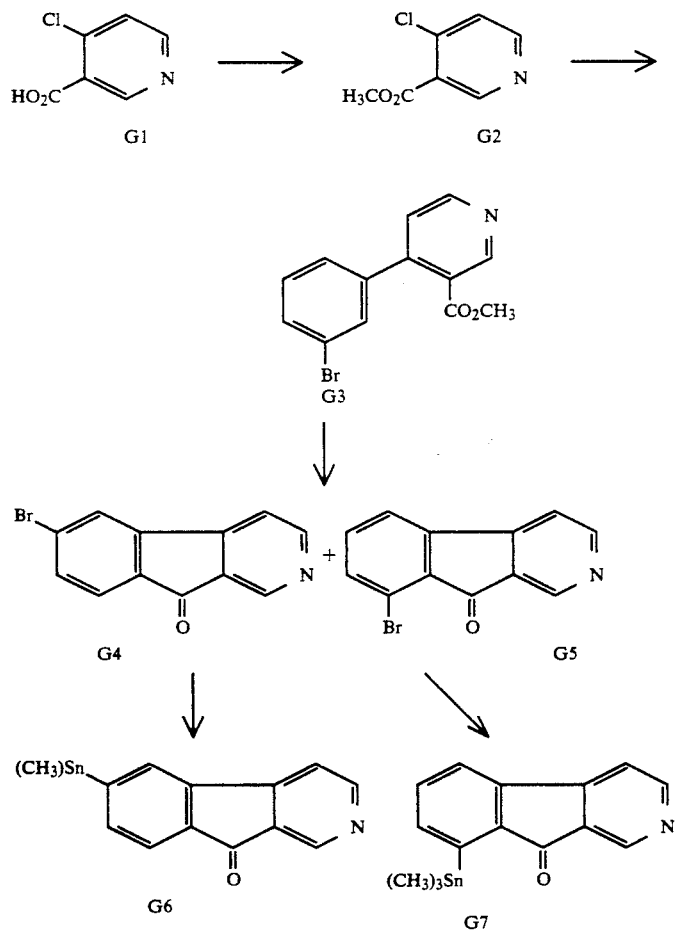

15
SCHEME H
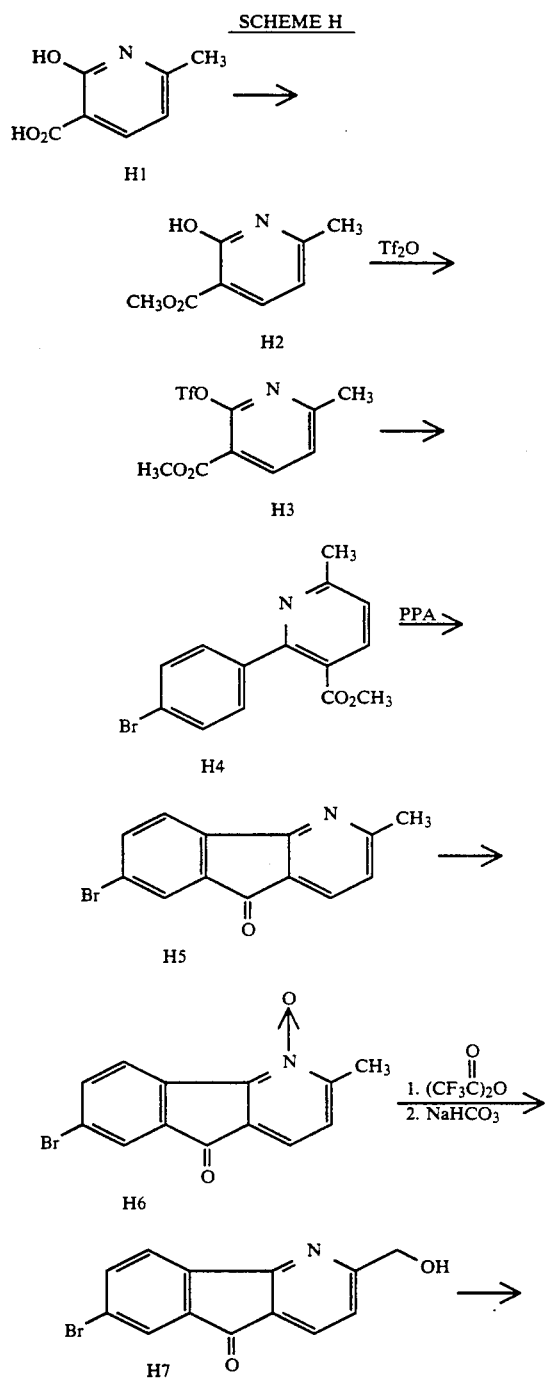
16
-continued
SCHEME H
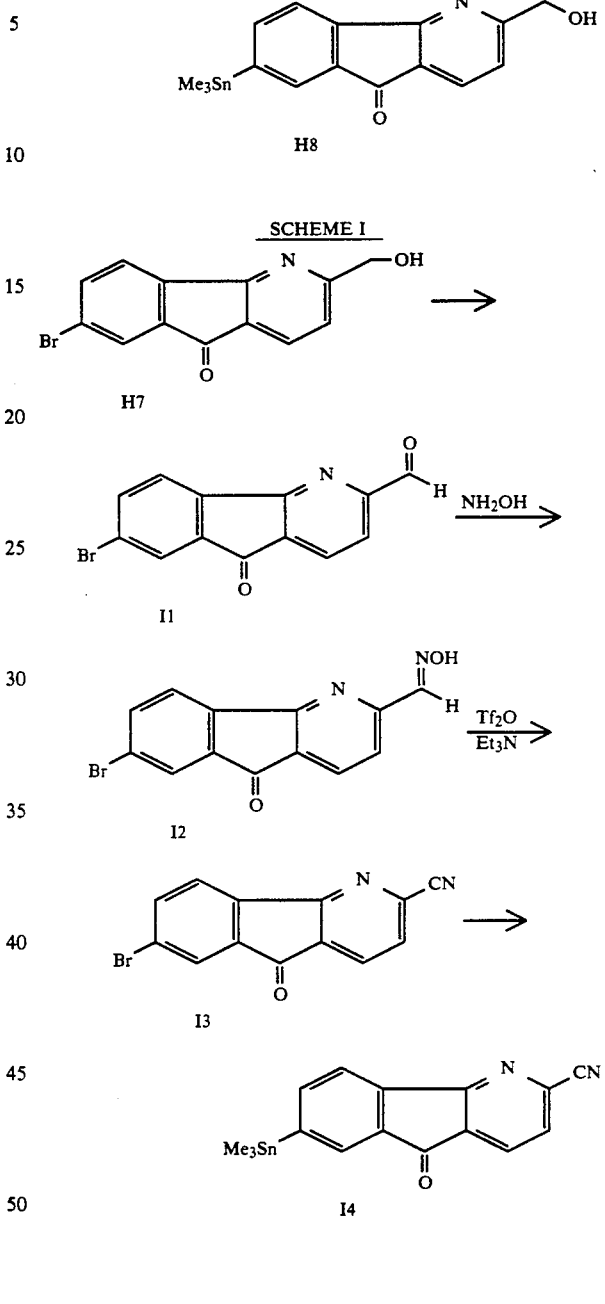
SCHEME J
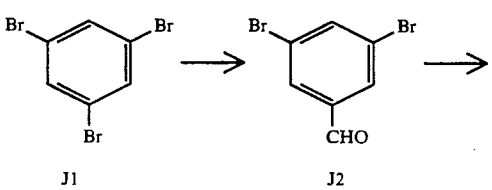

SCHEME J
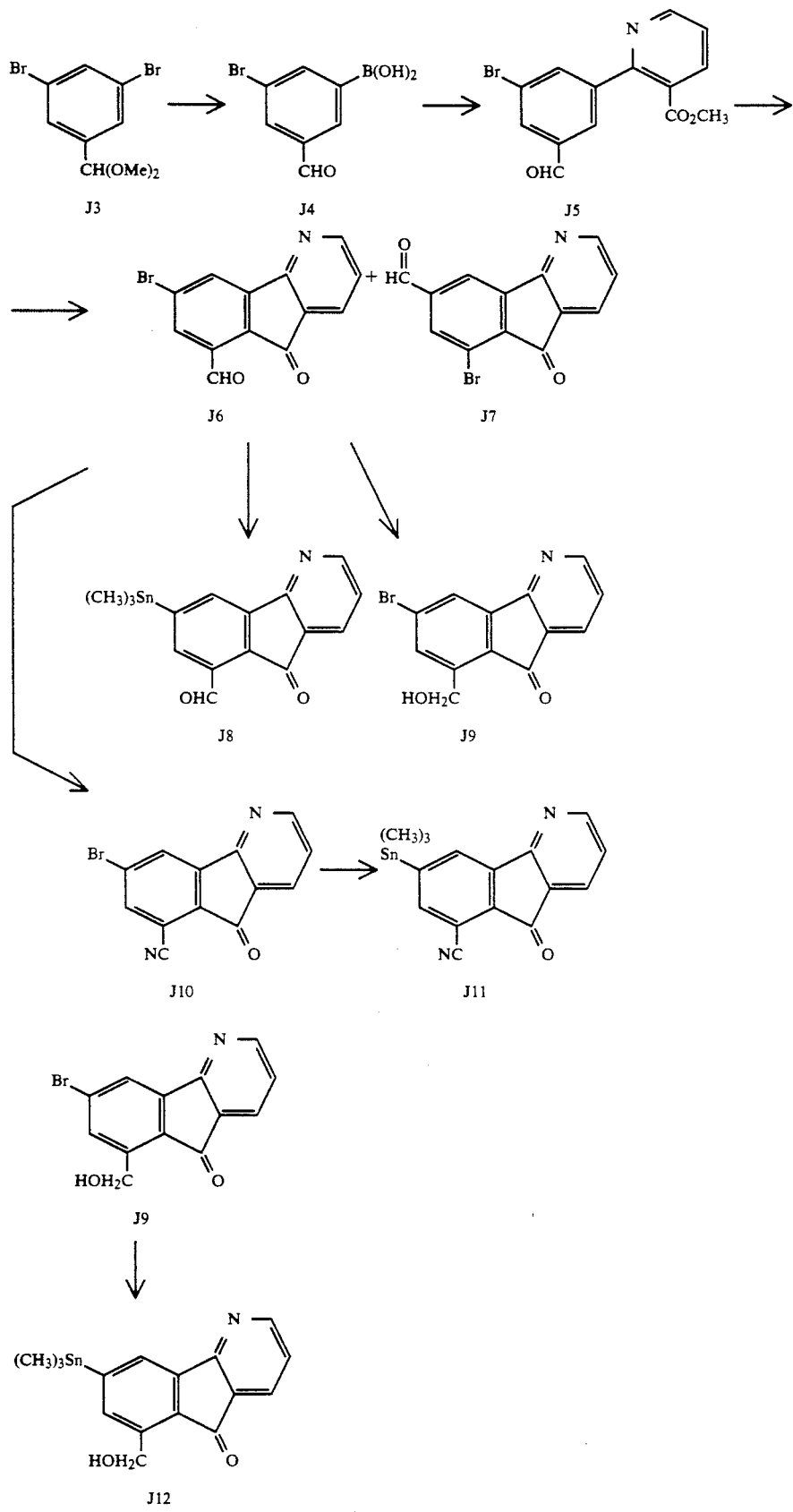

SCHEME K
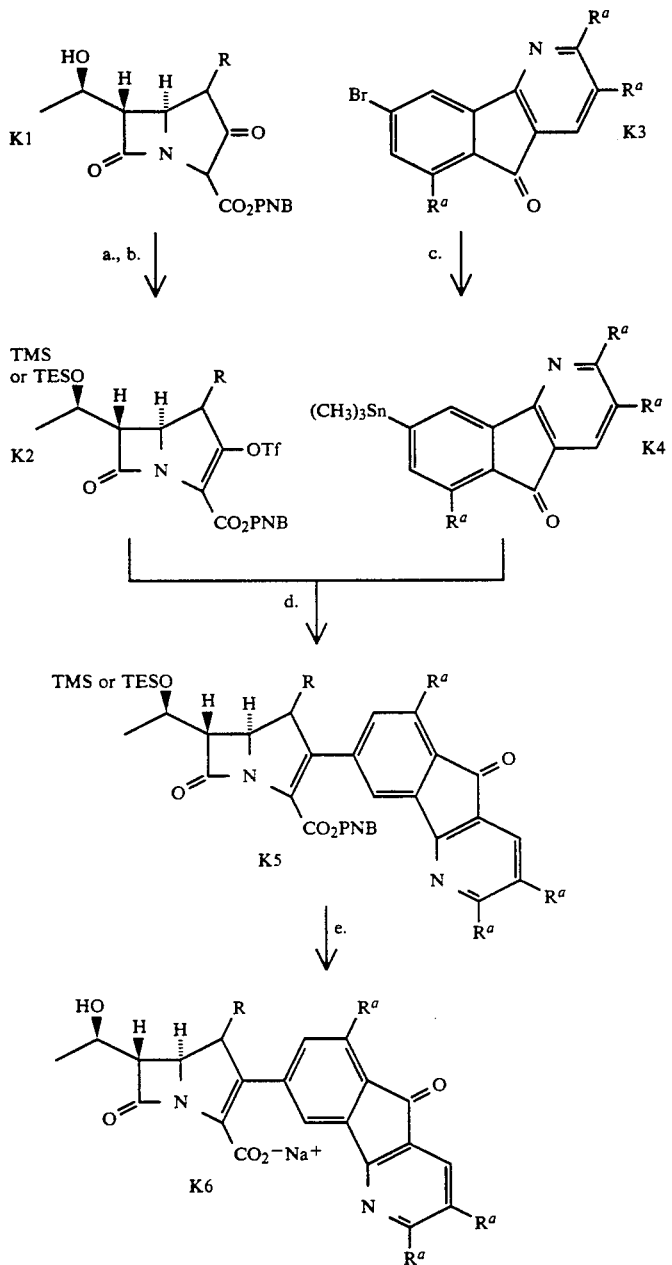
TMS = trimethylsilyl
TESO = triethylsilyloxy
PNB = p-nitrobenzyl
a. Tf$_2$O, DIPA, THF, −78° C.
b. (CH$_3$)$_3$SiOSO$_2$CF$_3$ or (CH$_3$CH$_2$)$_3$SiOSO$_2$CF$_3$
c. (Me$_3$Sn)$_2$, (C$_6$H$_5$)$_3$P, [(C$_6$H$_5$)$_3$P]$_4$Pd$^0$
d. Pd$_2$(dba)$_3$·CHCl$_3$, ZnCl$_2$, 2-pyrrolidinone, HF.
e. 1) H$^+$, 2) H$_2$, Pd/C.
DIPA = diisopropylamine
THF = tetrahydrofuran

SCHEME L

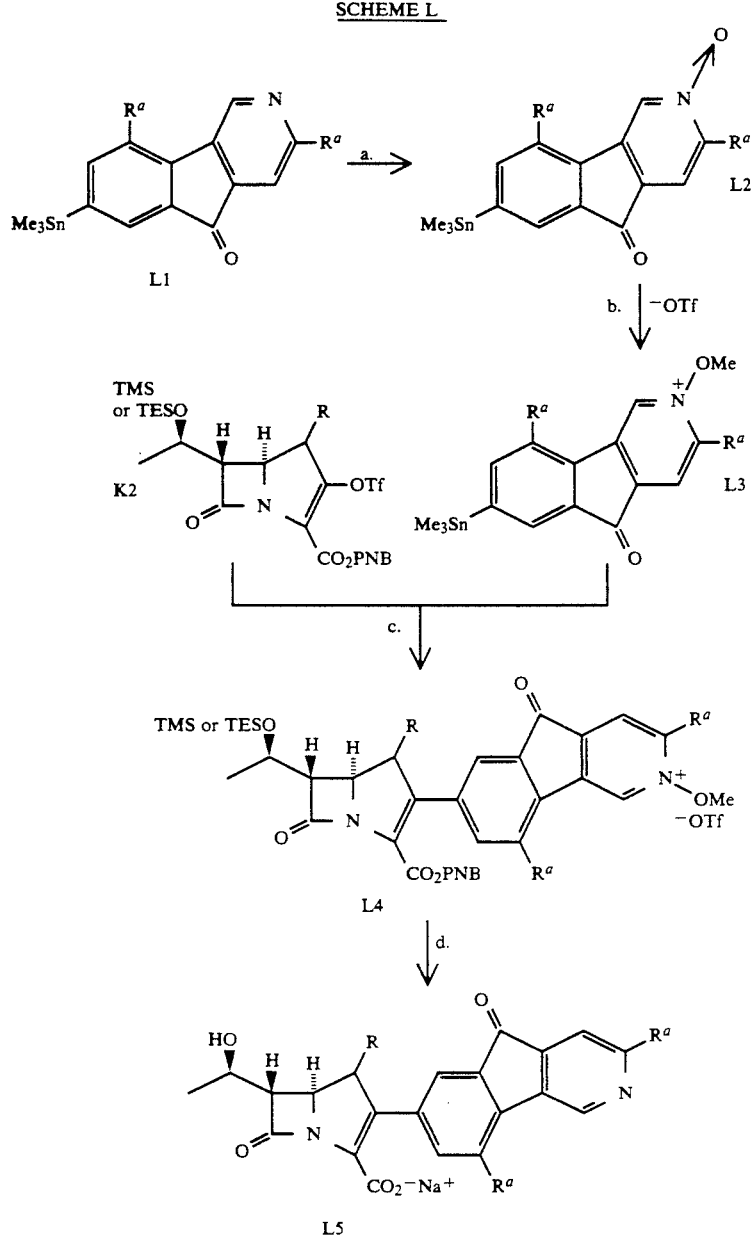

a. mCPBA, NaHCO₃, CH₂Cl₂
b. CH₃OSO₂CF₃
c. Pd₂(dba)₃·CHCl₃, ZnCl₂, 2-pyrrolidinone, THF.
d. 1) H⁺, 2) H₂, Pd/C.

The desired azafluoroenone, produced in the first or second synthetic stage, is attached to the carbapenem in the third stage by direct coupling to a carbapenem triflate. Scheme K describes this direct coupling to the carbapenem.

Scheme K illustrates the third stage synthesis, i.e. attachment of the base azafluorenone to the 2-position of the carbapenem for one of the azafluorenone regioisomers, specifically a 4-aza-9-fluorenone. However this synthetic scheme has general applicability for all of the regioisomers. This synthesis involves a palladium catalyzed cross-coupling reaction between a carbapenem triflate and a suitably substituted arylstannane, a process which is described in U.S. patent application Ser. No. 485,096 filed Feb. 26, 1990. In order to apply this synthesis, it is first necessary to modify the bromoazafluoren-9-one (e.g. K3) to the trimethylstannylazafluoren-9-one (e.g. K4). This is accomplished by reacting the bromo compound, hexamethylditin, tetrakis(triphenylphosphine) palladium(0) and triphenylphosphine in toluene at 110° C. or more. Referring to Scheme K, the 2-oxocarbapenam K1 is reacted with a suitable trifluoromethanesulfonyl source, such as trifluoromethanesulfonic anhydride, trifluoromethanesulfonyl chloride and the like, in the presence of an organic nitrogen base, such as triethylamine, diisopropylamine and the like, in a polar aprotic solvent, such as tetrahydrofuran. An organic nitrogen base, such as triethylamine and the like, is then added to the reaction solution followed immediately by a silylating agent, such as trimethylsilyl or triethylsilyl trifluoromethanesulfonate to provide the triflate intermediate K2. An aprotic polar coordinating solvent, such as dimethylformamide ("DMF"), 1-methyl-2-pyrrolidinone and the like, is added. This is followed by the addition of a palladium compound, such as tris(dibenzylidene-acetone)dipalladium-chloroform, palladium acetate and the like, optionally a suitably substituted phenylphosphine, such as tris(4-methoxyphenyl)phosphine, tris(2,4,6-trimethoxyphenyl)phosphine and the like, and the stannane K4. A metal halide, such as lithium chloride, zinc chloride and the like, is added and the reaction solution is warmed to a suitable temperature, such as 0° C. to 50° C., and allowed to stir for a suitable amount of time such as from a few minutes to 48 hours. The carbapenem K5 is obtained by conventional isolation/purification methodology known in the art.

The other corresponding azafluoren-9-one regioisomers of K5 can be prepared analogously by starting with the bromoazafluoren-9-one corresponding to K3, which in turn is derived from appropriately substituted phenylpyridines by following the steps outlined in Schemes A, B, C, D, E, F, G, H, I, and J.

Generally speaking, the mild conditions of the synthesis shown in Scheme K allow for a wide range of functional groups $R^a$ to be present when attaching the azafluoren-9-one. However, in certain cases it is advantageous for the $R^a$ substituent(s) of the stannane K4 to be introduced in a protected or precursory form. Final elaboration of $R^a$ from a precursor substituent, e.g. hydroxymethyl, may be accomplished on carbapenem intermediate K5. Removal of protecting groups then provides the final compound of Formula I. Such final elaboration and deprotection is described further below.

Scheme L provides an alternative synthesis of the compounds of the instant invention. If it is found that one of the regioisomeric azafluorenone stannanes is incompatible with the coupling procedure illustrated in Scheme K, the nitrogen of the azafluorenone may first be protected with a N-methoxy moiety and, following coupling to the carbapenem nucleus, the N-protecting group is subsequently removed under the deprotection conditions. Such an alternative synthesis may be compatible with the preparation of any of the regioisomeric azafluorenonylcarbapenems.

The steps for preparing the 2-oxocarbapenam intermediate, K1, are well known in the art and are explained in ample detail by D. G. Melillo, et al., *Tetrahedron Letters*, 21, 2783 (1980), T. Salzmann et al., *J. Am. Chem. Soc.*, 102, 6161 (1980), and L. M. Fuentes, I. Shinkai, and T. N. Salzmann, *J. Am. Chem. Soc.*, 108, 4675 (1986). The syntheses are also disclosed in U.S. Pat. No. 4,269,772, U.S. Pat. No. 4,350,631, U.S. Pat. No. 4,383,946 and U.S. Pat. No. 4,414,155 all assigned to Merck and Co., Inc.

The general synthesis description depicted above in the schemes shows a protected 1-hydroxyethyl substitution on the 6-position of the carbapenem. After final deprotection, a 1-hydroxyethyl substituent is obtained, which is preferred in most cases. However, it has been found that with certain 2-side-chain selections, the ultimate balance of favorable properties in the overall molecule may be enhanced by selection of the 6-(1-fluoroethyl) moiety instead. Preparation of 6-fluoroalkyl compounds within the scope of the present invention is carried out in a straightforward manner using techniques well known in the art of preparing carbapenem antibacterial compounds. See, e.g., J. G. deVries et al., *Heterocycles*, 23 (8), 1915 (1985); BE 900 718 A (Sandoz) and Japanese Patent Pub. No. 6-0163-882-A (Sanraku Ocean).

In the compounds of the present invention, the $R^a$ substituents are either neutral or anionic in nature, and are distinguishable from cationic substituents chemically and with respect to the biological properties which they confer. In related compounds, it has been found that the neutral or anionic substituted compounds afford greater water solubility and reduced potential for CNS side effects. Substituents which tend to confer improved water solubility on the overall compound have been found useful, since they are contemplated to thereby improve the transport of the compound involved. Although a substantial number and range of neutral and anionic substituents have been described herein, all of these are contemplated to be a part of the present invention based on the biological performance of substituents related in terms of their medicinal chemistry.

The compounds of the present invention, may contain more than one neutral or anionic substituent, with this substitution pattern there can be a combination of desired attributes in the final overall molecule not attainable with a single substituent, i.e., improved anti-MRSA/MRCNS activity together with enhanced water solubility.

In preferred compounds of Formula I, $R^1$ is hydrogen. More preferably $R^1$ is hydrogen and $R^2$ is (R)—CH$_3$CH(OH)— or (R)—CH$_3$CH(F)—. Most preferably $R^1$ is hydrogen and $R^2$ is (R)—CH$_3$CH(OH)—. While R=hydrogen is usually preferred, there are instances in which R=CH$_3$ may provide improved chemical stability, water solubility, or pharmacokinetic behavior. The substituent R=CH$_3$ may be of either configuration, i.e., the $\alpha$ or $\beta$-stereoisomer. Additionally, in preferred compounds of Formula I, in total, up to two $R^a$ substituents of the azafluoren-9-one are other than hydrogen.

Embodiments of the instant invention are compounds wherein Y is 4-azafluoren-9-one and the attachment point where the carbapenem is attached to the azafluorenone is at the 6- or 7-position of the azafluorenone.

Among preferred $R^a$ are hydrogen, (C$_1$-C$_4$)alkyl mono-substituted with hydroxy, such as, hydroxymethyl; formyl; halogen; carbamoyl, such as, —CONH$_2$; hydroximinomethyl, such as, —CH=NOH; —S(O)$_x$alkyl (wherein x is 0 to 2), such as —SCH$_3$; —SOCH$_2$CH$_2$OH; or cyano.

In regard to the preferred substituents, the hydroxymethyl may be obtained on the azafluoren-9-one as shown generally in Schemes H and J. The formyl-substituted azafluorenon-9-one J6 and the isomeric methyl-azafluoren-9-ones H5 serve as precursor starting materials in Schemes J and H respectively. Thus, proceeding as shown in Schemes H and J but using appropriate pyridines the isomeric hydroxymethyl-substituted azafluoren-9-ones may be produced.

Specifically referring to Scheme H, utilizing an appropriately substituted o-methyl pyridine, such as 2-hydroxy-6-methylpyridine 3-carboxylic acid and the like, a methyl azafluorenone, such as compound H5, may be obtained utilizing the procedure illustrated in Schemes A-G. The pyridine nitrogen is then oxidized with a suitable oxidizing agent, such as m-chloroperbenzoic acid, MMPP, and the like, to provide the azafluorenone N-oxide H6 which is acylated and undergoes rearrangement to provide the hydroxymethyl moiety ortho to the nitrogen of the ring.

Scheme J illustrates preparation of azafluorenones having a non-hydrogen $R^a$ substituent in the aromatic ring which will be directly connected to the carbapenem nucleus. Specifically, the Grignard reagent of 1,3,5-tribromobenzene is reacted with dimethylformamide to form the 3,5-dibromo benzaldehyde J2. The aldehyde is protected and one of the bromines is converted to a boronic acid. Palladium mediated coupling followed by cyclization provides a mixture of the azafluorenones J6 and J7. The trimethylstannyl azafluorenone J8 may be formed and subsequently coupled to the carbapenem nucleus. Alternatively, the formyl moiety may be converted into other substituents as described hereinbelow. Specifically with regard to conversion of the formyl moiety to the hydroxymethyl moiety, treatment of the azafluorenone J6 with a suitable reducing agent, such as: sodium borohydride and the like provides the 9-hydroxymethyl-4-azafluorenone J9.

Proceeding according to Scheme K, and employing H7 or isomeric J9 as starting material K3, the corresponding hydroxymethyl substituted K5 may be obtained.

Alternatively, elaboration of the hydroxymethyl group into another preferred $R^a$ substituent as described below may be carried-out prior to coupling of the azafluoren-9-one to the carbapenem. In certain instances, depending on the particular $R^a$ group being sought, such elaboration may also be performed on K5 after attachment of the fluoren-9-one side chain to the carbapenem. As previously described, the corresponding 2-azafluoren-9-one regioisomers of K5 may be prepared analogously by starting with the 2-bromoazafluoren-9-ones corresponding to E4 and isomeric H3, which in turn may be derived by employing the appropriate starting materials in Schemes H and J.

The preferred formyl substitution on the azafluoren-9-one may be obtained from the hydroxymethyl substitution just described by a Swern oxidation as illustrated in Scheme I. For example, H7 (or J9) is oxidized in methylene chloride at from −70° C. to room temperature employing oxalyl chloride-dimethyl sulfoxide, followed by triethylamine (Scheme I). Alternatively, this oxidation may be conveniently carried-out with N-methylmorpholine-N-oxide and a catalytic amount of tetra-n-propylammonium perruthenate in methylene chloride at room temperature. Obviously, the position of the resultant formyl substitution will depend upon the position of the hydroxymethyl substitution.

The preferred —CH=NOH substitution on the azafluoren-9-one may be conveniently obtained from the formyl substitution just described. This is accomplished simply by exposing the formyl substituted compound to hydroxylamine in an appropriate solvent at room temperature (Scheme I).

The preferred cyano substitution on the fluoren-9-one may be obtained from the —CH=NOH substitution just described. The —CH=NOH substituted compound is dehydrated with triflic anhydride and triethylamine in a solvent at −70° C. (Scheme I).

A —COOK substitution on the azafluoren-9-one, and subsequently the corresponding ester, may be obtained from the hydroxymethyl substituted H7 or J9 described above. For example, H7 is oxidized with Jones reagent to convert the hydroxymethyl substituent into a carboxylic acid group. The oxidation with Jones reagent may be incompatible with the carbapenem and thus is optimally performed prior to coupling with the carbapenem. An alternative procedure involves the oxidation of a methyl by dibromination, acetolysis, hydrolysis and finally Jones oxidation to the acid. Prior to coupling with the carbapenem, the carboxy is advantageously protected as its p-nitrobenzyl or allyl ester. Protection is carried out by alkylating with p-nitrobenzyl or allyl bromide and triethylamine, in dimethylformamide. Deprotection of the allyl ester following coupling is carried out by palladium catalyzed deallylation in a solution containing potassium 2-ethylhexanoate, while the p-nitrobenzyl ester can be removed by hydrogenation over palladium on carbon in presence of potassium bicarbonate. Deprotection in such a manner yields the desired potassium salt.

The preferred carbamoyl substitution on the azafluoren-9-one may be obtained from H7 or J9 by oxidizing the hydroxymethyl with Jones reagent to the corresponding carboxylic acid as described above. This carboxy is converted to —CONH$_2$ by sequentially contacting with 1-ethyl-3-(3-dimethyl-aminopropyl)carbodiimide hydrochloride, 1-hydroxybenzotriazole, and ammonia in an organic solvent at room temperature. Alternatively, the carboxylic acid substituent may be reacted with 1,1′-carbonyldiimidazole in an aprotic polar solvent, such as tetrahydrofuran followed by treatment with aqueous ammonia to give the carboxamide. Substituted amides may of course be obtained by replacing ammonia with the corresponding substituted amine.

In addition to or including the above, preferred $R^a$ substituents include:

| | |
|---|---|
| —OCH$_3$ | —OCH$_2$CO$_2$CH$_3$ |
| —OCH$_2$CH$_2$OH | —CF$_3$ |
| —F | —Cl |
| —Br | —I |
| —OH | —OCOCH$_3$ |
| —OCONH$_2$ | —SCH$_3$ |
| —SOCH$_3$ | —SO$_2$CH$_3$ |
| —SCH$_2$CH$_2$OH | —SOCH$_2$CH$_2$OH |
| —SO$_2$NH$_2$ | —SO$_2$N(CH$_3$)$_2$ |
| —NHCHO | —NHCOCH$_3$ |
| —NHCO$_2$CH$_3$ | —NHSO$_2$CH$_3$ |
| —CN | —CHO |
| —COCH$_3$ | —COCH$_2$OH |
| —CH=NOH | —CH=NOCH$_3$ |
| —CH=NOCH$_2$CO$_2$CH$_3$ | —CH=NOCMe$_2$CO$_2$CH$_3$ |
| —CH=NOCMe$_2$CO$_2$Me | —CO$_2$CH$_2$CH$_2$OH |
| —CONH$_2$ | —CONHCH$_3$ |
| —CON(CH$_3$)$_2$ | —CONHCH$_2$CN |
| —CONHCH$_2$CONH$_2$ | —CONHCH$_2$CO$_2$CH$_3$ |
| —CONHOH | —CONHCH$_3$ |
| -tetrazolyl | —CO$_2$CH$_3$ |
| —SCF$_3$ | —PO$_3$CH$_3$H |
| —CONHSO$_2$Ph | —CONHSO$_2$NH$_2$ |
| —SO$_3$CH$_3$ | —SO$_2$NHCN |
| —SO$_2$NHCONH$_2$ | —CH=CHCN |
| —CH=CHCONH$_2$ | —CH=CHCO$_2$CH$_3$ |
| —C≡C—CONH$_2$ | —C≡C—CN |
| —CH$_2$OH | —CH$_2$N$_3$ |
| —CH$_2$CO$_2$CH$_3$ | —SO$_2$CH$_2$CH$_2$OH and |
| —CH$_2$I. | |

In the preparation methods described above, the carboxyl group at the 3-position and the hydroxyl group at the 8-position of the carbapenem remain blocked by protecting groups until the final product is prepared. Deblocking may be carried out in a conventional manner. Alternatively, for those prepared via Scheme K, deprotection is conducted sequentially. Thus, compound K5 is exposed initially to aqueous acidic conditions, acetic acid or dilute HCl or the like, in an organic solvent such as tetrahydrofuran at 0° C. to 50° C. for from a few minutes to several hours. The resulting desilylated carbapenem may be isolated by conventional techniques, but is more conveniently taken into the final deprotection process. Thus, addition of an inorganic base such as $NaHCO_3$ or $KHCO_3$ and 10% Pd/C followed by hydrogenation provides for the removal of the p-nitrobenzyl ester protecting group and the formation of the final compound of Formula I.

The overall molecule must be electronically balanced. It is within the scope of this invention to utilize an anionic substituent, in which case it will be understood that it is necessary to provide a second counterion (cation) for the anionic substituent. However, it is well within the skill of a medicinal chemist, to whom there is available many suitable cationic counterions, to make such choices.

With reference to the above definitions, "alkyl" means a straight or branched chain aliphatic hydrocarbon radical.

The term "heteroatom" means N, S, or O, selected on an independent basis.

The term "heteroaryl" has been defined herein, in relation to the $R^x$ group, to have a specific and limited meaning, being only monocyclic. It is required that the monocyclic heteroaryl have at least one nitrogen atom, and optionally at most only two additional oxygen or sulfur heteroatoms may be present. Heteroaryls of this type are pyrrole and pyridine (one N); and oxazole, thiazole or oxazine (one N and one O or one S). While additional nitrogen atoms may be present together with the first nitrogen and oxygen or sulfur, giving, e.g., a thiadiazole (two N's and one S), the preferred heteroaryls are those where only nitrogen heteroatoms are present when there is more than one. Typical of these are pyrazole, imidazole, pyrimidine and pyrazine (two N's) and triazine (three N's). The heteroaryl group of $R^x$ is always optionally mono-substituted by $R^q$, defined above, and substitution can be on one of the carbon atoms or one of the heteroatoms, although in the latter case certain substituent choices may not be appropriate.

It is understood that an $R^a$ substituent attached at one position on the azafluorenone moiety may be different from other $R^a$ substituents attached to the same azafluorenone moiety. Thus, for example, $R^a$ at the 2-position may be a cyano group while the remaining $R^a$'s on a azafluorenone moiety may be hydrogens.

Listed in Tables I and II are specific compounds illustrative of the instant invention. It is understood that the stereochemistry of $R^2$ substituents which contain a chiral center (1-fluoroethyl or 1-hydroxyethyl) is the (R)-configuration in all of the listed compounds. The substituent $R^a$ when it is not hydrogen (designated as $R^{a'}$) and the substituents R, $R^1$, $R^2$ and M are as defined in the Tables below. Table I lists compounds wherein the attachment of the carbapenem nucleus to the azafluorenone moiety is at the 7-position of the azafluorenone. Analogous compounds having the point of attachment at other positions of the azafluorenone are listed in Table II. Reference may be made to the structures on pages 6 to 11 hereinabove to understand what a particular position number on the azafluorenone moiety represents. The compounds listed in the tables below are illustrative and not limiting.

TABLE I

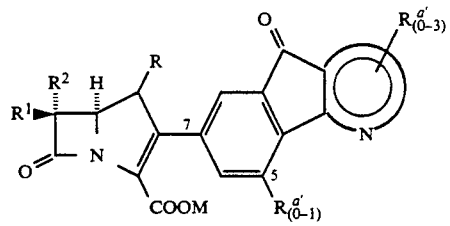

| N-pos. | R | $R^1$ | $R^2$ | M | $R^{a'}$ | $R^{a'}$ position |
|---|---|---|---|---|---|---|
| 1 | —H | —H | —CH(OH)CH₃ | Na⁺ | —CHO | 2 |
| 1 | —H | —H | —CH(OH)CH₃ | Na⁺ | —CHO | 3 |
| 2 | —H | —H | —CH(OH)CH₃ | Na⁺ | —CHO | 5 |
| 2 | —H | —H | —CH(OH)CH₃ | Na⁺ | —CHO | 3 |
| 2 | —H | —H | —CH(OH)CH₃ | Na⁺ | —CHO | 4 |
| 3 | —H | —H | —CH(OH)CH₃ | Na⁺ | —CHO | 1 |
| 3 | —H | —H | —CH(OH)CH₃ | Na⁺ | —CHO | 5 |
| 4 | —H | —H | —CH(OH)CH₃ | Na⁺ | —CHO | 3 |
| 4 | —H | —H | —CH(OH)CH₃ | Na⁺ | —CHO | 5 |
| 1 | —H | —H | —CH(OH)CH₃ | Na⁺ | —CN | 2 |
| 1 | —H | —H | —CH(OH)CH₃ | Na⁺ | —CN | 3 |
| 2 | —H | —H | —CH(OH)CH₃ | Na⁺ | —CN | 5 |
| 2 | —H | —H | —CH(OH)CH₃ | Na⁺ | —CN | 3 |
| 2 | —H | —H | —CH(OH)CH₃ | Na⁺ | —CN | 4 |
| 3 | —H | —H | —CH(OH)CH₃ | Na⁺ | —CN | 1 |
| 3 | —H | —H | —CH(OH)CH₃ | Na⁺ | —CN | 5 |
| 4 | —H | —H | —CH(OH)CH₃ | Na⁺ | —CN | 3 |
| 4 | —H | —H | —CH(OH)CH₃ | Na⁺ | —CN | 5 |
| 4 | —H | —H | —CH(OH)CH₃ | Na⁺ | —CN | 2 |
| 1 | —H | —H | —CH(OH)CH₃ | Na⁺ | —CH=NOH | 2 |
| 1 | —H | —H | —CH(OH)CH₃ | Na⁺ | —CH=NOH | 3 |
| 2 | —H | —H | —CH(OH)CH₃ | Na⁺ | —CH=NOH | 5 |
| 2 | —H | —H | —CH(OH)CH₃ | Na⁺ | —CH=NOH | 3 |
| 2 | —H | —H | —CH(OH)CH₃ | Na⁺ | —CH=NOH | 4 |
| 3 | —H | —H | —CH(OH)CH₃ | Na⁺ | —CH=NOH | 1 |
| 3 | —H | —H | —CH(OH)CH₃ | Na⁺ | —CH=NOH | 5 |

TABLE I-continued

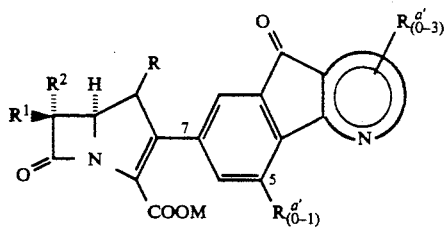

| N-pos. | R | $R^1$ | $R^2$ | M | $R^{a'}$ | $R^{a'}$ position |
|---|---|---|---|---|---|---|
| 4 | —H | —H | —CH(OH)CH$_3$ | Na$^+$ | —CH=NOH | 3 |
| 4 | —H | —H | —CH(OH)CH$_3$ | Na$^+$ | —CH=NOH | 5 |
| 4 | —H | —H | —CH(OH)CH$_3$ | Na$^+$ | —CH=NOH | 2 |
| 1 | —H | —H | —CH(OH)CH$_3$ | Na$^+$ | —CH$_2$OH | 2 |
| 1 | —H | —H | —CH(OH)CH$_3$ | Na$^+$ | —CH$_2$OH | 3 |
| 2 | —H | —H | —CH(OH)CH$_3$ | Na$^+$ | —CH$_2$OH | 5 |
| 2 | —H | —H | —CH(OH)CH$_3$ | Na$^+$ | —CH$_2$OH | 3 |
| 2 | —H | —H | —CH(OH)CH$_3$ | Na$^+$ | —CH$_2$OH | 4 |
| 3 | —H | —H | —CH(OH)CH$_3$ | Na$^+$ | —CH$_2$OH | 1 |
| 3 | —H | —H | —CH(OH)CH$_3$ | Na$^+$ | —CH$_2$OH | 5 |
| 4 | —H | —H | —CH(OH)CH$_3$ | Na$^+$ | —CH$_2$OH | 3 |
| 4 | —H | —H | —CH(OH)CH$_3$ | Na$^+$ | —CH$_2$OH | 5 |
| 4 | —H | —H | —CH(OH)CH$_3$ | Na$^+$ | —CH$_2$OH | 2 |
| 1 | —H | —H | —CH(OH)CH$_3$ | Na$^+$ | —CONH$_2$ | 2 |
| 1 | —H | —H | —CH(OH)CH$_3$ | Na$^+$ | —CONH$_2$ | 3 |
| 2 | —H | —H | —CH(OH)CH$_3$ | Na$^+$ | —CONH$_2$ | 5 |
| 2 | —H | —H | —CH(OH)CH$_3$ | Na$^+$ | —CONH$_2$ | 3 |
| 2 | —H | —H | —CH(OH)CH$_3$ | Na$^+$ | —CONH$_2$ | 4 |
| 3 | —H | —H | —CH(OH)CH$_3$ | Na$^+$ | —CONH$_2$ | 1 |
| 3 | —H | —H | —CH(OH)CH$_3$ | Na$^+$ | —CONH$_2$ | 5 |
| 4 | —H | —H | —CH(OH)CH$_3$ | Na$^+$ | —CONH$_2$ | 3 |
| 4 | —H | —H | —CH(OH)CH$_3$ | Na$^+$ | —CONH$_2$ | 5 |
| 4 | —H | —H | —CH(OH)CH$_3$ | Na$^+$ | —CONH$_2$ | 2 |
| 1 | —H | —H | —CH(OH)CH$_3$ | Na$^+$ | —CO$_2$CH$_3$ | 2 |
| 1 | —H | —H | —CH(OH)CH$_3$ | Na$^+$ | —CO$_2$CH$_3$ | 3 |
| 2 | —H | —H | —CH(OH)CH$_3$ | Na$^+$ | —CO$_2$CH$_3$ | 5 |
| 2 | —H | —H | —CH(OH)CH$_3$ | Na$^+$ | —CO$_2$CH$_3$ | 3 |
| 2 | —H | —H | —CH(OH)CH$_3$ | Na$^+$ | —CO$_2$CH$_3$ | 4 |
| 3 | —H | —H | —CH(OH)CH$_3$ | Na$^+$ | —CO$_2$CH$_3$ | 1 |
| 3 | —H | —H | —CH(OH)CH$_3$ | Na$^+$ | —CO$_2$CH$_3$ | 5 |
| 4 | —H | —H | —CH(OH)CH$_3$ | Na$^+$ | —CO$_2$CH$_3$ | 3 |
| 4 | —H | —H | —CH(OH)CH$_3$ | Na$^+$ | —CO$_2$CH$_3$ | 5 |
| 4 | —H | —H | —CH(OH)CH$_3$ | Na$^+$ | —CO$_2$CH$_3$ | 2 |
| 2 | —H | —H | —CH(OH)CH$_3$ | Na$^+$ | —OCH$_2$CO$_2$CH$_3$ | 3 |
| 1 | —H | —H | —CH(OH)CH$_3$ | K$^+$ | —OCH$_3$ | 2 |
| 3 | —H | —H | —CH(OH)CH$_3$ | K$^+$ | —OCH$_2$CH$_2$OH | 2 |
| 4 | —H | —H | —CH(OH)CH$_3$ | K$^+$ | —CF$_3$ | 3 |
| 3 | —H | —H | —CH(OH)CH$_3$ | Na$^+$ | —F | 1 |
| 2 | —H | —H | —CH(OH)CH$_3$ | Na$^+$ | —Cl | 5 |
| 4 | —H | —H | —CH(OH)CH$_3$ | K$^+$ | —Br | 3 |
| 1 | —H | —H | —CH$_2$OH | K$^+$ | —I | 2 |
| 3 | —H | —H | —CH(OH)CH$_3$ | K$^+$ | —OH | 5 |
| 2 | —H | —H | —CH(OH)CH$_3$ | Na$^+$ | —OCOCH$_3$ | 3 |
| 1 | —H | —H | —CH(OH)CH$_3$ | Na$^+$ | —OCONH$_2$ | 2 |
| 2 | —H | —H | —CH(OH)CH$_3$ | Na$^+$ | —SCH$_3$ | 5 |
| 3 | —H | —H | —CH(F)CH$_3$ | K$^+$ | —SOCH$_3$ | 3 |
| 4 | —CH$_3$ | —H | —CH(OH)CH$_3$ | Na$^+$ | —SO$_2$CH$_3$ | 5 |
| 3 | —H | —H | —CH(OH)CH$_3$ | Na$^+$ | —SCH$_2$CH$_2$OH | 2 |
| 4 | —H | —H | —CH(OH)CH$_3$ | Na$^+$ | —SOCH$_2$CH$_2$OH | 3 |
| 2 | —H | —H | —CH(OH)CH$_3$ | Na$^+$ | —SO$_2$CH$_2$CH$_2$OH | 3 |
| 2 | —H | —H | —CH(OH)CH$_3$ | K$^+$ | —SO$_2$NH$_2$ | 4 |
| 2 | —H | —H | —CH(OH)CH$_3$ | K$^+$ | —SO$_2$N(CH$_3$)$_2$ | 1 |
| 3 | —H | —H | —CF$_2$CH$_3$ | K$^+$ | —NHCHO | 3 |
| 1 | —CH$_3$ | —H | —CH(OH)CH$_3$ | K$^+$ | —NHCOCH$_3$ | 2 |
| 4 | —H | —H | —CH(OH)CH$_3$ | K$^+$ | —NHCO$_2$CH$_3$ | 3 |
| 3 | —H | —H | —CH(OH)CH$_3$ | Na$^+$ | —NHSO$_2$CH$_3$ | 2 |
| 3 | —H | —H | —CH(OH)CH$_3$ | K$^+$ | —COCH$_3$ | 4 |
| 1 | —H | —H | —CH(OH)CH$_3$ | K$^+$ | —COCH$_2$OH | 5 |
| 2 | —H | —H | —CH(OH)CH$_3$ | Na$^+$ | —CH=NOCH$_3$ | 3 |
| 3 | —H | —H | —CH(OH)CH$_3$ | K$^+$ | —CH=NOCH$_2$CO$_2$CH$_3$ | 1 |
| 4 | —CH$_3$ | —H | —CH(OH)CH$_3$ | Na$^+$ | —CH=NOCMe$_2$CO$_2$Me | 3 |
| 2 | —H | —H | —CH(OH)CH$_3$ | Na$^+$ | —CH=NOCMe$_2$CO$_2$Me | 1 |
| 3 | —H | —H | —CH(OH)CH$_3$ | K$^+$ | —CO$_2$CH$_2$CH$_2$OH | 5 |
| 2 | —H | —H | —CH(OH)CH$_3$ | K$^+$ | —CONHCH$_3$ | 3 |
| 4 | —H | —H | —CH(OH)CH$_3$ | K$^+$ | —CON(CH$_3$)$_2$ | 3 |
| 2 | —H | —H | —CH(OH)CH$_3$ | K$^+$ | —CONHCH$_2$CN | 5 |
| 2 | —CH$_3$ | —H | —CF$_2$CH$_3$ | Na$^+$ | —CONHCH$_2$CONH$_2$ | 1 |
| 3 | —H | —H | —CH(OH)CH$_3$ | K$^+$ | —CONHCH$_2$CO$_2$CH$_3$ | 4 |

TABLE I-continued

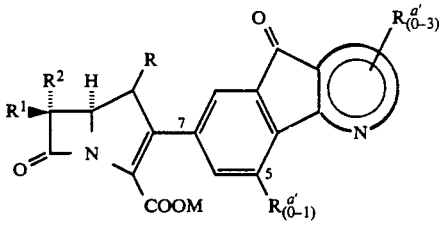

| N-pos. | R | $R^1$ | $R^2$ | M | $R^{a'}$ | $R^{a'}$ position |
|---|---|---|---|---|---|---|
| 1 | —H | —H | —CH(OH)CH$_3$ | Na$^+$ | —CONHOH | 2 |
| 1 | —H | —H | —CH(OH)CH$_3$ | Na$^+$ | —CONHOCH$_3$ | 5 |
| 3 | —H | —H | —CH(OH)CH$_3$ | Na$^+$ | -tetrazolyl | 2 |
| 4 | —H | —H | —CH(OH)CH$_3$ | Na$^+$ | —SCF$_3$ | 3 |
| 2 | —H | —H | —CH(OH)CH$_3$ | Na$^+$ | —PO$_3$CH$_3$H | 5 |
| 3 | —H | —H | —CH(OH)CH$_3$ | Na$^+$ | —CONHSO$_2$Ph | 2 |
| 3 | —CH$_3$ | —H | —CH(OH)CH$_3$ | Na$^+$ | —CONHSO$_2$NH$_2$ | 5 |
| 2 | —H | —H | —CH(OH)CH$_3$ | Na$^+$ | —SO$_3$CH$_3$ | 3 |
| 4 | —H | —H | —CH(OH)CH$_3$ | Na$^+$ | —SO$_2$NHCN | 3 |
| 2 | —CH$_3$ | —H | —CH(F)CH$_3$ | Na$^+$ | —SO$_2$NHCONH$_2$ | 5 |
| 1 | —H | —H | —CH(OH)CH$_3$ | K$^+$ | —CH=CHCN | 5 |
| 2 | —H | —H | —CH(OH)CH$_3$ | K$^+$ | —CH=CHCONH$_2$ | 1 |
| 2 | —H | —H | —CH(OH)CH$_3$ | Na$^+$ | —CH=CHCO$_2$CH$_3$ | 3 |
| 4 | —H | —H | —CH(OH)CH$_3$ | Na$^+$ | —C≡C—CONH$_2$ | 3 |
| 3 | —CH$_3$ | —H | —CH(OH)CH$_3$ | Na$^+$ | —C≡C—CN | 2 |
| 4 | —H | —H | —CH$_2$CH$_3$ | K$^+$ | —CH$_2$N$_3$ | 5 |
| 2 | —H | —H | —CH(OH)CH$_3$ | Na$^+$ | —CH$_2$CO$_2$CH$_3$ | 3 |
| 1 | —H | —H | —CH(OH)CH$_3$ | Na$^+$ | —CH$_2$CO$_2$CH$_3$ | 2 |
| 3 | —CH$_3$ | —H | —CH(OH)CH$_3$ | Na$^+$ | —CN | 5 |
| 3 | —H | —H | —CH(OH)CH$_3$ | Na$^+$ | —CO$_2$CH$_3$ | 1 |
| 3 | —H | —H | —CH(F)CH$_3$ | Na$^+$ | —CO$_2$CH$_3$ | 2 |
| 2 | —CH$_3$ | —H | —CH(OH)CH$_3$ | Na$^+$ | —CH$_2$CO$_2$CH$_3$ | 5 |
| 3 | —H | —H | —CH(OH)CH$_3$ | Na$^+$ | —SCH$_3$ | 5 |
| 2 | —H | —H | —CH(F)CH$_3$ | Na$^+$ | —SOCH$_3$ | 4 |
| 4 | —CH$_3$ | —H | —CH(OH)CH$_3$ | Na$^+$ | —SO$_2$CH$_3$ | 5 |
| 3 | —H | —H | —CH(OH)CH$_3$ | Na$^+$ | —CH=CHCN | 2 |
| 1 | —H | —H | —CH(OH)CH$_3$ | Na$^+$ | —CH=CHCN | 2 |
| 3 | —H | —H | —CH(OH)CH$_3$ | Na$^+$ | —SOCH$_3$ | 1 |
| 3 | —H | —H | —CH(OH)CH$_3$ | Na$^+$ | —SOCH$_3$ | 5 |

TABLE II

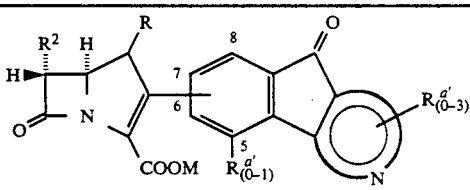

| N-pos. | Att pt | R | $R^2$ | M | $R^{a'}$ | $R^{a'}$ position |
|---|---|---|---|---|---|---|
| 1 | 5 | —H | —CH(OH)CH$_3$ | Na$^+$ | —CHO | 2 |
| 1 | 6 | —H | —CH(OH)CH$_3$ | Na$^+$ | —CHO | 3 |
| 2 | 8 | —H | —CH(OH)CH$_3$ | Na$^+$ | —CHO | 5 |
| 2 | 5 | —H | —CH(OH)CH$_3$ | Na$^+$ | —CHO | 3 |
| 2 | 6 | —H | —CH(OH)CH$_3$ | Na$^+$ | —CHO | 4 |
| 3 | 5 | —H | —CH(OH)CH$_3$ | Na$^+$ | —CHO | 1 |
| 3 | 8 | —H | —CH(OH)CH$_3$ | Na$^+$ | —CHO | 5 |
| 4 | 6 | —H | —CH(OH)CH$_3$ | Na$^+$ | —CHO | 3 |
| 4 | 5 | —H | —CH(OH)CH$_3$ | Na$^+$ | —CHO | 5 |
| 1 | 6 | —H | —CH(OH)CH$_3$ | Na$^+$ | —CN | 2 |
| 1 | 6 | —H | —CH(OH)CH$_3$ | Na$^+$ | —CN | 3 |
| 2 | 8 | —H | —CH(OH)CH$_3$ | Na$^+$ | —CN | 5 |
| 2 | 8 | —H | —CH(OH)CH$_3$ | Na$^+$ | —CN | 3 |
| 2 | 5 | —H | —CH(OH)CH$_3$ | Na$^+$ | —CN | 4 |
| 3 | 8 | —H | —CH(OH)CH$_3$ | Na$^+$ | —CN | 1 |
| 3 | 5 | —H | —CH(OH)CH$_3$ | Na$^+$ | —CN | 2 |
| 4 | 6 | —H | —CH(OH)CH$_3$ | Na$^+$ | —CN | 3 |
| 4 | 6 | —H | —CH(OH)CH$_3$ | Na$^+$ | —CN | 1 |
| 4 | 5 | —H | —CH(OH)CH$_3$ | Na$^+$ | —CN | 2 |
| 1 | 6 | —H | —CH(OH)CH$_3$ | Na$^+$ | —CH=NOH | 2 |
| 1 | 8 | —H | —CH(OH)CH$_3$ | Na$^+$ | —CH=NOH | 3 |
| 2 | 8 | —H | —CH(OH)CH$_3$ | Na$^+$ | —CH=NOH | 5 |
| 2 | 5 | —H | —CH(OH)CH$_3$ | Na$^+$ | —CH=NOH | 3 |

TABLE II-continued

| N-pos. | Att pt | R | $R^2$ | M | $R^{a'}$ | $R^{a'}$ position |
|---|---|---|---|---|---|---|
| 2 | 6 | —H | —CH(OH)CH$_3$ | Na$^+$ | —CH=NOH | 4 |
| 3 | 5 | —H | —CH(OH)CH$_3$ | Na$^+$ | —CH=NOH | 1 |
| 3 | 6 | —H | —CH(OH)CH$_3$ | Na$^+$ | —CH=NOH | 2 |
| 4 | 6 | —H | —CH(OH)CH$_3$ | Na$^+$ | —CH=NOH | 3 |
| 4 | 6 | —H | —CH(OH)CH$_3$ | Na$^+$ | —CH=NOH | 1 |
| 4 | 8 | —H | —CH(OH)CH$_3$ | Na$^+$ | —CH=NOH | 2 |
| 1 | 6 | —H | —CH(OH)CH$_3$ | Na$^+$ | —CH$_2$OH | 2 |
| 1 | 6 | —H | —CH(OH)CH$_3$ | Na$^+$ | —CH$_2$OH | 3 |
| 2 | 8 | —H | —CH(OH)CH$_3$ | Na$^+$ | —CH$_2$OH | 5 |
| 2 | 6 | —H | —CH(OH)CH$_3$ | Na$^+$ | —CH$_2$OH | 3 |
| 2 | 6 | —H | —CH(OH)CH$_3$ | Na$^+$ | —CH$_2$OH | 4 |
| 3 | 5 | —H | —CH(OH)CH$_3$ | Na$^+$ | —CH$_2$OH | 1 |
| 3 | 6 | —H | —CH(OH)CH$_3$ | Na$^+$ | —CH$_2$OH | 2 |
| 4 | 8 | —H | —CH(OH)CH$_3$ | Na$^+$ | —CH$_2$OH | 3 |
| 4 | 6 | —H | —CH(OH)CH$_3$ | Na$^+$ | —CH$_2$OH | 3 |
| 4 | 5 | —H | —CH(OH)CH$_3$ | Na$^+$ | —CH$_2$OH | 2 |
| 1 | 6 | —H | —CH(OH)CH$_3$ | Na$^+$ | —CONH$_2$ | 2 |
| 1 | 6 | —H | —CH(OH)CH$_3$ | Na$^+$ | —CONH$_2$ | 3 |
| 2 | 8 | —H | —CH(OH)CH$_3$ | Na$^+$ | —CONH$_2$ | 5 |
| 2 | 6 | —H | —CH(OH)CH$_3$ | Na$^+$ | —CONH$_2$ | 3 |
| 2 | 6 | —H | —CH(OH)CH$_3$ | Na$^+$ | —CONH$_2$ | 4 |
| 3 | 8 | —H | —CH(OH)CH$_3$ | Na$^+$ | —CONH$_2$ | 1 |
| 3 | 6 | —H | —CH(OH)CH$_3$ | Na$^+$ | —CONH$_2$ | 2 |
| 4 | 6 | —H | —CH(OH)CH$_3$ | Na$^+$ | —CONH$_2$ | 3 |
| 4 | 5 | —H | —CH(OH)CH$_3$ | Na$^+$ | —CONH$_2$ | 2 |
| 4 | 8 | —H | —CH(OH)CH$_3$ | Na$^+$ | —CONH$_2$ | 2 |
| 1 | 6 | —H | —CH(OH)CH$_3$ | Na$^+$ | —CO$_2$CH$_3$ | 2 |
| 1 | 5 | —H | —CH(OH)CH$_3$ | Na$^+$ | —CO$_2$CH$_3$ | 3 |
| 2 | 6 | —H | —CH(OH)CH$_3$ | Na$^+$ | —CO$_2$CH$_3$ | 1 |
| 2 | 6 | —H | —CH(OH)CH$_3$ | Na$^+$ | —CO$_2$CH$_3$ | 3 |
| 2 | 5 | —H | —CH(OH)CH$_3$ | Na$^+$ | —CO$_2$CH$_3$ | 4 |
| 3 | 6 | —H | —CH(OH)CH$_3$ | Na$^+$ | —CO$_2$CH$_3$ | 1 |
| 3 | 6 | —H | —CH(OH)CH$_3$ | Na$^+$ | —CO$_2$CH$_3$ | 2 |
| 4 | 8 | —H | —CH(OH)CH$_3$ | Na$^+$ | —CO$_2$CH$_3$ | 3 |
| 4 | 8 | —H | —CH(OH)CH$_3$ | Na$^+$ | —CO$_2$CH$_3$ | 5 |
| 4 | 6 | —H | —CH(OH)CH$_3$ | Na$^+$ | —CO$_2$CH$_3$ | 2 |
| 2 | 6 | —H | —CH(OH)CH$_3$ | Na$^+$ | —OCH$_2$CO$_2$CH$_3$ | 3 |
| 1 | 6 | —H | —CH(OH)CH$_3$ | K$^+$ | —OCH$_3$ | 2 |
| 3 | 5 | —H | —CH(OH)CH$_3$ | K$^+$ | —OCH$_2$CH$_2$OH | 2 |
| 4 | 6 | —H | —CH(OH)CH$_3$ | K$^+$ | —CF$_3$ | 3 |
| 3 | 6 | —H | —CH(OH)CH$_3$ | Na$^+$ | —F | 1 |
| 2 | 8 | —H | —CH(OH)CH$_3$ | Na$^+$ | —Cl | 5 |
| 4 | 6 | —H | —CH(OH)CH$_3$ | K$^+$ | —Br | 3 |
| 1 | 6 | —H | —CH$_2$OH | K$^+$ | —I | 2 |
| 3 | 8 | —H | —CH(OH)CH$_3$ | K$^+$ | —OH | 5 |
| 2 | 5 | —H | —CH(OH)CH$_3$ | Na$^+$ | —OCOCH$_3$ | 3 |
| 1 | 5 | —H | —CH(OH)CH$_3$ | Na$^+$ | —OCONH$_2$ | 2 |
| 2 | 6 | —H | —CH(OH)CH$_3$ | Na$^+$ | —SCH$_3$ | 1 |
| 3 | 6 | —H | —CH(F)CH$_3$ | K$^+$ | —SOCH$_2$CH$_2$OH | 3 |
| 4 | 5 | —CH$_3$ | —CH(OH)CH$_3$ | Na$^+$ | —SO$_2$CH$_3$ | 2 |
| 3 | 6 | —H | —CH(OH)CH$_3$ | Na$^+$ | —SCH$_2$CH$_2$OH | 2 |
| 4 | 8 | —H | —CH(OH)CH$_3$ | Na$^+$ | —SOCH$_2$CH$_2$OH | 3 |
| 2 | 6 | —H | —CH(OH)CH$_3$ | K$^+$ | —SO$_2$CH$_2$CH$_2$OH | 3 |
| 2 | 6 | —H | —CH(OH)CH$_3$ | Na$^+$ | —SO$_2$NH$_2$ | 4 |
| 2 | 6 | —H | —CH(OH)CH$_3$ | K$^+$ | —SO$_2$N(CH$_3$)$_2$ | 1 |
| 3 | 6 | —H | —CF$_2$CH$_3$ | K$^+$ | —NHCHO | 2 |
| 1 | 5 | —CH$_3$ | —CH(OH)CH$_3$ | K$^+$ | —NHCOCH$_3$ | 2 |
| 4 | 6 | —H | —CH(OH)CH$_3$ | K$^+$ | —NHCO$_2$CH$_3$ | 3 |
| 3 | 8 | —H | —CH(OH)CH$_3$ | Na$^+$ | —NHSO$_2$CH$_3$ | 2 |
| 3 | 6 | —H | —CH(OH)CH$_3$ | K$^+$ | —COCH$_3$ | 4 |
| 1 | 8 | —H | —CH(OH)CH$_3$ | K$^+$ | —COCH$_2$OH | 5 |
| 2 | 6 | —H | —CH(OH)CH$_3$ | Na$^+$ | —CH=NOCH$_3$ | 3 |
| 3 | 6 | —H | —CH(OH)CH$_3$ | K$^+$ | —CH=NOCH$_2$CO$_2$CH$_3$ | 1 |
| 4 | 6 | —CH$_3$ | —CH(OH)CH$_3$ | Na$^+$ | —CH=NOCMe$_2$CO$_2$Me | 3 |
| 2 | 6 | —H | —CH(OH)CH$_3$ | Na$^+$ | —CH=NOCMe$_2$CO$_2$Me | 1 |
| 3 | 8 | —H | —CH(OH)CH$_3$ | K$^+$ | —CO$_2$CH$_2$CH$_2$OH | 5 |
| 2 | 5 | —H | —CH(OH)CH$_3$ | K$^+$ | —CONHCH$_3$ | 3 |
| 4 | 6 | —H | —CH(OH)CH$_3$ | K$^+$ | —CON(CH$_3$)$_2$ | 3 |
| 2 | 8 | —H | —CH(OH)CH$_3$ | K$^+$ | —CONHCH$_2$CN | 5 |
| 2 | 6 | —CH$_3$ | —CF$_2$CH$_3$ | Na$^+$ | —CONHCH$_2$CONH$_2$ | 1 |

TABLE II-continued

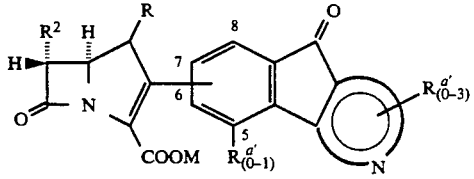

| N— pos. | Att pt | R | R² | M | Rᵃ' | Rᵃ' position |
|---|---|---|---|---|---|---|
| 3 | 6 | —H | —CH(OH)CH₃ | K⁺ | —CONHCH₂CO₂CH₃ | 4 |
| 1 | 6 | —H | —CH(OH)CH₃ | Na⁺ | —CONHOH | 2 |
| 1 | 8 | —H | —CH(OH)CH₃ | Na⁺ | —CONHOCH₃ | 5 |
| 3 | 5 | —H | —CH(OH)CH₃ | Na⁺ | -tetrazolyl | 2 |
| 4 | 6 | —H | —CH(OH)CH₃ | Na⁺ | —SCF₃ | 3 |
| 2 | 6 | —H | —CH(OH)CH₃ | Na⁺ | —PO₃CH₃H | 4 |
| 3 | 6 | —H | —CH(OH)CH₃ | Na⁺ | —CONHSO₂Ph | 2 |
| 3 | 8 | —CH₃ | —CH(OH)CH₃ | Na⁺ | —CONHSO₂NH₂ | 5 |
| 2 | 6 | —H | —CH(OH)CH₃ | Na⁺ | —SO₃CH₃ | 3 |
| 4 | 6 | —H | —CH(OH)CH₃ | Na⁺ | —SO₂NHCN | 3 |
| 2 | 8 | —CH₃ | —CH(F)CH₃ | Na⁺ | —SO₂NHCONH₂ | 5 |
| 1 | 8 | —H | —CH(OH)CH₃ | K⁺ | —CH=CHCN | 5 |
| 2 | 6 | —H | —CH(OH)CH₃ | K⁺ | —CH=CHCONH₂ | 1 |
| 2 | 6 | —H | —CH(OH)CH₃ | Na⁺ | —CH=CHCO₂CH₃ | 3 |
| 4 | 6 | —H | —CH(OH)CH₃ | Na⁺ | —C≡C—CONH₂ | 3 |
| 3 | 6 | —CH₃ | —CH(OH)CH₃ | Na⁺ | —C≡C—CN | 2 |
| 4 | 8 | —H | —CH₂CH₃ | K⁺ | —CH₂N₃ | 5 |
| 2 | 6 | —H | —CH(OH)CH₃ | Na⁺ | —CH₂CO₂CH₃ | 3 |
| 1 | 6 | —H | —CH(OH)CH₃ | Na⁺ | —CH₂CO₂CH₃ | 2 |
| 3 | 8 | —CH₃ | —CH(OH)CH₃ | Na⁺ | —CN | 3 |
| 3 | 6 | —H | —CH(OH)CH₃ | Na⁺ | —CO₂CH₃ | 1 |
| 3 | 6 | —H | —CH(F)CH₃ | Na⁺ | —CO₂CH₃ | 2 |
| 2 | 6 | —CH₃ | —CH(OH)CH₃ | Na⁺ | —CH₂CO₂CH₃ | 2 |
| 3 | 8 | —H | —CH(OH)CH₃ | Na⁺ | —SCH₃ | 5 |
| 2 | 6 | —H | —CH(F)CH₃ | Na⁺ | —SOCH₃ | 4 |
| 4 | 6 | —CH₃ | —CH(OH)CH₃ | Na⁺ | —SO₂CH₃ | 2 |
| 3 | 6 | —H | —CH(OH)CH₃ | Na⁺ | —CH=CHCN | 2 |
| 1 | 5 | —H | —CH(OH)CH₃ | Na⁺ | —CH=CHCN | 2 |
| 3 | 6 | —H | —CH(OH)CH₃ | Na⁺ | —SOCH₃ | 1 |
| 3 | 8 | —H | —CH(OH)CH₃ | Na⁺ | —SOCH₃ | 5 |

The carbapenem compounds of the present invention are useful per se and in their pharmaceutically acceptable salt and ester forms in the treatment of bacterial infections in animal and human subjects. The term "pharmaceutically acceptable ester or salt" refers to those salt and ester forms of the compounds of the present invention which would be apparent to the pharmaceutical chemist, i.e., those which are non-toxic and which would favorably affect the pharmacokinetic properties of said compounds, their palatability, absorption, distribution, metabolism and excretion. Other factors, more practical in nature, which are also important in the selection, are cost of the raw materials, ease of crystallization, yield, stability, hygroscopicity, and flowability of the resulting bulk drug. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel carbapenem compounds of the present invention.

The pharmaceutically acceptable salts referred to above may take the form —COOM. The M may be an alkali metal cation such as sodium or potassium. Other pharmaceutically acceptable cations for M may be calcium, magnesium, zinc, ammonium, or alkylammonium cations such as tetramethylammonium, tetrabutylammonium, choline, triethylhydroammonium, meglumine, triethanolhydroammonium, etc.

The pharmaceutically acceptable esters of the novel carbapenem compounds of the present invention are such as would be readily apparent to a medicinal chemist, and include, for example, those described in detail in U.S. Pat. No. 4,309,438, Column 9, line 61 to Column 12, line 51. Included within such pharmaceutically acceptable esters are those which are hydrolyzed under physiological conditions, such as pivaloyloxymethyl, acetoxymethyl, phthalidyl, indanyl and methoxymethyl, and those described in detail in U.S. Pat. No. 4,479,947.

The novel carbapenem compounds of the present invention may take the form COOM, where M is a readily removable carboxyl protecting group. Such conventional blocking groups consist of known ester groups which are used to protectively block the carboxyl group during the synthesis procedures described above. These conventional blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile, and catalytic hydrogenation. Examples of such ester protecting groups include benzhydryl, p-nitrobenzyl, 2-naphthylmethyl, allyl, benzyl, trichloroethyl, silyl such as trimethylsilyl, trimethylsilylethyl, phenacyl, p-methoxybenzyl, acetonyl, o-nitrobenzyl, p-methoxyphenyl, 4-pyridylmethyl, and t-butyl.

The compounds of the present invention are valuable antibacterial agents active against various Gram-positive and to a lesser extent Gram-negative bacteria and accordingly find utility in human and veterinary medicine. The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy or inhibit the growth of harmful bacteria or medical and dental equipment and as bactericides in industrial applications, for example in waterbased paints and in the white water of paper mills to inhibit the growth of harmful bacteria.

The compounds of this invention may be used in any of a variety of pharmaceutical preparations. They may be employed in capsule, powder form, in liquid solution, or in suspension. They may be administered by a variety of means; those of principal interest include: topically or parenterally by injection (intravenously or intramuscularly).

Compositions for injection, a preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water. Topical applications may be formulated in hydrophobic or hydrophilic bases as ointments, creams, lotions, paints, or powders.

The dosage to be administered depends to a large extent upon the condition and size of the subject being treated as well as the route and frequency of administration, the parenteral route by injection being preferred for generalized infections. Such matters, however, are left to the routine discretion of the therapist according to principles of treatment well known in the anti-bacterial art. Another factor influencing the precise dosage regimen, apart from the nature of the infection and peculiar identity of the individual being treated, is the molecular weight of the chosen species of this invention.

The compositions for human delivery per unit dosage, whether liquid or solid, may contain from 0.1% to 99% of active material, the preferred range being from about 10-60%. The composition will generally contain from about 15 mg to about 1500 mg of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution.

The preferred method of administration of the Formula I antibacterial compounds is parenteral by i.v. infusion, i.v. bolus, or i.m. injection.

For adults, 5–50 mg of Formula I antibacterial compounds per kg of body weight given 2, 3, or 4 times per day is preferred. Preferred dosage is 250 mg to 1000 mg of the Formula I antibacterial given two (b.i.d.) three (t.i.d.) or four (q.i.d.) times per day. More specifically, for mild infections a dose of 250 mg t.i.d. or q.i.d. is recommended. For moderate infections against highly susceptible gram positive organisms a dose of 500 mg t.i.d. or q.i.d. is recommended. For severe, life-threatening infections against organisms at the upper limits of sensitivity to the antibiotic, a dose of 1000 mg t.i.d. or q.i.d. is recommended.

For children, a dose of 5–25 mg/kg of body weight given 2, 3, or 4 times per day is preferred; a dose of 10 mg/kg t.i.d. or q.i.d. is usually recommended.

Antibacterial compounds of Formula I are of the broad class known as carbapenems or 1-carbadethiapenems. Naturally occuring carbapenems are susceptible to attack by a renal enzyme known as dehydropeptidase (DHP). This attack or degradation may reduce the efficacy of the carbapenem antibacterial agent. The compounds of the present invention, on the other hand, are significantly less subject to such attack, and therefore may not require the use of a DHP inhibitor. However, such use is optional and contemplated to be part of the present invention. Inhibitors of DHP and their use with carbapenem antibacterial agents are disclosed in the prior art [see European Patent Applications No. 79102616.4 filed Jul. 24, 1979 (Patent No. 0 007 614); and No. 82107174.3, filed Aug. 9, 1982 (Publication No. 0 072 014)].

The compounds of the present invention may, where DHP inhibition is desired or necessary, be combined or used with the appropriate DHP inhibitor as described in the aforesaid patents and published application. Thus, to the extent that the cited European patent applications 1.) define the procedure for determining DHP susceptibility of the present carbapenems and 2.) disclose suitable inhibitors, combination compositions and methods of treatment, they are incorporated herein by reference. A preferred weight ratio of Formula I compound: DHP inhibitor in the combination compositions is about 1:1. A preferred DHP inhibitor is 7-(L-2-amino-2-carboxyethylthio)-2-(2,2-dimethylcyclopropanecarboxamide)-2-heptenoic acid or a useful salt thereof.

The invention is further defined by reference to the following examples, which are illustrative and not limiting. All temperatures are in degrees Celsius.

EXAMPLE 1

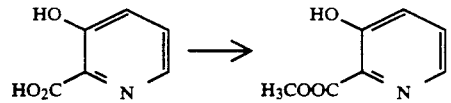

Methyl 3-hydroxypicolinate:

15 g (0.15 mole) of N-nitrosomethylurea was added portionwise over 15 mins. to a stirring mixture of 50 mL of 40% potassium hydroxide and 125 mL of ether. The resulting yellow ether layer was decanted and dried over potassium hydroxide pellets. The decanted dried ether layer was slowly added to a solution/suspension of 13.9 g (0.1 mole) of commercially available 3-hydroxy picolinic acid in 400 mL of tetrahydrofuran at 0°. After stirring 1 hr., part of the ether was removed in vacuo at <r.t.; this procedure also removed excess diazomethane. Solid was then filtered. The filtrate was concentrated to give methyl 3-hydroxy picolinate as oil.

$^1$H NMR (CDCl$_3$, 400 MHz): δ3.98 (s; CH$_3$); 7.36 (dd; J=1.5 & 8 Hz; γ-H of pyridine); 7.41 (dd; J=4 & 8 Hz; β-H of pyridine); 8.26 (dd; J=1.5 & 4 Hz; α-H of pyridine)

EXAMPLE 2

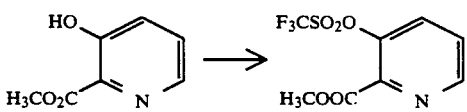

Methyl 3-trifluoromethanesulfonyl picolinate:

1.85 mL (11 mmole) of trifluoromethane sulfonic anhydride was added slowly to a stirred mixture of 1.53 g (10 mmole) of methyl 3-hydroxy picolinate in 20 mL of acetonitrile at 0° under nitrogen. The resulting burgundy colored reaction mixture was stirred 30 mins. at 0°. The solvent was evaporated in vacuo at <r.t. The residue was taken up in 50 mL of ethyl acetate and washed with 2×20 mL of ice water and then with sat'd sodium chloride solution. The organic phase was dried over anhyd. magnesium sulfate. Solvent removal gave the crude product, which was purified on silica gel using 1:3 mixture of ethyl acetate:hexane as eluant to give the desired methyl 3-trifluoromethanesulfonyl picolinate as light yellow oil.

$^1$H NMR (CDCl$_3$, 400 MHz): δ3.98 (s, CH$_3$); 8.75 (dd; J=1.5 & 5 Hz; α-H of pyridine); 7.71 (dd; J=1.5 & 8 Hz; γ-H of pyridine); 7.61 (dd; J=5 & 8 Hz; β-H of pyridine)

EXAMPLE 3

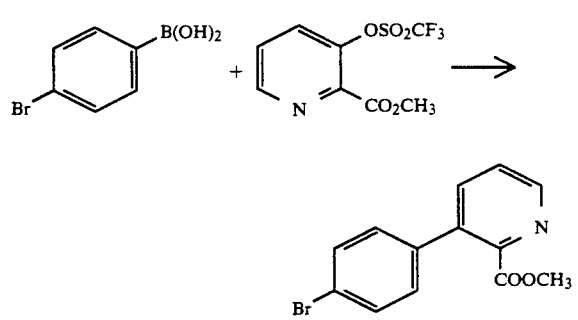

Methyl 3-(4'-bromophenyl)picolinate:

A mixture of 2.89 g (10 mmole) of methyl 3-trifluoromethanesulfonyloxy picolinate, 2 g (10 mmole) of 4-bromophenyl boronic acid, 300 mg of tetrakis-triphenylphospine palladium, and 10 mL of 2M sodium carbonate solution in 30 mL of 1,2-dimethoxyethane was heated to reflux overnight. The reaction mixture was cooled, diluted with 100 mL of ether and washed with 2×50 mL of sat'd. sodium chloride solution. The organic phase was dried over anhyd. magnesium sulfate. Solvent removal gave the crude product, which was purified on silica gel using 2:3 ethyl acetate:hexane as eluant to give methyl 3-(4'-bromophenyl)picolinate as thick oil.

$^1$H NMR (CDCl$_3$, 400 MHz): δ3.77 (s, CH$_3$); 8.67 (dd; J=1.5 & 5 Hz; α-H of pyridine); 7.7 (dd; J=1.5 & 8 Hz; γ-H of pyridine); 7.48 (dd; J=5 & 8 Hz; β-H of pyridine); 7.18 & 7.54 (phenyl protons)

EXAMPLE 4

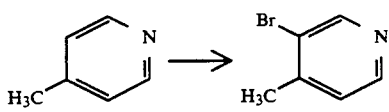

3-Bromo-4-picoline:

4-picoline (23 g, 0.25 mole) was added under nitrogen to mechanically stirred solid aluminum chloride (100 g, 0.75 mole). This slurry was heated with stirring to 100° C., and 20 g (0.125 mole) of bromine was added over a period of 1 hr. The heating was continued at 100° C. for 0.5 hr. The reaction mixture was poured into 1 L of ice water containing 38 mL of conc. hydrochloric acid. Additional conc. hydrochloric acid was added until the mixture became acidic. Excess sodium bisulfite solid was added, and the mixture was left overnight at r.t., decanted, and washed with 3×75 mL of methylene chloride. The aqueous phase was made alkaline with 50% sodium hydroxide solution and extracted with ether (4×75 mL). The organic phase was washed with brine (50 mL) and dried. Solvent removal gave 28 g of residue, which was chromatographed on silica gel using 1:9 mixture of ether:petroleum ether as solvent to provide 3-bromo-4-picoline as oil.

$^1$H NMR (CDCl$_3$, 400 MHz): δ2.4 (s; CH$_3$); 8.65 (s; α-H of pyridine); 8.38 (d, J=5 Hz; γ-H of pyridine); 7.18 (d, J=5 Hz; β-H of pyridine)

EXAMPLE 5

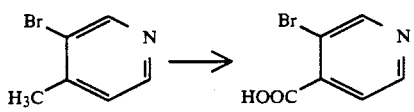

3-Bromoisonicotinic acid:

12.9 g (75 mmole) of 3-bromo-4-picoline was added to a purple solution of 23.7 g (0.15 mole) of potassium permanganate in 600 mL of water. This mixture was vigorously stirred 36 hrs. at 45° C. The resulting black solid was filtered and washed with 4×50 mL of hot water. The filtrate was concentrated to ~50 mL. A viscous liquid with black solid resulted. This was filtered through celite, which was washed with 3×20 mL of water. 150 mL of ice cold 2N hydrochloric acid was added. The resulting voluminous white precipitate was filtered and the solid was dried in vacuo to give 3-bromoisonicotinic acid as white powder.

$^1$H NMR (D$_6$-DMSO, 400 MHz): δ8.84 (s; H2); 8.63 (d; J=5 Hz; H6); 7.66 (d; J=5 Hz; H5)

EXAMPLE 6

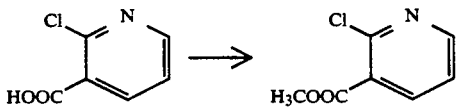

Methyl 2-chloronicotinate:

15.75 g (0.1 mole) of commercially available 2-chloronicotinic acid was dissolved in 100 mL of N,N-dimethylformamide. After cooling this solution to 0° under nitrogen, 4.4 g (0.11 mole) of 60% sodium hydride was added portionwise while evolved hydrogen gas was vented. The reaction mixture was stirred until the effervescence stopped (~2 hrs.). 7.5 mL (0.112 mole) of methyl iodide was then added dropwise. Stirring of the reaction mixture was continued overnight. Solvent was removed in vacuo at r.t. The resulting brown residue was partitioned between ethyl acetate and water. The organic phase was then washed with brine and dried over anhydrous magnesium sulfate. Solvent removal gave a residue which was purified on silica gel using 1:1 ethyl acetate:hexane mixture to give the desired methyl 2-chloronicotinate as oil.

EXAMPLE 7

Methyl 3-bromoisonicotinate

Using the procedure described in Example 6 but employing 3-bromoisonicotinic acid (prepared as desribed in Example 5) in place of 2-chloronicotinic acid provided the title compound.

$^1$H NMR (CDCl$_3$, 400 MHz): δ3.95 (s; CH$_3$); 8.85 (s; H2); 8.61 (d; J=5H; H6); 7.61 (d; J=5 Hz; H5).

EXAMPLE 8

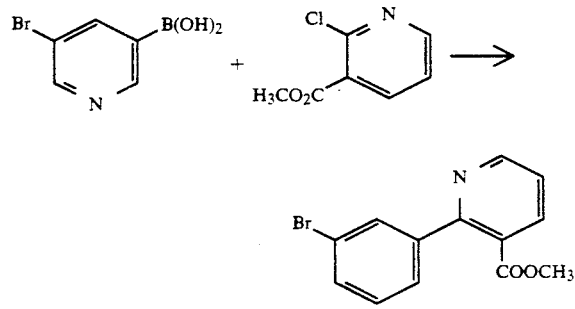

Methyl 2-[3-bromophenyl]nicotinate:

A mixture of 4.02 g (20 mmole) of 3-bromophenyl boronic acid, 6.86 g (40 mmole) of methyl 2-chloronicotinate, 600 mg of tetrakis-(triphenylphosphine) palladium, 25 mL of 2M solution of sodium carbonate, 50 mL of toluene, and 13 mL of ethanol was heated 20 hours at 80°. The reaction mixture was cooled to r.t. and partitioned between ethyl acetate and saturated sodium chloride solution. The organic phase was washed with sodium chloride solution several times, and dried over anhydrous magnesium sulfate. Solvent removal gave a crude product, which was chromatographed on silica gel using 1:4 ethyl acetate:hexane mixture as eluant to give methyl 2-[3-bromophenyl]-nicotinate as white amorphous powder.

$^1$H NMR (CDCl$_3$, 400 MHz): δ3.70 (s; 3H; CH$_3$); 8.72–8.76 (dd; J=2 & 5 Hz; α-H of pyridine)

EXAMPLE 9

Methyl 3-(4-bromophenyl)isonicotinate:

Employing the procedure described in Example 8, but reacting methyl 3-bromoisonicotinate in the place of methyl 2-chloronicotinate, provided the title compound.

$^1$H NMR (CDCl$_3$, 400 MHz): δ3.7 (s; CH$_3$); 8.71 (d; J=5 Hz; H6 of pyridine); 8.62 (s; H2 of pyridine); 7.66 (d; J=5 Hz; H5 of pyridine); 7.18 & 7.56 (phenyl protons)

EXAMPLE 10

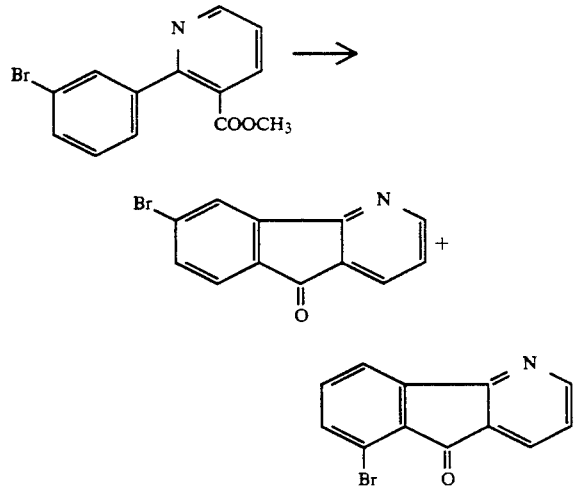

6-Bromo-4-aza-9-fluorenone and 8-bromo-4-aza-9-fluorenone

A 500 mL r.b. flask containing 1 g of methyl 2-[3-bromophenyl]nicotinate and 30 g of polyphosphoric acid with a stirring bar was dipped in an oil bath at 210° C. While the contents were being warmed, house vacuum (~30 mmole) was slowly applied. After 15 mins., the reaction mixture started to stir easily and slowly started turning orange. This reaction mixture was stirred at 210° and 30 mm pressure for 4 hrs. The flask was taken out and while it was still warm, ~50 g of ice was cautiously added to the reaction mixture. After cooling the stirring reaction mixture to 0°, 60 mL of 5N sodium hydroxide was added slowly over 3 mins. The resulting green solid was filtered and washed thoroughly with 5×25 mL of water. This crude solid was taken up in methylene chloride and applied on silica gel and eluted with 1:20 ethyl acetate:hexane mixture to give a 1:2 ratio of 6-bromo-4-aza-9-fluorenone and 8-bromo-4-aza-9-fluorenone as yellow solids.

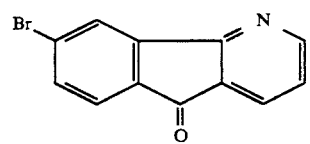

$^1$H NMR (CDCl$_3$, 400 MHz): δ8.0 (t, 1H); 7.56 (d, 2H; phenyl); 8.6 (dd; J=1.5 & 6 Hz; α-H of pyridine); 7.68 & 7.22 (pyridine H's)

IR (CH$_2$Cl$_2$): 1728 (C=O)

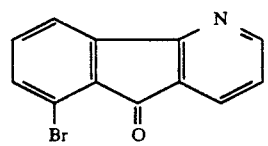

$^1$H NMR: δ8.6 (dd; J=1.5 & 6 Hz; α-H of pyridine); 7.16–7.92 (5 sets of other aromatic protons)

Using the procedure described in Example 10, the following compounds were prepared from the appropriate starting materials.

EXAMPLE 11

7-Bromo-4-azafluoren-9-one:
$^1$H NMR (CDCl$_3$, 400 MHz): δ8.62 (dd; J=1.5 & 5 Hz; α-H of pyridine); 7.91 (dd; J=1.5 & 7 Hz; γ-H of pyridine); 7.26 (dd; J=5 & 7 Hz; β-H of pyridine); 7.75(d) & 7.89(t) (phenyl ring protons);
IR: 1730 cm$^{-1}$ (C=O)

EXAMPLE 12

7-Bromo-1-azafluoren-9-one:
$^1$H NMR (CDCl$_3$, 400 MHz): δ8.61 (dd; J=1.5 & 5 Hz; α-H of pyridine); 7.35 (dd; J=5 & 7.5 Hz; β-H of pyridine); 7.32–7.85 (other aromatic protons);
IR: 1730 cm$^{-1}$ (C=O)

EXAMPLE 13

7-Bromo-3-azafluoren-9-one:
$^1$H NMR (CDCl$_3$, 400 MHz): δ8.89 (d; J=1 Hz; H4); 8.72 (d; J=5 Hz; H2); 7.84 (d; J=2 Hz; H8); 7.68 (dd; J=2 & 8 Hz; H6); 7.52 (d; J=8 Hz; H5); 7.49 (dd; J=1 & 5 Hz; H1)
IR: 1730 (C=O)

EXAMPLE 14

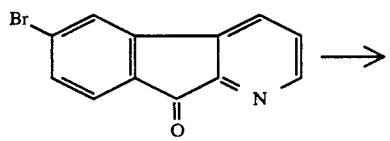

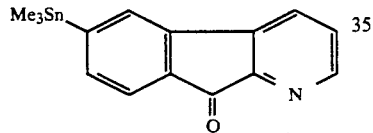

6-Trimethylstannyl-4-azafluoren-9-one:
A mixture of 300 mg (1.17 mmole) of 6-bromo-4-aza-9-fluorenone, 0.250 mL (1.29 mmole) of hexamethylditin, 67 mg (0.058 mmole) of tetrakis-(triphenylphosphine) palladium, and 9.2 mg (0.035 mmole) of triphenylphosphine in 6 mL of toluene was heated 2 hours under reflux. The resulting dark reaction mixture was cooled, diluted with ethyl acetate and washed with 10% sodium bicarbonate and saturated sodium chloride solution. After drying over anhydrous magnesium sulfate, solvent was removed in vacuo and the residue was purified on silica gel using 1:6 ethyl acetate:hexane mixture as eluant to give the desired 6-trimethylstannyl-4-aza-9-fluorenone as cream colored solid.

$^1$H NMR (CDCl$_3$, 400 MHz): δ8.55 (dd; J=1.5 & 5 Hz; α-H of pyridine); 7.12–8.0 (other 5 aromatic protons); 0.32 (9H; Sn(CH$_3$)$_3$)
IR: 1720 cm$^{-1}$ (C=O)

Using the procedure described in Example 14, the following compounds were prepared from the appropriate starting materials.

EXAMPLE 15

7-Trimethylstannyl-4-azafluoren-9-one:
$^1$H NMR (CDCl$_3$, 400 MHz): δ8.59 (dd; 1.5 & 5 Hz; α-H of pyridine); 7.14–7.92 (other aromatic protons); 0.34 (Me$_3$Sn)

EXAMPLE 16

7-Trimethylstannyl-1-azafluoren-9-one:
$^1$H NMR (CDCl$_3$, 400 MHz): δ8.56 (dd; J=1.5 & 5 Hz; α-H of pyridine); 7.82 (dd; J=1.5 & 7.5 Hz) γ-H of pyridine); 7.31 (dd; J=5 & 7.5 Hz; β-H of pyridine) 7.45–7.87 (other aromatic protons); 0.03 (s; SnMe$_3$).

EXAMPLE 17

7-Bromo-3-azafluoren-9-one:
$^1$H NMR (CDCl$_3$, 400 MHz): δ8.87 (d; J=1 Hz; H4); 8.68 (d; J=5 Hz; H2); 7.86 (d; J=<1 Hz; H8); 7.68 (dd; J=<1 & 7 Hz); 7.58 (d; J=7 Hz); 7.52 (dd; J=1 & 5 Hz); 0.31 (s; SnMe$_3$).
IR: 1725 cm$^{-1}$ (C=O)

EXAMPLE 18

8-Bromo-4-azafluoren-9-one:
$^1$H NMR (CDCl$_3$, 400 MHz): δ0.32 (s; SnMe); 8.59 (dd; J=1.5 & 5 Hz; H3); 7.85 (dd; J=1.5 & 7.5 Hz; H1); 7.5, 7.59 & 7.79 (H5, H6 & H7); 7.18 (dd; J=5 & 7.5 Hz; H2)

EXAMPLE 19

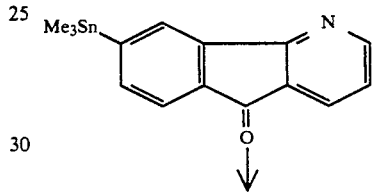

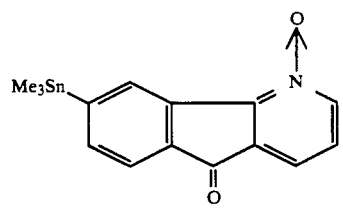

6-Trimethylstannyl-4-oxo-4-aza-9-fluorenone:
345 mg (2 mmole) of m-chloroperbenzoic acid was added to a stirred mixture of 344 mg (1 mmole) of 6-trimethylstannyl-4-aza-9-fluorenone, 8 mL of 1 molar sodium bicarbonate solution, and 15 mL of methylene chloride at room temperature. This mixture was stirred 3 hours, and 20 mL of 5% sodium thiosulfate was added. After stirring 2 hours further, the reaction mixture was diluted with ethylacetate. The organic phase was washed with saturated sodium chloride, and dried over anhyd. magnesium sulfate. Solvent removal afforded a crude product which was purified on silica gel using 3% CH$_3$OH in ethyl acetate as eluant to give the desired N-oxide as yellow solid.

$^1$H NMR (CDCl$_3$, 400 MHz): δ8.75 (s; H5); 8.21 & 7.51 (d's; J=~7 Hz; H1 & H3); 7.63 & 7.68 (d's; J=~7.5 Hz; H7 & H8); 7.19 (dd; J=7 & 7 Hz; H2)

Using the procedure described in Example 19, the following compound was prepared from the appropriate starting materials.

EXAMPLE 20

7-Trimethylstannyl-4-oxo-4-aza-9-fluorenone:
$^1$H NMR (CDCl$_3$, 400 MHz): δ7.89 (s; H8); 8.5 & 7.76 (d's; J=7 Hz; H5 & H6) 8.28 & 7.5 (dd's; J=1 & 7.5 Hz; H1 & H3); 7.2 (dd; J=7.5 & 7.5 Hz; H2); 0.3 (s; SnMe$_3$)

EXAMPLE 21

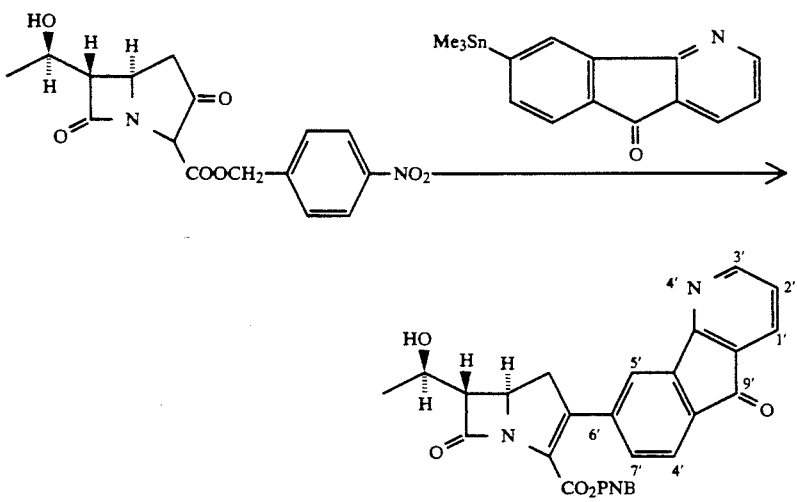

EXAMPLE 23 p-Nitrobenzyl (5R,6S)-2-[7'-(1'-azafluoren-9'-onyl)]-6-[(1R)-1-hydroxyethyl]carbapen-2-em-3-carboxylate ¹H NNR (CDCl₃, 400 MHz): δ1.37 (d; J=~7 Hz; CH₃); 3.31 (dd; J=3 & 6.5 Hz; H6); 3.2–3.39 (m; H1); 4.29 (m; H8); 4.35 (ddd; J=3, 9 & 10 Hz; H5); 5.15–5.40 (m; OCH₂); 8.61 (dd; J=1 & 5 Hz; α-H of pyridine); 7.26–8.16 (aromatic protons)

EXAMPLE 24 p-nitrobenzyl(5R,6S)-2-[7'-(3'-azafluoren-9'-onyl)]-6-[(1R)-1-hydroxyethyl]carbapen-2-em-3-carboxylate ¹H NMR (D₆-DMSO, 400 MHz): δ1.17 (d; J=~8 Hz; CH₃); 3.45 (dd; J=3 & 6 Hz; H6); 3.14–3.62 (m; OCH₂); 3.99 (m; H8); 4.25 (m; H5); 9.1 (s; H4 of fluorenone); 8.72 (d; J=5 Hz; H2 of fluorenone); 7.48–8.08 (other aromatic protons)

IR (CH₂Cl₂): 1780 cm⁻¹ (β-lactam C=O); 1730 (other C=O)

EXAMPLE 25 p-Nitrobenzyl (5R,6S)-2-[6'-(4'-oxo-4'-azafluoren-9'-onyl)]-6-[(1R)-1-hydroxyethyl]carbapen-2-em-3-carboxylate ¹H NMR (CDCl₃, 400 MHz): δ1.35 (d; J=~8 Hz; CH₃); 3.35 (dd; J=3 & 6.5 Hz; H6); 3.23–3.46 (m; H1); 4.30 (m; H8); 4.38 (m; H5); 8.52 (d; J=~1 Hz; H3 of fluorenone); 7.18–8.22 (other aromatic protons)

EXAMPLE 26 p-Nitrobenzyl (5R,6S)-2-[7'-(4'-oxo-4'-aza-9'-fluorenonyl)]-6-[(1R)-1-hydroxyethyl]carbapen-2-em-3-carboxylate ¹H NMR (D₆-DMSO, 400 MHz): δ1.18 (d; J=~8 Hz; CH₃); 3.47 (dd; J=2.5 & 6 Hz; H6); 3.14–3.64 (m; H1); 4.01 (m; H8); 4.26 (m; H5); 5.27 (OCH₂); 8.37 (dd; J=1 & 6.5 Hz; fluorenone proton); 7.4–8.3 (other aromatic protons)

EXAMPLE 27 p-Nitrobenzyl (5R,6S)-2-[8'-(4'-azafluoren-9'-onyl)]-6-[(1R)-1-hydroxyethyl]-carbapen-2-em-3-carboxylate ¹H NMR (CDCl₃, 400 MHz): δ1.37 (d; J=~8 Hz; CH₃); 3.46 (dd; J=2.5 & 6 Hz; H6); 3.11–3.55 (m; H1); 4.31 (m; H8); 4.46 (m; H5); 7.1–8.1 (aromatic protons); 8.59 (dd; J=1.5 & 5 Hz; H3 of fluorenone)

--- p-Nitrobenzyl (5R,6S)-2-[6'-(4'-azafluoren-9'-onyl)]-6-[(1R)-1-hydroxyethyl)-carbapen-2-em-3-carboxylate 0.093 mL (0.66 mmole) of dry diisopropylamine was added to a stirred solution of 209 mg (0.6 mmole) p-nitrobenzyl (5R,6S)-2-oxo-6-[(1R)-1-hydroxyethyl]-carbapenam-3-carboxylate in 2.5 mL of dry tetrahydrofuran at −78° under nitrogen after stirring 10 mins., 0.11 mL (0.66 mmole) of trifluoromethane sulfonic anhydride was added and the mixture was stirred for 0.5 hr. 2.5 mL of 1-methyl-2-pyrrolidinone, 10.38 mg (0.01 mmole) of tris-(dibenzylidenacetone)-bis-palladium (0) chloroform complex, 172 mg (0.5 mmole) of 6-(trimethylstannyl)-4-azafluoren-9-one, and 69 mg (0.5 mmole) of diisopropylamine hydrochloride were added and the reaction mixture was then quickly warmed to room temperature using water bath. The reaction mixture was then stirred 2 hours at room temperature during which much of the hydrochloride dissolved. After stirring 2.5 hours more, the reaction mixture was diluted with ethyl acetate and washed several times with saturated sodium chloride. The organic phase was dried over anhydrous magnesium sulfate. Solvent removal gave a residue, which was dissolved in minimum amount of methylene chloride. Excess ether was added to this solution and a brick red solid precipitated. It was identified as the desired carbapenem ester.

¹H NMR (CDCl₃, 400 MHz): δ1.38 (d; CH₃); 3.3 (dd; J=2.5 & 7 Hz; H6;) 4.37 (ddd, J=2.5, 3 & 9 Hz; H5); 5.15–5.28 (CH₂O); 8.58 (dd; J=1 & 5 Hz; α-H of pyridine); 7.2–8.08 (aromatic H's);

IR: 1780 cm⁻¹ (β-Lactam C=O); 1720 (fluorenone & ester C=O);

Using the procedure described in Example 21, the following compounds were prepared from the appropriate starting materials.

EXAMPLE 22 p-Nitrobenzyl (5R,6S)-2-[7'-(4'-azafluoren-9'-onyl)]-6-[(1R)-1-hydroxyethyl]carbapen-2-em-3-carboxylate ¹H NMR (CDCl₃, 400 MHz): δ1.38 (d; J=~7 Hz; CH₃); 3.2–3.4 (m; H1); 3.3 (dd; J=2.5 & 7 Hz; H6); 4.28 (m; H8); 4.34 (ddd; J=2.5, 9 & 9.5 Hz; H5); 5.14–5.36 (CH₂); 8.62 (dd; J=1.5 & 5 Hz; α-H of pyridine); 7.2–8.12 (other aromatic protons)

EXAMPLE 28

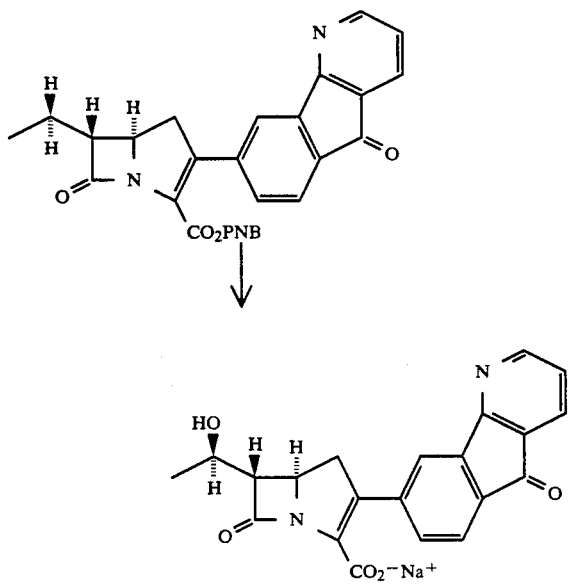

Sodium(5R,6S)-2-[6'-(4'-azafluoren-9'-only)]-6-[(1R)-1-hydroxyethyl]-carbapen-2-em-3-carboxylate A suspension of 135 mg (0.264 mmole) of p-nitrobenzyl (5R,6S)-2-[6'-(4'-azafluoren-9'-only)]-6-[(1R)-1-hydroxyethyl]carbapen-2-em-3-carboxylate, 14 mg of 10% palladium on carbon catalyst, and 0.3 mL (0.3 mmole) of 1 molar solution of sodium bicarbonate solution in 10 mL of 1:2 mixture of water and tetrahydrofuran was stirred under an atmosphere of hydrogen in a balloon for 1.5 hours at room temperature. The solution turned dark yellow. It was filtered through a bed of celite which was then washed with water. The combined filtrates were concentrated and freeze dried. This crude lyophilizate was taken up in 2 mL of water and applied to reverse phase silica gel plates which were eluted with 1:5 mixture of acetonitrile:water. U.V. active area was scraped and stirred in 4:1 mixture of acetonitrile:water. Solid was filtered and washed with the same solvent. The combined filtrates were washed four times with hexane, concentrated, and freeze dried to give the desired sodium salt as yellow orange fluffy mass.

$^1$H NMR (D$_2$O), 400 MHz: δ1.33 (d; J=~7 Hz; CH$_3$); 3.1–3.52 (m; H1); 3.58 (dd; J=2.5 & 6Hz; H6); 4.29 (m, H8); 4.4 (ddd; J=2–5, 9 & 9.5 Hz; H5); 8.4 (α-H of pyridine); 7.78 (γ-H of pyridine); 7.28–7.42 (m; other aromatic protons)

UV: λ$_{max}$$^{water}$: 313 nm; (ε$_{ext}$=6686)

IR: 1715 cm$^{-1}$ (ketone & acid C=O); 1760 (β-lactam C=O)

Using the procedure described in Example 28, the following compounds were prepared from the appropriate starting materials.

EXAMPLE 29

Sodium(5R,6S)-2-[7'-(4'-azafluoren-9'-only]-6-[(1R)-1-hydroxyethyl']-carbapen-2-em-3-carboxylate

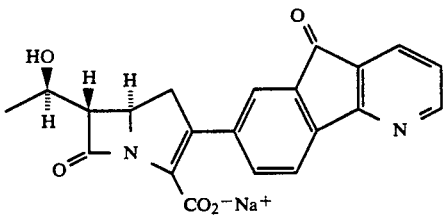

$^1$H-NMR (D$_2$O, 400 MHz): δ1.33 (d; J=~7 Hz; CH$_3$); 3.06–3.54 (m; H1); 3.55 (dd, J=2.5 & 6 Hz; H6); 4.28 (m; H8); 4.38 (ddd; J=2.5, 9 & 9 Hz; H5); 8.38 (dd; J=1.5 & 5 Hz; α-H of pyridine); 7.81 (dd; J=1.5 & 7.5 Hz; γ-H of pyridine); 7.26–7.49 (other aromatic protons);

UV: λ$_{max}$$^{water}$: ~300 nm(ε:6722) & 338 nm

EXAMPLE 30

Sodium (5R,6S)-2-[7'-(1'-azafluoren-9'-only)]6-[(1R)-1-hydroxyethyl]-carbapen-2-em-3-carboxylate

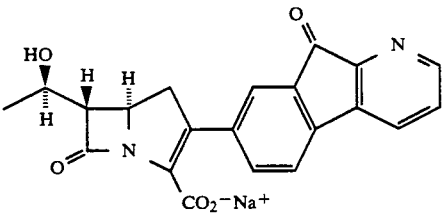

$^1$H-NMR (D$_2$O, 400 MHz): δ1.33 (d; J=~7 Hz; CH$_3$); 3.05–3.5 (H1); 3.53 (H6); 4.28 (H8); 4.35 (H5); 8.33 (α-H of pyridine); 7.3–7.85 (other aromatic protons);

UV: λ$_{max}$$^{water}$: 303 (ε=7164); 331 (ε=11462)

EXAMPLE 31

Sodium (5R,6S)-2-[7'-(3'-azafluoren-9'-only)-6-[(1R)-1-hydroxyethyl]carbapen-2-em-3-carboxylate

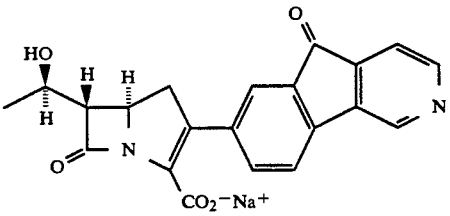

$^1$H-NMR (D$_6$-DMSO, 400 MHz): δ1.15 (d; J=~8 Hz; CH$_3$); 3.93 (m; H8); 4.08 (m; H5); 9.07 (s; H4 of fluorenone) 8.67 (d; J=~5 Hz; H2 of fluorenone); 7.84 (s; H8 of fluorenone); 7.8 (d; J=8 Hz; fluorenone proton); 7.69 (dd; J=1 & 8 Hz; fluorenone proton); 7.53 (dd; J=1 & 5 Hz; H1 of fluorenone)

UV: λ$_{max}$$^{water}$: 305 (ε:7482)

EXAMPLE 32

Sodium (5R,6S)-2-[8'-(4'-azafluoren-9'-only)]-6-[(1R)-1-hydroxyethyl]carbapen-2-em-3-carboxylate

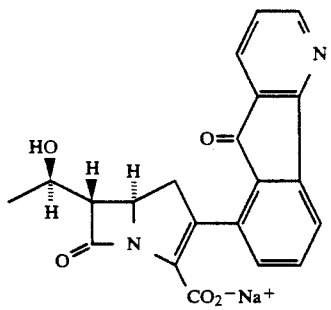

$^1$H-NMR (D$_2$O, 400 MHz); δ1.35 (d; J=~8 Hz; CH$_3$); 3.59 (dd; J=3 & 6 Hz; H6); 3.0–3.53 (m; H1); 4.32 (m; H8); 4.4 (m; H5); 8.45 (dd; J=1.5 & 5.5 Hz; H3 of fluorenone); 7.26–7.87 (other fluorenone protons)

UV: λ$_{max}^{water}$=290 (ε:2229)

EXAMPLE 33

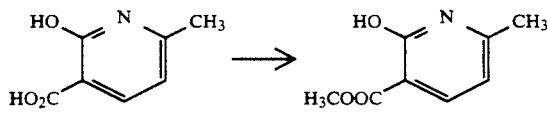

Methyl 2-hydroxy-6-methyl-nicotinate:

Excess diazomethane in ether was added portionwise over 15 mins to 9.58 g (~60 mmoles) of 2-hydroxy-6-methyl nicotinic acid in 900 mL of THF at 0°. After stirring 2 hours, excess diazomethane was removed in vacuo. The resulting white solid was filtered and washed with hexane and dried. This fluffy solid was the required methyl ester. The filtrate was concentrated. The resulting solid was redissolved in a minimum amount of THF and hexane was added until no further precipitation was observed. Solid was filtered and washed with hexane and dried to provide more of the desired compound.

EXAMPLE 34

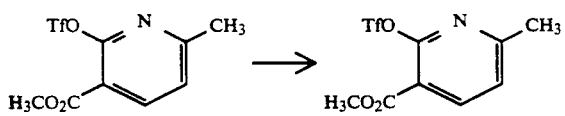

Methyl 2-trifluoromethanesulfonyloxy-6-methyl-nicotinate

Triethylamine (1.54 g, 11 mmoles) was added to a suspension of 1.67 g (10 mmoles) of 2-hydroxy-6-methyl nicotinic acid in 20 mL of methylene chloride under nitrogen at 0°. 1.86 mL of triflic anhydride (1.86 mL, 11 mmoles) was then added dropwise. After stirring one hour, the reaction mixture was diluted with excess ether and washed with water three times. The organic phase was dried over anhydrous magnesium sulfate. Solvent removal in vacuo gave the desired triflate as light brown liquid.

EXAMPLE 35

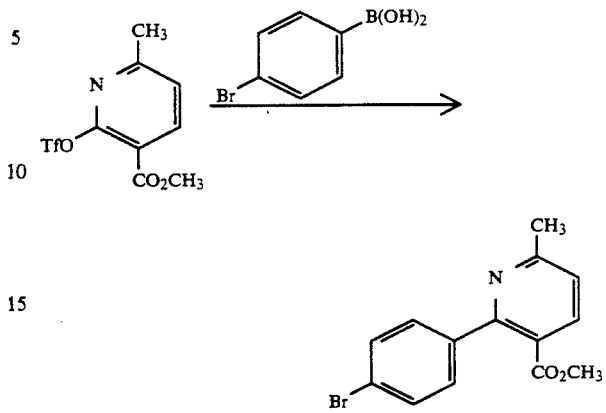

Methyl 2-(4'-bromophenyl)-6-methyl nicotinate

A mixture 4-bromophenylboronic acid (2.01 g; 10 mmoles), methyl 2-trifluoromethanesulfonyloxy-6-methyl nicotinate (3.1 G; 10 mmoles), tetrakis-(triphenylphosphine)palladium (300 mg; 0.26 mmoles), and sodium carbonate solution, (10 mL of 2 molar solution; 20 mmoles) in 30 mL of 1,2-dimethoxyethane was heated to reflux 8 hrs. under nitrogen. The reaction mixture was cooled, solvent was removed, and the residue was taken up in ethyl acetate and washed three times with water. The organic phase was dried over anhydrous magnesium sulfate. Solvent was removed to give a crude product which was purified on silica gel using 1:6 mixture of ethyl acetate:hexane as solvent. The desired product was obtained as white oil, which solidified.

EXAMPLE 36

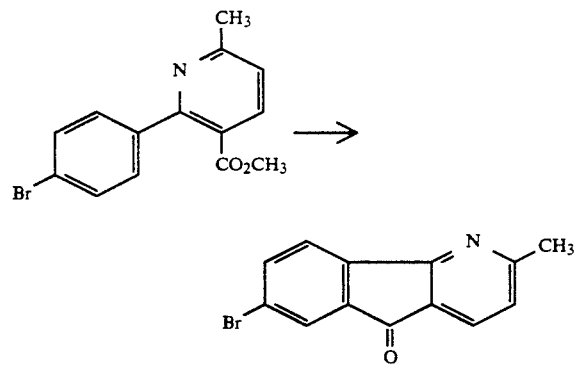

3-Methyl-7-bromo-4-aza-9-fluorenone

A mixture of 2.38 g (7.8 mmoles) of methyl 2-(4'-bromophenyl)-6-methyl nicotinate and 70 gm of polyphosphoric acid was heated 4 hrs at 220° and 30 mm pressure. When the reaction mixture was still warm, ice was cautiously added. After the ensuing vigorous reaction subsided upon further cautious addition of ice, the reaction mixture was diluted to ~600 mL with ice water. 5N sodium hydroxide solution was slowly added until the pH of the reaction mixture was 8–9. Solid was filtered and washed with water. Solid was then dissolved in chloroform and filtered through a bed of wet silica gel in chloroform. The filtrate was concentrated to give the desired product as a yellow solid.

EXAMPLE 37

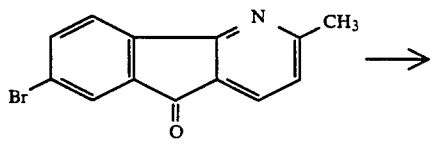

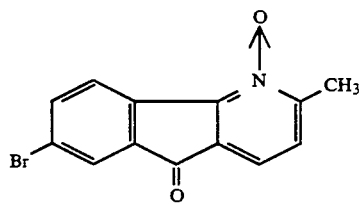

3-Methyl-4-oxo-7-bromo-4-aza-9-fluorenone:

1.376 g (8 mmoles) of m-chloroperbenzoic acid was added to a stirring suspension of 3-methyl-7-bromo-4-aza-9-fluorenone (1.1 g; 4 mmoles) and 30 mL of 1 molar sodium bicarbonate solution in 60 mL of methylene chloride. This mixture was stirred 5 hrs at room temperature 10% sodium thiosulfate solution was added, and the mixture was stirred 2 hours more. It was then extracted with methylene chloride. The organic phase was dried over anhydrous MgSO₄. Solvent removal gave the desired N-oxide as yellow amorphous solid.

EXAMPLE 38

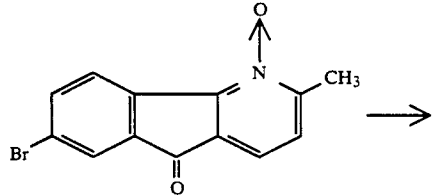

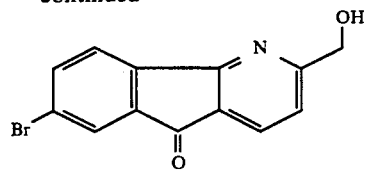

3-Hydroxymethyl-7-bromo-4-aza-9-fluorenone

A mixture of 1.1 g of 4-oxo-3-methyl-7-bromo-4-aza-9-fluorenone and 15 mL of trifluoroacetic anhydride in 3 mL of methylene chloride was heated to reflux 3 hrs. reaction mixture was cooled and excess 10% sodium bicarbonate solution was added cautiously. The reaction mixture was stirred 6 hrs at room temperature and the resulting solid was filtered and dried to afford the desired product as yellow solid.

EXAMPLE 39

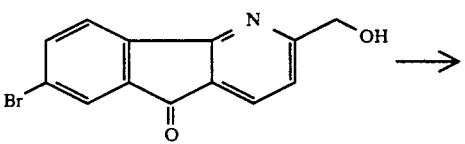

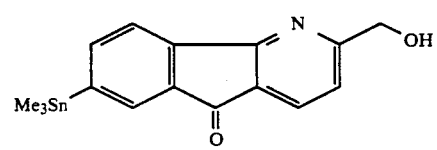

3-Hydroxymethyl-7-trimethylstannyl-4-aza-9-fluroenone

A mixture of 3-hydroxymethyl-7-bromo-4---fluorenone (657 mg, 2.258 mmole), hexamethylditin (428 µl, 2.5 mmole), tetrakis-(triphenylphosphine)palladium (144 mg, 0.125 mmole), and triphenylphosphine (18 mg, 0.068 mmoles) in 12.5 mL of toluene was heated 2 hrs to reflux. The resulting dark reaction mixture was cooled, diluted with ethyl acetate and washed with 10% sodium bicarbonate solution. The organic phase was dried over anhydrous MgSO₄ solvent removal gave a crude product, which was purified on silica gel using 1:1 mixture of ethyl acetate:hexane as solvent to give the desired product as yellow solid.

EXAMPLE 40

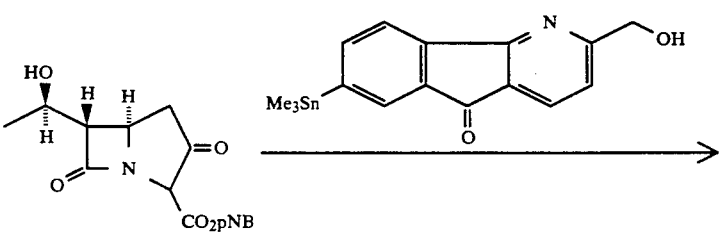

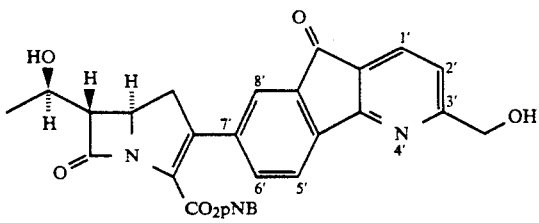

p-Nitrobenzyl (5R, 6S)-2-[7'-(3'-hydroxymethyl-4'-azafluoren-9'-anyl)]-6-[(1R)-1-hydroxyethyl)]carbapen-2-en-3-carboxylate Employing the procedure described in Example 21 but substituting the 3-hydroxymethyl-7-trimethylstannyl-4-azafluoren-9-one (prepared as described in Example 39) for the stannyl fluorenone employed in Example 21 provides the title compound.

EXAMPLE 41

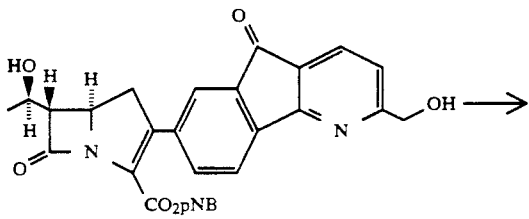

Sodium (5R, 6S)-2-[7'-(3'-hydroxymethyl-4'-azafluoren-9'-onyl)]-6-[(1R)-1-hydroxyethyl]carbapen-2-en-3-carboxylate Following the procedure described in Example 28, but substituting the protected carbapenem prepared as described in Example 40 provides the title compound.

EXAMPLE 42

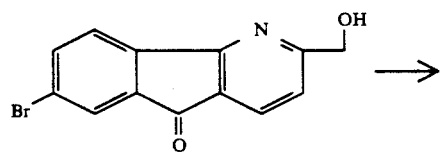

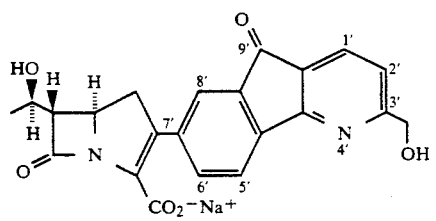

3-Formyl-7-bromo-4-aza-9-fluorenone 150 mg of finely powdered 3 Å molecular sieves, 350 mg (3 mM) of N-methylmorpholine n-oxide, and 70 mg (0.2) of tetrapropylammonium perrhuthenate are added. To a solution of 576 mg (2 mM) of the carbinol, 3-hydroxymethyl-7-bromo-4-aza-9-fluorenone, prepared as described in Example 38, in 20 mL of dry methylene chloride under nitrogen at R.T. the reaction mixture is stirred 15 minutes, diluted with 20 mL of ethyl acetate and filtered through a bed of silica gel, which is washed further with ethyl acetate 5 times. The combined filtrates are concentrated to give the desired aldehyde as yellow solid.

EXAMPLE 43

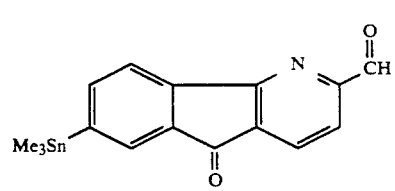

3-Formyl-7-trimethylstannyl-4-aza-9-fluorenone

Following the procedure described in Example 46 but substituting the formyl azafluorenone prepared as described in Example 42 provides the title compound.

EXAMPLE 44

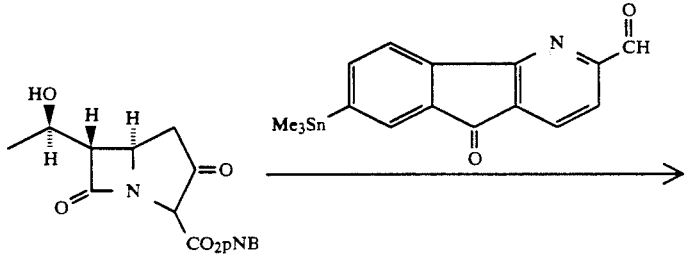

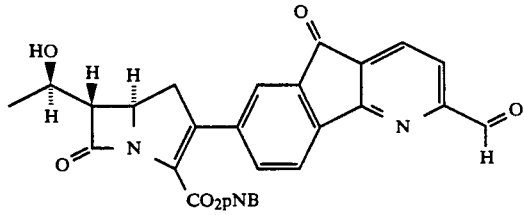

p-Nitrobenzyl (5R,6S)-2-[7'-(3'-formyl-4'-azafluoren-9'-onyl)]-6-[(1R)-1-hydroxyethyl)]carbapen-2-em-3-carboxylate Employing the procedure described in Example 21, but substituting the 3-formyl-7-trimethylstannyl-4-azafluoren-9-one (prepared as described in Example 43) for the stannyl azafluoreneone employed in Example 21 provides the title compound.

EXAMPLE 45

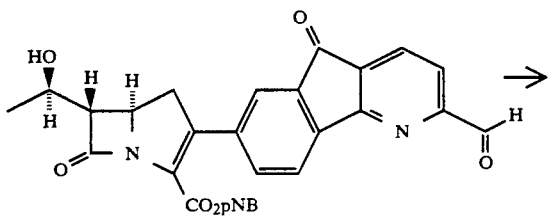

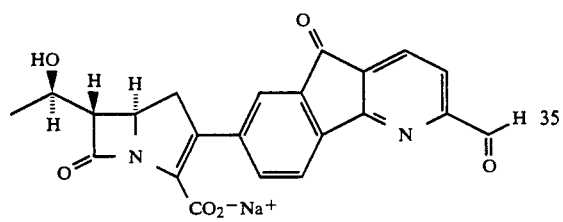

Sodium (5R,6S)-2-[7'-(3'-formyl-4'-azafluoren-9'-onyl)]-6-[(1R)-1-hydroxyethyl]carbapen-2-em-3-carboxylate Following the procedure described in Example 28, but substituting the protected carbapenem prepared as described in Example 44 provides the title compound.

EXAMPLE 46

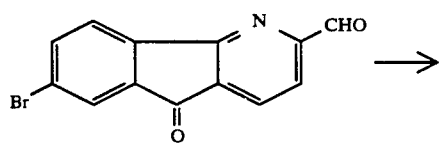

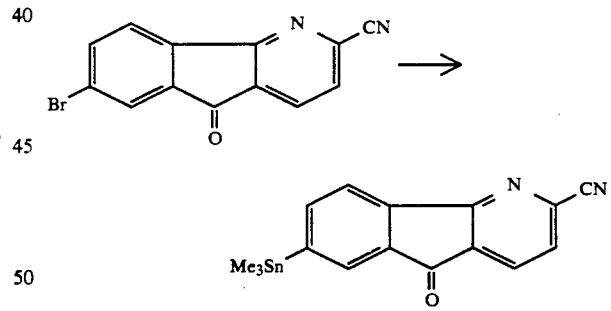

3-Cyano-7-bromo-4-aza-9-fluorenone

A mixture of 286 mg (1 mmole) of 3-formyl-7-bromo-4-aza-9-fluorenone (prepared as described in Example 42), 85 mg (1.2 mmole) of hydroxylamine hydrochloride in ~2 mL of pyridine is stirred overnight at R.T. Ethyl acetate and excess sodium bicarbonate solution are then added and the precipitated solid precipitate is filtered and dried to give 3-oximinomethyl-7-bromo-4-aza-9-fluorenone.

2 Equivalents of triethylamine are added to a suspension of the oxime in dry methylene chloride at −78° under nitrogen. 1.1 equivalent of triflic anhydride are then added dropwise over 3 minutes. After stirring overnight, the reaction mixture is diluted with ethyl acetate and washed with 10% sodium bicarbonate solution. The organic phase is dried over anhydrous magnesium sulfate. Solvent removal provides the desired 3-cyano-7-bromo-4-aza-9-fluorenone.

EXAMPLE 47

3-Cyano-7-trimethylstannyl-4-aza-9-fluorenone

Following the procedure described in Example 46 but substituting the cyano azafluorenone prepared as described in Example 46 provides the title compound.

EXAMPLE 48

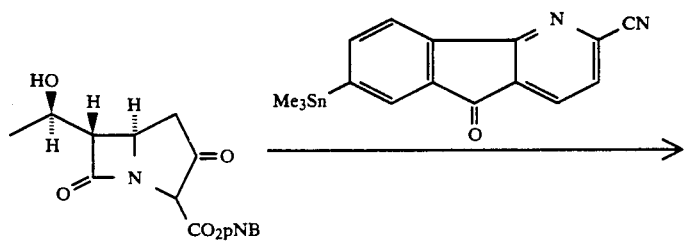

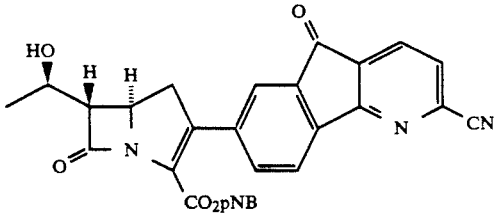

p-Nitrobenzyl (5R,6S)-2-[7'-(3'-cyanomethyl-4'-azafluoren-9'-onyl)]-6-[(1R)-1-hydroxyethyl)]carbapen-2-em-3-carboxylate Employing the procedure described in Example 21 but substituting the 3-cyano-7-trimethylstannyl-4-azafluoren-9-one (prepared as described in Example 47) for the stannyl azafluorenone employed in Example 21 provides the title compound.

EXAMPLE 49

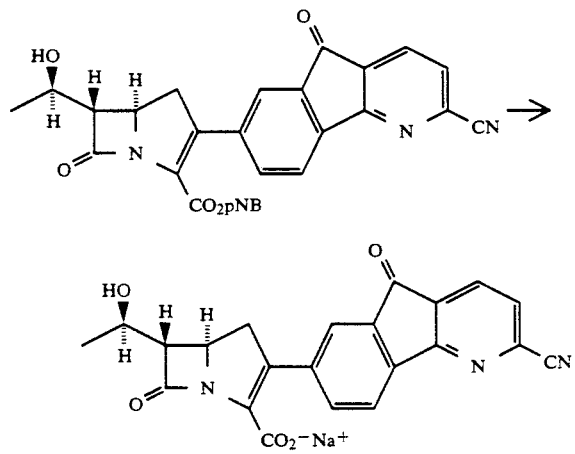

Sodium (5R,6S)-2-[7'-(3'-cyano-4'-azafluoren-9'-onyl)]-6-[(1R)-1-hydroxyethyl]carbapen-2-em-3-carboxylate Following the procedure described in Example 28, but substituting the protected carbapenem prepared as described in Example 48 provides the title compound.

EXAMPLE 50

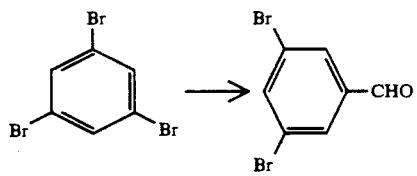

3,5-Dibromobenzaldehyde

A mixture of 15.7 g (50 mmoles) of 1,3,5-tribromobenzene and 1.344 g (56 mmoles) of magnesium in 200 mL of THF was stirred 5 hrs. At room temperature 7.5 mL (100 mmoles) of DMF was then added at 0° and the reaction mixture was stirred overnight. Solvent was removed in vacuo at room temperature the residue was taken up in 200 mL of ethyl acetate and washed with 6×50 mL of satd. sodium chloride soln. The organic phase was dried over anhyd. MgSO$_4$. Solvent was removed to give a crude solid, which was dissolved in minimum amount of methylene chloride, and applied on silica gel. Elution with 1:9 mixture of ether:hexane mixture containing 3% methylene chloride gave the desired 3,5-dibromobenzaldehyde as white solid.

EXAMPLE 51

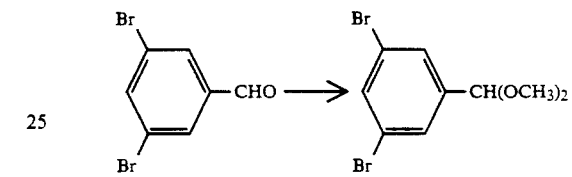

3,5-Dibromo-(dimethoxymethyl)benzene

A mixture of 13.2 g (50 mmoles) of crude 3,5-dibromobenzaldehyde, 2 mL (50 mmoles) of methanol, and 100 mg of p-toluenesulfonic acid in 100 mL of 2,2-dimethoxypropane was heated to reflux 6 hrs. After cooling, solvent was removed in vacuo to give a brown oil. This was applied on silica gel and washed with 1:20 ethylacetate:hexane mixture. The filtrate was concentrated to orange brown oil of the desired acetal.

$^1$H NMR (CDCl$_3$, 400 MHz): $\delta$7.60(dd, J$_1$=2 Hz; J$_2$=1.5 Hz; aromatic H, 1H); 7.53 (d; J=~2 Hz; aromatic H's; 2H); 5.21 (s; CH(O)); 3.2 [s; C(OCH$_3$)$_2$; 6H]

EXAMPLE 52

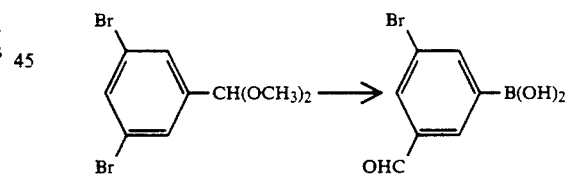

3-Bromo-5-formyl-phenylboronic acid 4.2 mL (10.5 mmoles) of 2.5 m n-butyllithium was added to a solution of 3.1 g (10.5 mmoles) of 3,5-dibromo(dimethoxymethyl)benzene in 50 mL of ether at −78° under nitrogen over a period of 2 minutes. The reaction mixture was stirred 8 minutes and 2.415 mL (10.5 mmoles) of triisopropyl borate was added. The reaction was stirred 5.5 hrs at room temperature after cooling to 0°, 21 mL of 2N hydrochloric acid was added. After stirring 1 hour at room temperature, ether layer was separated and washed with saturated sodium chloride solution. After drying over anhydrous MgSO$_4$, solvent was removed to give a solid, which was triturated with petroleum ether. The resulting solid was dried in vacuo to give the desired boronic acid.

$^1$H NMR (CDCl$_3$, 400 MHz): $\delta$8.09, 8.22, 8.28 (aromatic H's); 9.98 (aldehyde H); 8.23, 8.33 and 8.51 (smaller peaks of anhydride)

EXAMPLE 53

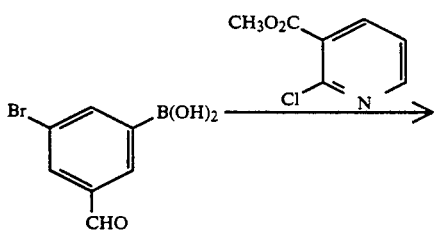

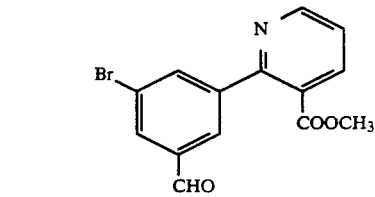

Methyl 2-[3'-bromo-5'-formylphenyl]nicotinate

A mixture of 1.14 g (5 mmoles) of 3-bromo-5-formylphenylboronic acid, 1.715 g (10 mmoles) of methyl 2-chloro-nicotinate, 100 mg of tetrakis-(triphenyl phosphine)palladium, 2.5 mL of ethanol, 10 mL of 2M sodium bicarbonate solution, and 10 mL of toluene was heated 20 hrs at 80° under nitrogen. After diluting with ethyl acetate, the reaction mixture was washed with saturated NaCl solution. The organic phase was dried over anhydrous $MgSO_4$. Solvent removal gave a crude product which was purified on silica using ethyl acetate:hexane mixture as solvent to give the desired product as a solid.

EXAMPLE 54

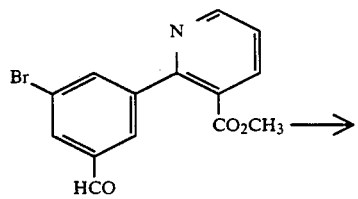

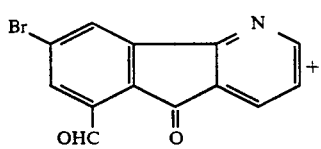

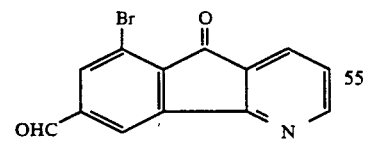

6-Bromo-8-formyl-4-aza-9-fluorenone:

A mixture of 1 g of methyl-2-(3'-bromo-5'-formylphenyl) nicotinate and 30 g of polyphosphoric acid was heated 4 hrs at 220° and ~30 mm pressure. Ice was cautiously added. After the ensuing vigorous reaction subsided, more ice was cautiously added. 5N Sodium hydroxide solution was slowly added until the pH of the reaction mixture was 8–9. The solid which precipitated was filtered and dried. The solid was dissolved in chloroform and applied on silica gel and eluted with a mixture of ethyl acetate:hexane to give the desired azafluorenone and its regioisomer.

EXAMPLES 55 and 56

Employing the procedures described in Examples 43–49 but substituting the 6-bromo-8-formyl-4-azafluoren-9-one prepared as described in Example 54, for the 3-formyl-7-bromo-4-azafluoren-9-one, provides the following compounds.

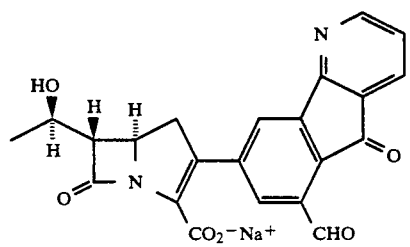

Sodium (5R, 6S)-2-[6'-(8'-formyl-4'-aza-fluoren-9-onyl)]-6-[(1R)-1-hydroxyethyl]carbapen-2-em-3-carboxylate

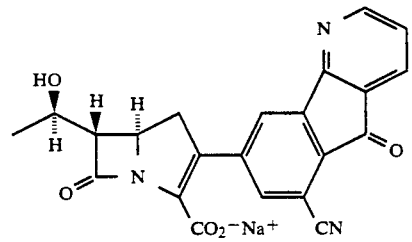

Sodium (5R, 6S)-2-[6'-(8'-cyano-4'-aza-fluoren-9-onyl)]-6-[(1R)-1-hydroxyethyl]carbapen-2-em-3-carboxylate

What is claimed is:

1. A compound of the formula:

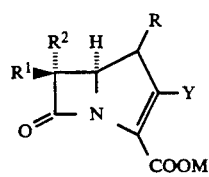

wherein:
Y is:

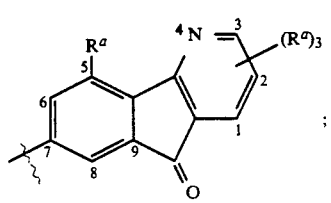

a)

;

61
-continued
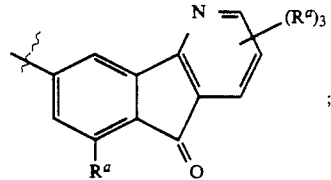 b)
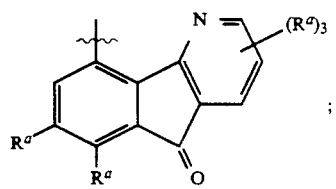 c)
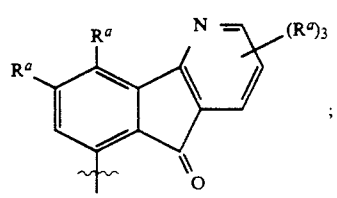 d)
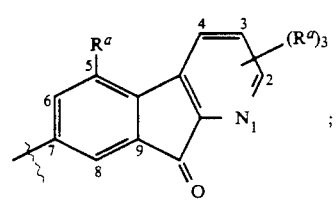 e)
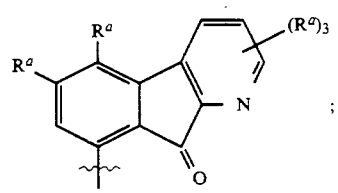 f)
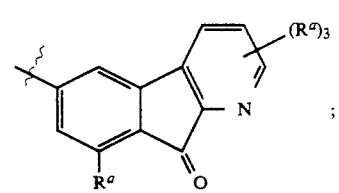 g)
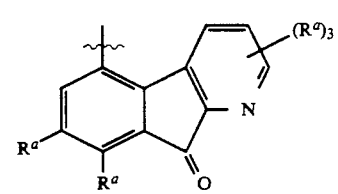 h)
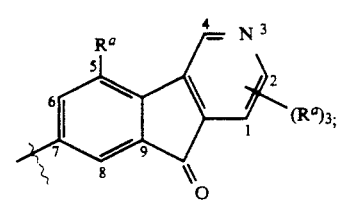 i)
62
-continued
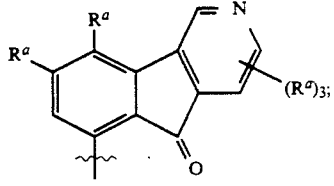 j)
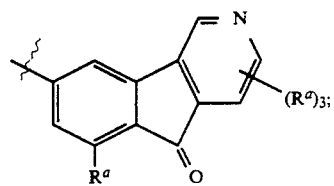 k)
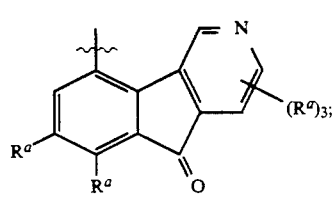 l)
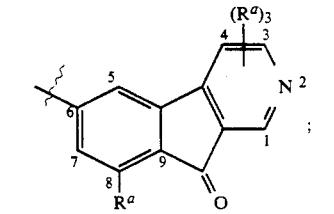 m)
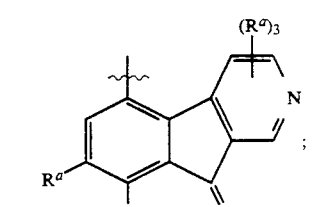 n)
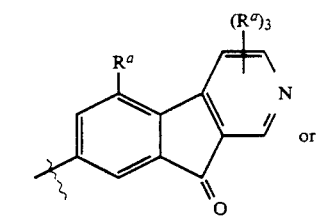 o)
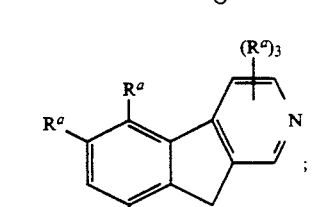 p)
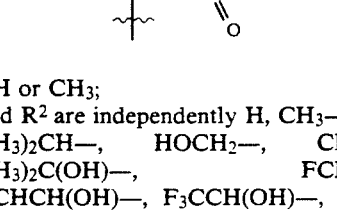
R is H or CH$_3$;
R$^1$ and R$^2$ are independently H, CH$_3$—, CH$_3$CH$_2$—, (CH$_3$)$_2$CH—, HOCH$_2$—, CH$_3$CH(OH)—, (CH$_3$)$_2$C(OH)—, FCH$_2$CH(OH)—, F$_2$CHCH(OH)—, F$_3$CCH(OH)—, CH$_3$CH(F)—, CH$_3$CF$_2$—, or (CH$_3$)$_3$C(F)—;

$R^a$ are independently selected from the radicals set out below, provided that no more than four $R^a$ substituents are other than hydrogen:

a) hydrogen;
b) a trifluoromethyl group: —$CF_3$;
c) a halogen atom: —Br, —Cl, —F, or —I;
d) $C_1$-$C_4$ alkoxy radical: —$OC_{1-4}$ alkyl, wherein the alkyl is optionally mono-substituted by $R^q$, where $R^q$ is a member selected from the group consisting of —OH, —$OCH_3$, —CN, —C(O)$NH_2$, —OC(O)$NH_2$, —CHO, —OC(O)N($CH_3$)$_2$, —$SO_2NH_2$, —$SO_2$N($CH_3$)$_2$, —$SOCH_3$, —$SO_2CH_3$, —F, —$CF_3$, —COOM$^a$, (where M$^a$ is hydrogen, alkali metal, methyl or phenyl), tetrazolyl (where the point of attachment is the carbon atom of the tetrazole ring and one of the nitrogen atoms is mono-substituted by M$^a$ as defined above) and —$SO_3M^b$ (where M$^b$ is hydrogen or an alkali metal);

e) a hydroxy group: —OH;
f) a carbonyloxy radical of formula —O(C=O)$R^s$, where $R^s$ is $C_1$-$C_4$ alkyl or phenyl, each of which is optionally mono-substituted by $R^q$ as defined above;

g) a carbamoyloxy radical of formula —O(C=O)N($R^y$)$R^z$ where $R^y$ and $R^z$ are independently H, $C_{1-4}$ alkyl (optionally mono-substituted by $R^q$ as defined above), together a 3- to 5-membered alkylidene radical to form a ring (optionally substituted with $R^q$ as defined above) or together form a 2- to 4-membered alkylidene radical, interrupted by —O—, —S—, —S(O)— or —S(O)$_2$— to form a ring (where the ring is optionally mono-substituted with $R^q$ as defined above);

h) a sulfur radical: —S(O)$_n$—$R^s$ where n=0-2, and $R^s$ is defined above;

i) a sulfamoyl group; —$SO_2$N($R^y$)$R^z$ where $R^y$ and $R^z$ are as defined above;

j) azido: $N_3$;

k) a formamido group: —N($R^t$)(C=O)H, where $R^t$ is H or $C_{1-4}$ alkyl, and the alkyl thereof is optionally mono-substituted by $R^q$ as defined above;

l) a ($C_1$-$C_4$ alkyl)carbonylamino radical: —N($R^t$)(C=O)$C_{1-4}$ alkyl, where $R^t$ is as defined above, and the alkyl group is also optionally mono-substituted by $R^q$ as defined above;

m) a ($C_1$-$C_4$ alkoxy)carbonylamino radical: —N($R^t$)(C=O)O$C_{1-4}$ alkyl, where $R^t$ is as defined above, and the alkyl group is also optionally mono-substituted by $R^q$ as defined above;

n) a ureido group: —N($R^t$)(C=O)N($R^y$)$R^z$ where $R^t$, $R^y$ and $R^z$ are as defined above;

o) a sulfonamido group: —N($R^t$)$SO_2R^s$, where $R^s$ and $R^t$ are as defined above;

p) a cyano group: —CN;

q) a formyl or acetalized formyl radical: —(C=O)H or —CH(O$CH_3$)$_2$;

r) ($C_1$-$C_4$ alkyl)carbonyl radical wherein the carbonyl is acetalized: —C(O$CH_3$)$_2C_{1-4}$ alkyl, where the alkyl is optionally mono-substituted by $R^q$ as defined above;

s) carbonyl radical: —(C=O)$R^s$, where $R^s$ is as defined above;

t) a hydroximinomethyl radical in which the oxygen or carbon atom is optionally substituted by a $C_1$-$C_4$ alkyl group: —(C=NO$R^z$)$R^y$ where $R^y$ and $R^z$ are as defined above, except they may not be joined together to form a ring;

u) a ($C_1$-$C_4$ alkoxy)carbonyl radical: —(C=O)O$C_{1-4}$ alkyl, where the alkyl is optionally mono-substituted by $R^q$ as defined above;

v) a carbamyl radical: —(C=O)N($R^y$)$R^z$ where $R^y$ and $R^z$ are defined above;

w) an N-hydroxycarbamoyl or N($C_{1-4}$ alkoxy)carbamoyl radical in which the nitrogen atom may be additionally substituted by a $C_1$-$C_4$ alkyl group: —(C=O)-N(O$R^y$)$R^z$ where $R^y$ and $R^z$ are as defined above, except they may not be joined together to form a ring;

x) a thiocarbamoyl group: —(C=S)N($R^y$)$R^z$ where $R^y$ and $R^z$ are as defined above;

y) carboxyl: —COOM$^b$, where M$^b$ is as defined above;

z) thiocyanate: —SCN;

aa) trifluoromethylthio: —$SCF_3$;

ab) tetrazolyl, where the point of attachment is the carbon atom of the tetrazole ring and one of the nitrogen atoms is mono-substituted by hydrogen, an alkali metal or a $C_1$-$C_4$ alkyl optionally substituted by $R^q$ as defined above;

ac) an anionic function selected from the group consisting of:
phosphono [P=O(OM$^b$)$_2$;
alkylphosphono {P=O(OM$^b$)-[O($C_1$-$C_4$ alkyl)]};
alkylphosphinyl [P=O(OM$^b$)-($C_1$-$C_4$ alkyl)];
phosphoramido [P=O(OM$^b$)N($R^y$)$R^z$ and P=O(OM$^b$)NH$R^x$];
sulfino (SO$_2$M$^b$);
sulfo (SO$_3$M$^b$);
acylsulfonamides selected from the structures CONM$^b$SO$_2$R$^x$, CONM$^b$SO$_2$N($R^y$)$R^z$, SO$_2$NM$^b$CON($R^y$)$R^z$; and SO$_2$NM$^b$CN, where $R^x$ is phenyl or heteroaryl, where heteroaryl is a monocyclic aromatic hydrocarbon group having 5 or 6 ring atoms, in which a carbon atom is the point of attachment, in which one of the carbon atoms has been replaced by a nitrogen atom, in which one additional carbon atom is optionally replaced by a heteroatom selected from O or S, and in which from 1 to 2 additional carbon atoms are optionally replaced by a nitrogen heteroatom, and where the phenyl and heteroaryl are optionally mono-substituted by $R^q$, as defined above; M$^b$ is as defined above; and $R^y$ and $R^z$ are as defined above;

ad) $C_5$-$C_7$ cycloalkyl group in which one of the carbon atoms in the ring is replaced by a heteroatom selected from O, S, NH, or N($C_1$-$C_4$ alkyl) and in which one additional carbon may be replaced by NH or N($C_1$-$C_4$ alkyl), and in which at least one carbon atom adjacent to each nitrogen heteroatom has both of its attached hydrogen atoms replaced by one oxygen thus forming a carbonyl moiety and there are one or two carbonyl moieties present in the ring;

ae) $C_2$-$C_4$ alkenyl radical, optionally mono-substituted by one of the substituents b) to ad) above and phenyl which is optionally substituted by $R^q$ as defined above;

af) C₂–C₄ alkynyl radical, optionally mono-substituted by one of the substituents b) to ad) above;

ag) C₁–C₄ alkyl radical;

ah) C₁–C₄ alkyl mono-substituted by one of the substituents b)–ad) above; or ai) a 2-oxazolidinonyl moiety in which the point of attachment is the nitrogen atom of the oxazolidinone ring, the ring oxygen atom is optionally replaced by a heteroatom selected from S and NR$^I$ (where R$^I$ is as defined above) and one of the saturated carbon atoms of the oxazolidinone ring is optionally mono-substituted by one of the substituents b) to ah) above;

M is:
i) hydrogen;
ii) a pharmaceutically acceptable esterifying group or removable carboxyl protecting group; or
iii) an alkali metal or other pharmaceutically acceptable cation.

2. The compound of claim 1, wherein R¹ is hydrogen and R² is (R)—CH₃CH(OH)— or (R)—CH₃CH(F)—.

3. The compound of claim 2, wherein Y is:

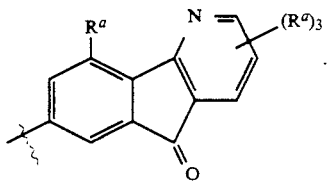

4. The compound of claim 2, wherein Y is:

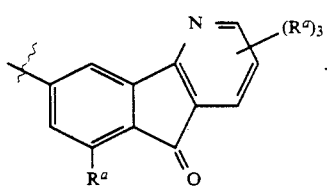

5. The compound of claim 2 wherein one to three R$^a$ substituents are selected from:

| | |
|---|---|
| —OCH₃ | —OCH₂CO₂CH₃ |
| —OCH₂CH₂OH | —CF₃ |
| —F | —Cl |
| —Br | —I |
| —OH | —OCOCH₃ |
| —OCONH₂ | —SCH₃ |
| —SOCH₃ | —SO₂CH₃ |
| —SCH₂CH₂OH | —SOCH₂CH₂OH |
| —SO₂NH₂ | —SO₂N(CH₃)₂ |
| —NHCHO | —NHCOCH₃ |
| —NHCO₂CH₃ | —NHSO₂CH₃ |
| —CN | —CHO |
| —COCH₃ | —COCH₂OH |
| —CH=NOH | —CH=NOCH₃ |
| —CH=NOCH₂CO₂CH₃ | —CH=NOCMe₂CO₂CH₃ |
| —SO₂CH₂CH₂OH | —CO₂CH₂CH₂OH |
| —CH=NOCMe₂CO₂Me | —CONHCH₃ |
| —CONH₂ | —CONHCH₂CN |
| —CON(CH₃)₂ | —CONHCH₂CO₂CH₃ |
| —CONHCH₂CONH₂ | —CONHCH₃ |
| —CONHOH | —CO₂CH₃ |
| -tetrazolyl | —PO₃CH₃H |
| —SCF₃ | —CONHSO₂NH₂ |
| —CONHSO₂Ph | —SO₂NHCN |
| —SO₃CH₃ | —CH=CHCN |
| —SO₂NHCONH₂ | —CH=CHCO₂CH₃ |
| —CH=CHCONH₂ | —C≡C—CN |
| —C≡C—CONH₂ | —CH₂N₃ |
| —CH₂OH | —CH₂I. |
| —CH₂CO₂CH₃ and | |

6. The compound of claim 1, wherein the structural formula is:

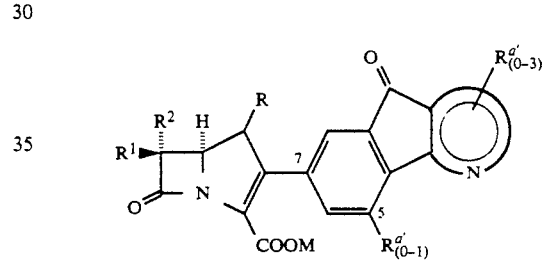

and the substituents R$^{a'}$ (which is R$^a$ when it is not hydrogen), R, R¹, R² and M are as defined in Table I below and when R² is 1-fluoroethyl or 1-hydroxyethyl the stereochemistry is (R):

TABLE I

| N— pos. | R | R¹ | R² | M | R$^{a'}$ | R$^{a'}$ position |
|---|---|---|---|---|---|---|
| 1 | —H | —H | —CH(OH)CH₃ | Na⁺ | —CHO | 2 |
| 1 | —H | —H | —CH(OH)CH₃ | Na⁺ | —CHO | 3 |
| 2 | —H | —H | —CH(OH)CH₃ | Na⁺ | —CHO | 5 |
| 2 | —H | —H | —CH(OH)CH₃ | Na⁺ | —CHO | 3 |
| 2 | —H | —H | —CH(OH)CH₃ | Na⁺ | —CHO | 4 |
| 3 | —H | —H | —CH(OH)CH₃ | Na⁺ | —CHO | 1 |
| 3 | —H | —H | —CH(OH)CH₃ | Na⁺ | —CHO | 5 |
| 4 | —H | —H | —CH(OH)CH₃ | Na⁺ | —CHO | 3 |
| 4 | —H | —H | —CH(OH)CH₃ | Na⁺ | —CHO | 5 |
| 1 | —H | —H | —CH(OH)CH₃ | Na⁺ | —CN | 2 |
| 1 | —H | —H | —CH(OH)CH₃ | Na⁺ | —CN | 3 |
| 2 | —H | —H | —CH(OH)CH₃ | Na⁺ | —CN | 5 |
| 2 | —H | —H | —CH(OH)CH₃ | Na⁺ | —CN | 3 |
| 2 | —H | —H | —CH(OH)CH₃ | Na⁺ | —CN | 4 |
| 3 | —H | —H | —CH(OH)CH₃ | Na⁺ | —CN | 1 |
| 3 | —H | —H | —CH(OH)CH₃ | Na⁺ | —CN | 5 |
| 4 | —H | —H | —CH(OH)CH₃ | Na⁺ | —CN | 3 |
| 4 | —H | —H | —CH(OH)CH₃ | Na⁺ | —CN | 5 |
| 4 | —H | —H | —CH(OH)CH₃ | Na⁺ | —CN | 2 |
| 1 | —H | —H | —CH(OH)CH₃ | Na⁺ | —CH=NOH | 2 |
| 1 | —H | —H | —CH(OH)CH₃ | Na⁺ | —CH=NOH | 3 |
| 2 | —H | —H | —CH(OH)CH₃ | Na⁺ | —CH=NOH | 5 |
| 2 | —H | —H | —CH(OH)CH₃ | Na⁺ | —CH=NOH | 3 |
| 2 | —H | —H | —CH(OH)CH₃ | Na⁺ | —CH=NOH | 4 |
| 3 | —H | —H | —CH(OH)CH₃ | Na⁺ | —CH=NOH | 1 |

TABLE I-continued

| N— pos. | R | $R^1$ | $R^2$ | M | $R^{a'}$ | $R^{a'}$ position |
|---|---|---|---|---|---|---|
| 3 | —H | —H | —CH(OH)CH₃ | Na⁺ | —CH=NOH | 5 |
| 4 | —H | —H | —CH(OH)CH₃ | Na⁺ | —CH=NOH | 3 |
| 4 | —H | —H | —CH(OH)CH₃ | Na⁺ | —CH=NOH | 5 |
| 4 | —H | —H | —CH(OH)CH₃ | Na⁺ | —CH=NOH | 2 |
| 1 | —H | —H | —CH(OH)CH₃ | Na⁺ | —CH₂OH | 2 |
| 1 | —H | —H | —CH(OH)CH₃ | Na⁺ | —CH₂OH | 3 |
| 2 | —H | —H | —CH(OH)CH₃ | Na⁺ | —CH₂OH | 5 |
| 2 | —H | —H | —CH(OH)CH₃ | Na⁺ | —CH₂OH | 3 |
| 2 | —H | —H | —CH(OH)CH₃ | Na⁺ | —CH₂OH | 4 |
| 3 | —H | —H | —CH(OH)CH₃ | Na⁺ | —CH₂OH | 1 |
| 3 | —H | —H | —CH(OH)CH₃ | Na⁺ | —CH₂OH | 5 |
| 4 | —H | —H | —CH(OH)CH₃ | Na⁺ | —CH₂OH | 3 |
| 4 | —H | —H | —CH(OH)CH₃ | Na⁺ | —CH₂OH | 5 |
| 4 | —H | —H | —CH(OH)CH₃ | Na⁺ | —CH₂OH | 2 |
| 1 | —H | —H | —CH(OH)CH₃ | Na⁺ | —CONH₂ | 2 |
| 1 | —H | —H | —CH(OH)CH₃ | Na⁺ | —CONH₂ | 3 |
| 2 | —H | —H | —CH(OH)CH₃ | Na⁺ | —CONH₂ | 5 |
| 2 | —H | —H | —CH(OH)CH₃ | Na⁺ | —CONH₂ | 3 |
| 2 | —H | —H | —CH(OH)CH₃ | Na⁺ | —CONH₂ | 4 |
| 3 | —H | —H | —CH(OH)CH₃ | Na⁺ | —CONH₂ | 1 |
| 3 | —H | —H | —CH(OH)CH₃ | Na⁺ | —CONH₂ | 5 |
| 4 | —H | —H | —CH(OH)CH₃ | Na⁺ | —CONH₂ | 3 |
| 4 | —H | —H | —CH(OH)CH₃ | Na⁺ | —CONH₂ | 5 |
| 4 | —H | —H | —CH(OH)CH₃ | Na⁺ | —CONH₂ | 2 |
| 1 | —H | —H | —CH(OH)CH₃ | Na⁺ | —CO₂CH₃ | 2 |
| 1 | —H | —H | —CH(OH)CH₃ | Na⁺ | —CO₂CH₃ | 3 |
| 2 | —H | —H | —CH(OH)CH₃ | Na⁺ | —CO₂CH₃ | 5 |
| 2 | —H | —H | —CH(OH)CH₃ | Na⁺ | —CO₂CH₃ | 3 |
| 2 | —H | —H | —CH(OH)CH₃ | Na⁺ | —CO₂CH₃ | 4 |
| 3 | —H | —H | —CH(OH)CH₃ | Na⁺ | —CO₂CH₃ | 1 |
| 3 | —H | —H | —CH(OH)CH₃ | Na⁺ | —CO₂CH₃ | 5 |
| 4 | —H | —H | —CH(OH)CH₃ | Na⁺ | —CO₂CH₃ | 3 |
| 4 | —H | —H | —CH(OH)CH₃ | Na⁺ | —CO₂CH₃ | 5 |
| 4 | —H | —H | —CH(OH)CH₃ | Na⁺ | —CO₂CH₃ | 2 |
| 2 | —H | —H | —CH(OH)CH₃ | Na⁺ | —OCH₂CO₂CH₃ | 3 |
| 1 | —H | —H | —CH(OH)CH₃ | K+ | —OCH₃ | 2 |
| 3 | —H | —H | —CH(OH)CH₃ | K+ | —OCH₂CH₂OH | 2 |
| 4 | —H | —H | —CH(OH)CH₃ | K+ | —CF₃ | 3 |
| 3 | —H | —H | —CH(OH)CH₃ | Na⁺ | —F | 1 |
| 2 | —H | —H | —CH(OH)CH₃ | Na⁺ | —Cl | 5 |
| 4 | —H | —H | —CH(OH)CH₃ | K+ | —Br | 3 |
| 1 | —H | —H | —CH₂OH | K+ | —I | 2 |
| 3 | —H | —H | —CH(OH)CH₃ | K+ | —OH | 5 |
| 2 | —H | —H | —CH(OH)CH₃ | Na⁺ | —OCOCH₃ | 3 |
| 1 | —H | —H | —CH(OH)CH₃ | Na⁺ | —OCONH₂ | 2 |
| 2 | —H | —H | —CH(OH)CH₃ | Na⁺ | —SCH₃ | 5 |
| 3 | —H | —H | —CH(F)CH₃ | K+ | —SOCH₃ | 2 |
| 4 | —CH₃ | —H | —CH(OH)CH₃ | Na⁺ | —SO₂CH₃ | 5 |
| 3 | —H | —H | —CH(OH)CH₃ | Na⁺ | —SCH₂CH₂OH | 2 |
| 4 | —H | —H | —CH(OH)CH₃ | Na⁺ | —SOCH₂CH₂OH | 3 |
| 2 | —H | —H | —CH(OH)CH₃ | K+ | —SO₂CH₂CH₂OH | 3 |
| 2 | —H | —H | —CH(OH)CH₃ | Na⁺ | —SO₂NH₂ | 4 |
| 2 | —H | —H | —CH(OH)CH₃ | K+ | —SO₂N(CH₃)₂ | 1 |
| 3 | —H | —H | —CF₂CH₃ | K+ | —NHCHO | 3 |
| 1 | —CH₃ | —H | —CH(OH)CH₃ | K+ | —NHCOCH₃ | 2 |
| 4 | —H | —H | —CH(OH)CH₃ | K+ | —NHCO₂CH₃ | 3 |
| 3 | —H | —H | —CH(OH)CH₃ | Na⁺ | —NHSO₂CH₃ | 2 |
| 3 | —H | —H | —CH(OH)CH₃ | Na⁺ | —COCH₃ | 4 |
| 1 | —H | —H | —CH(OH)CH₃ | K+ | —COCH₂OH | 5 |
| 2 | —H | —H | —CH(OH)CH₃ | Na⁺ | —CH=NOCH₃ | 3 |
| 3 | —H | —H | —CH(OH)CH₃ | K+ | —CH=NOCH₂CO₂CH₃ | 1 |
| 4 | —CH₃ | —H | —CH(OH)CH₃ | Na⁺ | —CH=NOCMe₂CO₂Me | 3 |
| 2 | —H | —H | —CH(OH)CH₃ | Na⁺ | —CH=NOCMe₂CO₂Me | 1 |
| 3 | —H | —H | —CH(OH)CH₃ | K+ | —CO₂CH₂CH₂OH | 5 |
| 2 | —H | —H | —CH(OH)CH₃ | K+ | —CONHCH₃ | 3 |
| 4 | —H | —H | —CH(OH)CH₃ | K+ | —CON(CH₃)₂ | 3 |
| 2 | —H | —H | —CH(OH)CH₃ | K+ | —CONHCH₂CN | 5 |
| 2 | —CH₃ | —H | —CF₂CH₃ | Na⁺ | —CONHCH₂CONH₂ | 1 |
| 3 | —H | —H | —CH(OH)CH₃ | K+ | —CONHCH₂CO₂CH₃ | 4 |
| 1 | —H | —H | —CH(OH)CH₃ | Na⁺ | —CONHOH | 2 |
| 1 | —H | —H | —CH(OH)CH₃ | Na⁺ | —CONHOCH₃ | 5 |
| 3 | —H | —H | —CH(OH)CH₃ | Na⁺ | -tetrazolyl | 2 |
| 4 | —H | —H | —CH(OH)CH₃ | Na⁺ | —SCF₃ | 3 |
| 2 | —H | —H | —CH(OH)CH₃ | Na⁺ | —PO₃CH₃H | 5 |
| 3 | —H | —H | —CH(OH)CH₃ | Na⁺ | —CONHSO₂Ph | 2 |
| 3 | —CH₃ | —H | —CH(OH)CH₃ | Na⁺ | —CONHSO₂NH₂ | 5 |
| 2 | —H | —H | —CH(OH)CH₃ | Na⁺ | —SO₃CH₃ | 3 |
| 4 | —H | —H | —CH(OH)CH₃ | Na⁺ | —SO₂NHCN | 3 |
| 2 | —CH₃ | —H | —CH(F)CH₃ | Na⁺ | —SO₂NHCONH₂ | 5 |
| 1 | —H | —H | —CH(OH)CH₃ | K+ | —CH=CHCN | 5 |
| 2 | —H | —H | —CH(OH)CH₃ | K+ | —CH=CHCONH₂ | 1 |

TABLE I-continued

| N— pos. | R | $R^1$ | $R^2$ | M | $R^{a'}$ | $R^{a'}$ position |
|---|---|---|---|---|---|---|
| 2 | —H | —H | —CH(OH)CH$_3$ | Na$^+$ | —CH=CHCO$_2$CH$_3$ | 3 |
| 4 | —H | —H | —CH(OH)CH$_3$ | Na$^+$ | —C≡C—CONH$_2$ | 3 |
| 3 | —CH$_3$ | —H | —CH(OH)CH$_3$ | Na$^+$ | —C≡C—CN | 2 |
| 4 | —H | —H | —CH$_2$CH$_3$ | K$^+$ | —CH$_2$N$_3$ | 5 |
| 2 | —H | —H | —CH(OH)CH$_3$ | Na$^+$ | —CH$_2$CO$_2$CH$_3$ | 3 |
| 1 | —H | —H | —CH(OH)CH$_3$ | Na$^+$ | —CH$_2$CO$_2$CH$_3$ | 2 |
| 3 | —CH$_3$ | —H | —CH(OH)CH$_3$ | Na$^+$ | —CN | 5 |
| 3 | —H | —H | —CH(OH)CH$_3$ | Na$^+$ | —CO$_2$CH$_3$ | 1 |
| 3 | —H | —H | —CH(F)CH$_3$ | Na$^+$ | —CO$_2$CH$_3$ | 2 |
| 2 | —CH$_3$ | —H | —CH(OH)CH$_3$ | Na$^+$ | —CH$_2$CO$_2$CH$_3$ | 5 |
| 3 | —H | —H | —CH(OH)CH$_3$ | Na$^+$ | —SCH$_3$ | 5 |
| 2 | —H | —H | —CH(F)CH$_3$ | Na$^+$ | —SOCH$_3$ | 4 |
| 4 | —CH$_3$ | —H | —CH(OH)CH$_3$ | Na$^+$ | —SO$_2$CH$_3$ | 5 |
| 3 | —H | —H | —CH(OH)CH$_3$ | Na$^+$ | —CH=CHCN | 2 |
| 1 | —H | —H | —CH(OH)CH$_3$ | Na$^+$ | —CH=CHCN | 2 |
| 3 | —H | —H | —CH(OH)CH$_3$ | Na$^+$ | —SOCH$_3$ | 1 or |
| 3 | —H | —H | —CH(OH)CH$_3$ | Na$^+$ | —SOCH$_3$ | 5. |

7. The compound of claim 1, wherein the structural formula is:

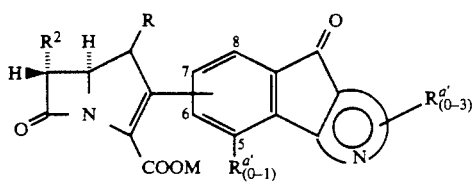

and the substituents $R^{a'}$ (where $R^{a'}$ is $R^a$ when it is not hydrogen), R, $R^2$ and M and the point of attachment of the carbapenem to the azafluorenone and position of the nitrogen in the azafluorenone are as defined in Table II below, and when $R^2$ is 1-fluoroethyl or 1-hydroxyethyl the stereochemistry is (R):

TABLE II

| N— pos. | Att pt | R | $R^2$ | M | $R^{a'}$ | $R^{a'}$ position |
|---|---|---|---|---|---|---|
| 1 | 5 | —H | —CH(OH)CH$_3$ | Na$^+$ | —CHO | 2 |
| 1 | 6 | —H | —CH(OH)CH$_3$ | Na$^+$ | —CHO | 3 |
| 2 | 8 | —H | —CH(OH)CH$_3$ | Na$^+$ | —CHO | 5 |
| 2 | 5 | —H | —CH(OH)CH$_3$ | Na$^+$ | —CHO | 3 |
| 2 | 6 | —H | —CH(OH)CH$_3$ | Na$^+$ | —CHO | 4 |
| 3 | 5 | —H | —CH(OH)CH$_3$ | Na$^+$ | —CHO | 1 |
| 3 | 8 | —H | —CH(OH)CH$_3$ | Na$^+$ | —CHO | 5 |
| 4 | 6 | —H | —CH(OH)CH$_3$ | Na$^+$ | —CHO | 3 |
| 4 | 5 | —H | —CH(OH)CH$_3$ | Na$^+$ | —CHO | 5 |
| 1 | 6 | —H | —CH(OH)CH$_3$ | Na$^+$ | —CN | 2 |
| 1 | 6 | —H | —CH(OH)CH$_3$ | Na$^+$ | —CN | 3 |
| 2 | 8 | —H | —CH(OH)CH$_3$ | Na$^+$ | —CN | 5 |
| 2 | 8 | —H | —CH(OH)CH$_3$ | Na$^+$ | —CN | 3 |
| 2 | 5 | —H | —CH(OH)CH$_3$ | Na$^+$ | —CN | 4 |
| 3 | 8 | —H | —CH(OH)CH$_3$ | Na$^+$ | —CN | 1 |
| 3 | 5 | —H | —CH(OH)CH$_3$ | Na$^+$ | —CN | 2 |
| 4 | 6 | —H | —CH(OH)CH$_3$ | Na$^+$ | —CN | 3 |
| 4 | 6 | —H | —CH(OH)CH$_3$ | Na$^+$ | —CN | 1 |
| 4 | 5 | —H | —CH(OH)CH$_3$ | Na$^+$ | —CN | 2 |
| 1 | 6 | —H | —CH(OH)CH$_3$ | Na$^+$ | —CH=NOH | 2 |
| 1 | 8 | —H | —CH(OH)CH$_3$ | Na$^+$ | —CH=NOH | 3 |
| 2 | 8 | —H | —CH(OH)CH$_3$ | Na$^+$ | —CH=NOH | 5 |
| 2 | 5 | —H | —CH(OH)CH$_3$ | Na$^+$ | —CH=NOH | 3 |
| 2 | 6 | —H | —CH(OH)CH$_3$ | Na$^+$ | —CH=NOH | 4 |
| 3 | 5 | —H | —CH(OH)CH$_3$ | Na$^+$ | —CH=NOH | 1 |
| 3 | 6 | —H | —CH(OH)CH$_3$ | Na$^+$ | —CH=NOH | 2 |
| 4 | 6 | —H | —CH(OH)CH$_3$ | Na$^+$ | —CH=NOH | 3 |
| 4 | 6 | —H | —CH(OH)CH$_3$ | Na$^+$ | —CH=NOH | 1 |
| 4 | 8 | —H | —CH(OH)CH$_3$ | Na$^+$ | —CH=NOH | 2 |
| 1 | 6 | —H | —CH(OH)CH$_3$ | Na$^+$ | —CH$_2$OH | 2 |
| 1 | 6 | —H | —CH(OH)CH$_3$ | Na$^+$ | —CH$_2$OH | 3 |
| 2 | 8 | —H | —CH(OH)CH$_3$ | Na$^+$ | —CH$_2$OH | 5 |
| 2 | 6 | —H | —CH(OH)CH$_3$ | Na$^+$ | —CH$_2$OH | 3 |
| 2 | 6 | —H | —CH(OH)CH$_3$ | Na$^+$ | —CH$_2$OH | 4 |
| 3 | 5 | —H | —CH(OH)CH$_3$ | Na$^+$ | —CH$_2$OH | 1 |
| 3 | 6 | —H | —CH(OH)CH$_3$ | Na$^+$ | —CH$_2$OH | 2 |
| 4 | 8 | —H | —CH(OH)CH$_3$ | Na$^+$ | —CH$_2$OH | 3 |
| 4 | 6 | —H | —CH(OH)CH$_3$ | Na$^+$ | —CH$_2$OH | 3 |
| 4 | 5 | —H | —CH(OH)CH$_3$ | Na$^+$ | —CH$_2$OH | 2 |
| 1 | 6 | —H | —CH(OH)CH$_3$ | Na$^+$ | —CONH$_2$ | 2 |
| 1 | 6 | —H | —CH(OH)CH$_3$ | Na$^+$ | —CONH$_2$ | 3 |
| 2 | 8 | —H | —CH(OH)CH$_3$ | Na$^+$ | —CONH$_2$ | 5 |
| 2 | 6 | —H | —CH(OH)CH$_3$ | Na$^+$ | —CONH$_2$ | 3 |
| 2 | 6 | —H | —CH(OH)CH$_3$ | Na$^+$ | —CONH$_2$ | 4 |
| 3 | 8 | —H | —CH(OH)CH$_3$ | Na$^+$ | —CONH$_2$ | 1 |

TABLE II-continued

| N— pos. | Att pt | R | $R^2$ | M | $R^{a'}$ | $R^{a'}$ position |
|---|---|---|---|---|---|---|
| 3 | 6 | —H | —CH(OH)CH$_3$ | Na$^+$ | —CONH$_2$ | 2 |
| 4 | 6 | —H | —CH(OH)CH$_3$ | Na$^+$ | —CONH$_2$ | 3 |
| 4 | 5 | —H | —CH(OH)CH$_3$ | Na$^+$ | —CONH$_2$ | 2 |
| 4 | 8 | —H | —CH(OH)CH$_3$ | Na$^+$ | —CONH$_2$ | 2 |
| 1 | 6 | —H | —CH(OH)CH$_3$ | Na$^+$ | —CO$_2$CH$_3$ | 2 |
| 1 | 5 | —H | —CH(OH)CH$_3$ | Na$^+$ | —CO$_2$CH$_3$ | 3 |
| 2 | 6 | —H | —CH(OH)CH$_3$ | Na$^+$ | —CO$_2$CH$_3$ | 1 |
| 2 | 6 | —H | —CH(OH)CH$_3$ | Na$^+$ | —CO$_2$CH$_3$ | 3 |
| 2 | 5 | —H | —CH(OH)CH$_3$ | Na$^+$ | —CO$_2$CH$_3$ | 4 |
| 3 | 6 | —H | —CH(OH)CH$_3$ | Na$^+$ | —CO$_2$CH$_3$ | 1 |
| 3 | 6 | —H | —CH(OH)CH$_3$ | Na$^+$ | —CO$_2$CH$_3$ | 2 |
| 4 | 8 | —H | —CH(OH)CH$_3$ | Na$^+$ | —CO$_2$CH$_3$ | 3 |
| 4 | 8 | —H | —CH(OH)CH$_3$ | Na$^+$ | —CO$_2$CH$_3$ | 5 |
| 4 | 6 | —H | —CH(OH)CH$_3$ | Na$^+$ | —CO$_2$CH$_3$ | 2 |
| 2 | 6 | —H | —CH(OH)CH$_3$ | Na$^+$ | —OCH$_2$CO$_2$CH$_3$ | 3 |
| 1 | 6 | —H | —CH(OH)CH$_3$ | K$^+$ | —OCH$_3$ | 2 |
| 3 | 5 | —H | —CH(OH)CH$_3$ | K$^+$ | —OCH$_2$CH$_2$OH | 2 |
| 4 | 6 | —H | —CH(OH)CH$_3$ | K$^+$ | —CF$_3$ | 3 |
| 3 | 6 | —H | —CH(OH)CH$_3$ | Na$^+$ | —F | 1 |
| 2 | 8 | —H | —CH(OH)CH$_3$ | Na$^+$ | —Cl | 5 |
| 4 | 6 | —H | —CH(OH)CH$_3$ | K$^+$ | —Br | 3 |
| 1 | 6 | —H | —CH$_2$OH | K$^+$ | —I | 2 |
| 3 | 8 | —H | —CH(OH)CH$_3$ | K$^+$ | —OH | 5 |
| 2 | 5 | —H | —CH(OH)CH$_3$ | Na$^+$ | —OCOCH$_3$ | 3 |
| 1 | 5 | —H | —CH(OH)CH$_3$ | Na$^+$ | —OCONH$_2$ | 2 |
| 2 | 6 | —H | —CH(OH)CH$_3$ | Na$^+$ | —SCH$_3$ | 1 |
| 3 | 6 | —H | —CH(F)CH$_3$ | K$^+$ | —SOCH$_2$CH$_2$OH | 3 |
| 4 | 5 | —CH$_3$ | —CH(OH)CH$_3$ | Na$^+$ | —SO$_2$CH$_3$ | 2 |
| 3 | 6 | —H | —CH(OH)CH$_3$ | Na$^+$ | —SCH$_2$CH$_2$OH | 2 |
| 4 | 8 | —H | —CH(OH)CH$_3$ | Na$^+$ | —SOCH$_2$CH$_2$OH | 3 |
| 2 | 6 | —H | —CH(OH)CH$_3$ | K$^+$ | —SO$_2$CH$_2$CH$_2$OH | 3 |
| 2 | 6 | —H | —CH(OH)CH$_3$ | Na$^+$ | —SO$_2$NH$_2$ | 4 |
| 2 | 6 | —H | —CH(OH)CH$_3$ | K$^+$ | —SO$_2$N(CH$_3$)$_2$ | 1 |
| 3 | 6 | —H | —CF$_2$CH$_3$ | K$^+$ | —NHCHO | 2 |
| 1 | 5 | —CH$_3$ | —CH(OH)CH$_3$ | K$^+$ | —NHCOCH$_3$ | 2 |
| 4 | 6 | —H | —CH(OH)CH$_3$ | K$^+$ | —NHCO$_2$CH$_3$ | 3 |
| 3 | 8 | —H | —CH(OH)CH$_3$ | Na$^+$ | —NHSO$_2$CH$_3$ | 2 |
| 3 | 6 | —H | —CH(OH)CH$_3$ | K$^+$ | —COCH$_3$ | 4 |
| 1 | 8 | —H | —CH(OH)CH$_3$ | K$^+$ | —COCH$_2$OH | 5 |
| 2 | 6 | —H | —CH(OH)CH$_3$ | Na$^+$ | —CH=NOCH$_3$ | 3 |
| 3 | 6 | —H | —CH(OH)CH$_3$ | K$^+$ | —CH=NOCH$_2$CO$_2$CH$_3$ | 1 |
| 4 | 6 | —CH$_3$ | —CH(OH)CH$_3$ | Na$^+$ | —CH=NOCMe$_2$CO$_2$Me | 3 |
| 2 | 6 | —H | —CH(OH)CH$_3$ | Na$^+$ | —CH=NOCMe$_2$CO$_2$Me | 1 |
| 3 | 8 | —H | —CH(OH)CH$_3$ | K$^+$ | —CO$_2$CH$_2$CH$_2$OH | 5 |
| 2 | 5 | —H | —CH(OH)CH$_3$ | K$^+$ | —CONHCH$_3$ | 3 |
| 4 | 6 | —H | —CH(OH)CH$_3$ | K$^+$ | —CON(CH$_3$)$_2$ | 3 |
| 2 | 8 | —H | —CH(OH)CH$_3$ | K$^+$ | —CONHCH$_2$CN | 5 |
| 2 | 6 | —CH$_3$ | —CF$_2$CH$_3$ | Na$^+$ | —CONHCH$_2$CONH$_2$ | 1 |
| 3 | 6 | —H | —CH(OH)CH$_3$ | K$^+$ | —CONHCH$_2$CO$_2$CH$_3$ | 4 |
| 1 | 6 | —H | —CH(OH)CH$_3$ | Na$^+$ | —CONHOH | 2 |
| 1 | 8 | —H | —CH(OH)CH$_3$ | Na$^+$ | —CONHOCH$_3$ | 5 |
| 3 | 5 | —H | —CH(OH)CH$_3$ | Na$^+$ | -tetrazolyl | 2 |
| 4 | 6 | —H | —CH(OH)CH$_3$ | Na$^+$ | —SCF$_3$ | 3 |
| 2 | 6 | —H | —CH(OH)CH$_3$ | Na$^+$ | —PO$_3$CH$_3$H | 4 |
| 3 | 6 | —H | —CH(OH)CH$_3$ | Na$^+$ | —CONHSO$_2$Ph | 2 |
| 3 | 8 | —CH$_3$ | —CH(OH)CH$_3$ | Na$^+$ | —CONHSO$_2$NH$_2$ | 5 |
| 2 | 6 | —H | —CH(OH)CH$_3$ | Na$^+$ | —SO$_3$CH$_3$ | 3 |
| 4 | 6 | —H | —CH(OH)CH$_3$ | Na$^+$ | —SO$_2$NHCN | 3 |
| 2 | 8 | —CH$_3$ | —CH(F)CH$_3$ | Na$^+$ | —SO$_2$NHCONH$_2$ | 5 |
| 1 | 8 | —H | —CH(OH)CH$_3$ | K$^+$ | —CH=CHCN | 5 |
| 2 | 6 | —H | —CH(OH)CH$_3$ | K$^+$ | —CH=CHCONH$_2$ | 1 |
| 2 | 6 | —H | —CH(OH)CH$_3$ | Na$^+$ | —CH=CHCO$_2$CH$_3$ | 3 |
| 4 | 6 | —H | —CH(OH)CH$_3$ | Na$^+$ | —C≡C—CONH$_2$ | 3 |
| 3 | 6 | —CH$_3$ | —CH(OH)CH$_3$ | Na$^+$ | —C≡C—CN | 2 |
| 4 | 8 | —H | —CH$_2$CH$_3$ | K$^+$ | —CH$_2$N$_3$ | 5 |
| 2 | 6 | —H | —CH(OH)CH$_3$ | Na+ | —CH$_2$CO$_2$CH$_3$ | 3 |
| 1 | 6 | —H | —CH(OH)CH$_3$ | Na$^+$ | —CH$_2$CO$_2$CH$_3$ | 2 |
| 3 | 8 | —CH$_3$ | —CH(OH)CH$_3$ | Na$^+$ | —CN | 3 |
| 3 | 6 | —H | —CH(OH)CH$_3$ | Na$^+$ | —CO$_2$CH$_3$ | 1 |
| 3 | 6 | —H | —CH(F)CH$_3$ | Na$^+$ | —CO$_2$CH$_3$ | 2 |
| 2 | 6 | —CH$_3$ | —CH(OH)CH$_3$ | Na$^+$ | —CH$_2$CO$_2$CH$_3$ | 2 |
| 3 | 8 | —H | —CH(OH)CH$_3$ | Na$^+$ | —SCH$_3$ | 5 |
| 2 | 6 | —H | —CH(F)CH$_3$ | Na$^+$ | —SOCH$_3$ | 4 |
| 4 | 6 | —CH$_3$ | —CH(OH)CH$_3$ | Na$^+$ | —SO$_2$CH$_3$ | 2 |
| 3 | 6 | —H | —CH(OH)CH$_3$ | Na$^+$ | —CH=CHCN | 2 |
| 1 | 5 | —H | —CH(OH)CH$_3$ | Na$^+$ | —CH=CHCN | 2 |
| 3 | 6 | —H | —CH(OH)CH$_3$ | Na$^+$ | —SOCH$_3$ | 1 or |
| 3 | 8 | —H | —CH(OH)CH$_3$ | Na$^+$ | —SOCH$_3$ | 5. |

8. A compound wherein the structural formula is:

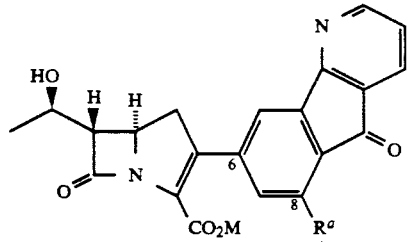

and M is Na+ or K+ and the R^a substituent is selected from $CH_2OH$, $CO_2CH_3$, $CONH_2$, Cl, CN, CHO, $SCH_3$, $SOCH_2CH_2OH$ and $SO_2CH_3$.

9. A compound wherein the structural formula is:

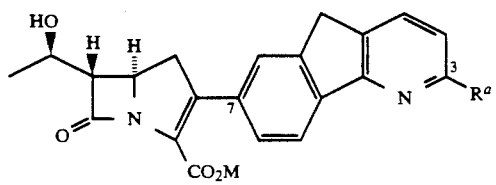

and M is Na+ or K+ and the R^a substituent is selected from $CH_2OH$, $CO_2CH_3$, $CONH_2$, Cl, CN, $SCH_3$, $SOCH_2CH_2OH$, $SO_2CH_3$ and CHO.

10. A compound selected from the group consisting of:

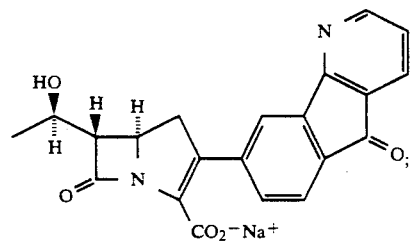

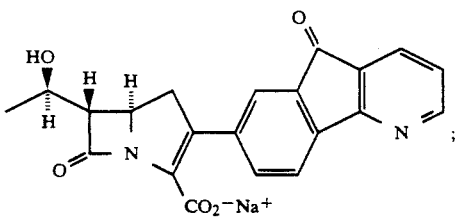

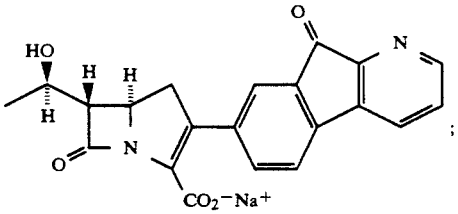

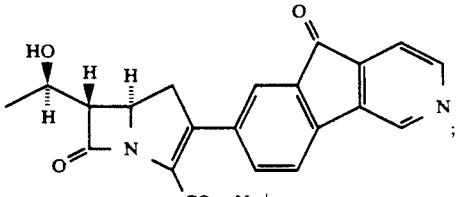

-continued

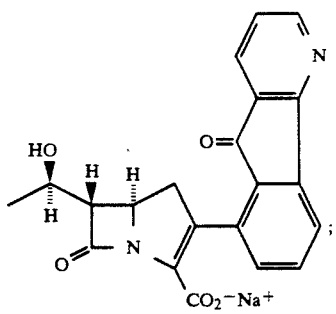

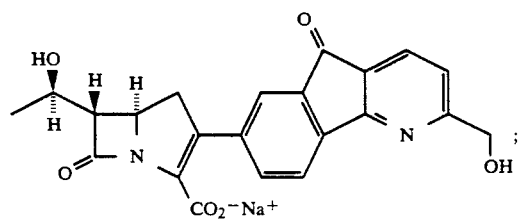

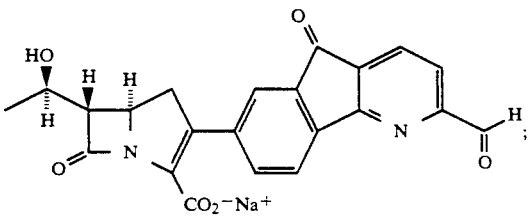

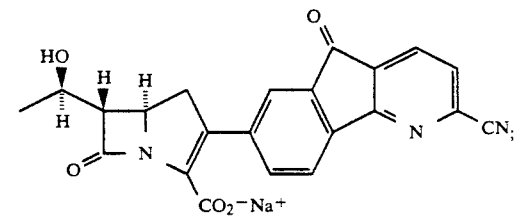

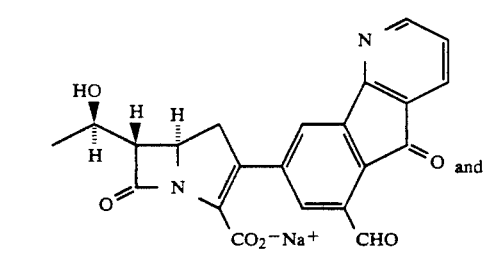

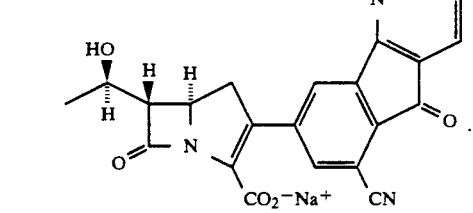

11. A pharmaceutical composition for antibacterial use comprising an antibacterially effective amount of a compound of claim 1 and a pharmaceutically acceptable carrier.

12. A method of treating bacterial infections in human or animal subjects in need of such treatment comprising administering to such subject an antibacterially effective amount of a compound of claim 1.

13. A pharmaceutical composition for antibacterial use comprising an antibacterially effective amount of a compound of claim 1, an inhibitorily effective amount of a dehydropeptidase (DHP) inhibitor, and optionally, a pharmaceutically acceptable carrier.

14. A pharmaceutical composition according to claim 13, wherein the DHP inhibitor is 7-(L-2-amino-2-carboxyethylthio)-2-(2,2-dimethylcyclopropanecarboxamide)-2-heptenoic acid.

15. A method of treating bacterial infections in human or animal subjects in need of such treatment comprising coadministering to such subject an antibacterially effective amount of a compound of claim 1 and an inhibitorily effective amount of a DHP inhibitor.

16. The method according to claim 15, wherein the DHP inhibitor is 7-(L-2-amino-2-carboxyethylthio)-2-(2,2-dimethylcyclopropanecarboxamide)-2-heptenoic acid.

* * * * *

UNITED STATES PATENT AND TRADEMARK OFFICE
CERTIFICATE OF CORRECTION

PATENT NO. : 5,294,610
DATED : March 15, 1994
INVENTOR(S) : F. P. DiNinno and R. N. Guthikonda It is certified that error appears in the above-indentified patent and that said Letters Patent is hereby corrected as shown below:

Column 73, between lines 15-25 in claim 9, please replace the structure with the following:

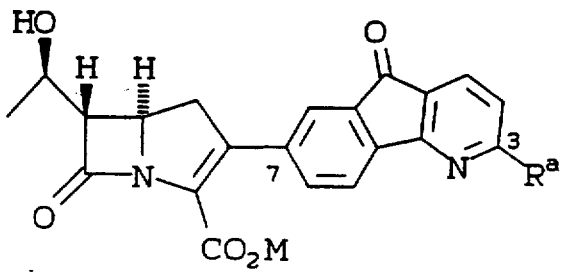

Signed and Sealed this

Fourteenth Day of May, 1996

*Attest:*

BRUCE LEHMAN

*Attesting Officer*  *Commissioner of Patents and Trademarks*